(12) United States Patent
Hangauer, Jr. et al.

(10) Patent No.: US 8,901,297 B2
(45) Date of Patent: Dec. 2, 2014

(54) COMPOSITIONS FOR MODULATING A KINASE CASCADE AND METHODS OF USE THEREOF

(75) Inventors: David G. Hangauer, Jr., Lancaster, NY (US); Debasis Patra, Manlius, NY (US); Jeremy A. Cody, Clifton Springs, NY (US); Grant J. Palmer, Nashville, TN (US); Paul K. Isbester, Castleton on Hudson, NY (US); Jonathon Salsbury, Madison, WI (US)

(73) Assignee: Kinex Pharmaceuticals, LLC, Buffalo, NY (US)

( * ) Notice: Subject to any disclaimer, the term of this patent is extended or adjusted under 35 U.S.C. 154(b) by 0 days.

(21) Appl. No.: 13/614,063

(22) Filed: Sep. 13, 2012

(65) Prior Publication Data

US 2013/0210822 A1    Aug. 15, 2013

Related U.S. Application Data

(63) Continuation of application No. 13/094,679, filed on Apr. 26, 2011, now Pat. No. 8,309,549, which is a continuation of application No. 12/468,694, filed on May 19, 2009, now Pat. No. 7,935,697, which is a continuation-in-part of application No. 12/154,056, filed on May 19, 2008, now Pat. No. 7,939,529, and a continuation-in-part of application No. 12/005,792, filed on Dec. 28, 2007, now Pat. No. 7,851,470.

(60) Provisional application No. 60/930,758, filed on May 17, 2007, provisional application No. 60/877,762, filed on Dec. 28, 2006.

(51) Int. Cl.
| | | |
|---|---|---|
| *C07D 213/59* | (2006.01) | |
| *A61K 31/44* | (2006.01) | |
| *C07D 213/56* | (2006.01) | |
| *C07D 413/12* | (2006.01) | |

(52) U.S. Cl.
CPC ............ *C07D 213/56* (2013.01); *C07D 213/59* (2013.01); *A61K 31/44* (2013.01); *C07D 413/12* (2013.01)
USPC ....................... 544/131; 514/235.5

(58) Field of Classification Search
CPC .......................... C07D 213/59; A61K 31/4433
USPC ..................... 514/235.5; 544/131
See application file for complete search history.

(56) References Cited

U.S. PATENT DOCUMENTS

| | | | |
|---|---|---|---|
| 3,761,477 A | 9/1973 | Schwartz et al. | |
| 3,868,380 A | 2/1975 | Molteni et al. | |
| 4,010,279 A | 3/1977 | Griss et al. | |
| 5,827,887 A | 10/1998 | Gourvest et al. | |
| 5,849,912 A | 12/1998 | Akasaka et al. | |
| 6,538,960 B1 | 3/2003 | Sabi et al. | |
| 6,624,180 B2 | 9/2003 | South et al. | |
| 6,844,367 B1 | 1/2005 | Zhu et al. | |
| 6,969,726 B2 | 11/2005 | Lou et al. | |
| 7,300,931 B2 | 11/2007 | Hangauer, Jr. | |
| 7,851,470 B2 * | 12/2010 | Hangauer et al. ......... | 514/235.5 |
| 7,935,697 B2 * | 5/2011 | Hangauer et al. ......... | 514/235.5 |
| 7,939,529 B2 * | 5/2011 | Hangauer et al. ......... | 514/235.5 |
| 8,309,549 B2 * | 11/2012 | Hangauer et al. ......... | 514/235.5 |
| 2004/0242572 A1 | 12/2004 | Stenkamp et al. | |
| 2005/0043317 A1 | 2/2005 | Zhou et al. | |
| 2005/0059713 A1 | 3/2005 | Mjalli et al. | |
| 2006/0100245 A1 | 5/2006 | Bakthavatchalam et al. | |
| 2006/0160800 A1 | 7/2006 | Hangauer | |
| 2007/0015752 A1 | 1/2007 | Hangauer | |
| 2007/0197783 A1 | 8/2007 | Hangauer | |
| 2008/0287436 A1 | 11/2008 | Hangauer, Jr. et al. | |
| 2010/0249130 A1 | 9/2010 | Hangauer, Jr. | |

FOREIGN PATENT DOCUMENTS

| | | |
|---|---|---|
| EP | 0463638 A1 | 1/1992 |
| JP | 62252755 A | 11/1987 |
| JP | 2002020362 A | 1/2002 |
| JP | 2003231633 A | 8/2003 |
| WO | WO-9204315 A1 | 3/1992 |
| WO | WO-9219208 A1 | 11/1992 |
| WO | WO-9427949 A1 | 12/1994 |
| WO | WO-9612473 A1 | 5/1996 |
| WO | WO-9821185 A1 | 5/1998 |
| WO | WO-9901127 A1 | 1/1999 |
| WO | WO-0119788 A2 | 3/2001 |
| WO | WO-0156974 A2 | 8/2001 |
| WO | WO-0185726 A1 | 11/2001 |
| WO | WO-0196307 A2 | 12/2001 |

(Continued)

OTHER PUBLICATIONS

An et al. "Oxidation of N-Benzylaldimines to N-Benzylamides by MCPBA and BF3OEt2." *Synlett.* 6(2003):876-878.

(Continued)

*Primary Examiner* — Raymond Henley, III

(74) *Attorney, Agent, or Firm* — Cooley LLP

(57) ABSTRACT

The invention relates to compositions comprising 2-(5-(4-(2-morpholinoethoxy)phenyl)pyridin-2-yl)-N-benzylacetamide and its mesylate and dihydrochloride salts. The invention provides an efficient process for the synthesis of 2-(5-(4-(2-morpholinoethoxy)phenyl)pyridin-2-yl)-N-benzylacetamide and its mesylate and dihydrochloride salts and methods for modulating one or more components of a kinase cascade using the compositions of the invention. The present invention also provides a novel polymorph of the mesylate salt of 2-(5-(4-(2-morpholinoethoxy)phenyl)pyridin-2-yl)-N-benzylacetamide (Form A), characterized by a unique X-ray diffraction pattern and Differential Scanning calorimetry profile, as well as a unique crystalline structure.

10 Claims, 19 Drawing Sheets

(56) References Cited

FOREIGN PATENT DOCUMENTS

| | | |
|---|---|---|
| WO | WO-0198245 A2 | 12/2001 |
| WO | WO-02079197 A1 | 10/2002 |
| WO | WO-03059903 A2 | 7/2003 |
| WO | WO-03078404 A1 | 9/2003 |
| WO | WO-03087057 A1 | 10/2003 |
| WO | WO-03093248 A1 | 11/2003 |
| WO | WO-03093297 A2 | 11/2003 |
| WO | WO-2004011427 A2 | 2/2004 |
| WO | WO-2004011456 A1 | 2/2004 |
| WO | WO-2004043925 A2 | 5/2004 |
| WO | WO-2004056774 A2 | 7/2004 |
| WO | WO-2004078747 A1 | 9/2004 |
| WO | WO-2005013914 A2 | 2/2005 |
| WO | WO-2005032493 A2 | 4/2005 |
| WO | WO-2005097750 A1 | 10/2005 |
| WO | WO-2006071960 A2 | 7/2006 |
| WO | WO-2007026920 A2 | 3/2007 |
| WO | WO-2007095383 A2 | 8/2007 |
| WO | WO-2007136790 A2 | 11/2007 |
| WO | WO-2008002676 A2 | 1/2008 |
| WO | WO-2008082637 A1 | 7/2008 |
| WO | WO-2008127727 A1 | 10/2008 |
| WO | WO-2008127728 A1 | 10/2008 |

OTHER PUBLICATIONS

Bryn et al. "Hydrates and Solvates." *Solid-State Chem. Drugs.* 2nd Ed., SSCI, Inc., IN, Ch. 11. (1999):233-247.

Cain et al. "Potential Antitumor Agents. IX. Bisquaternary Salts." *J. Med. Chem.* 11.5(1968):963-966.

Croteau et al. "Adults with Newly Diagnosed High-Grade Gliomas." *Current Treatment Options in Oncology.* 2(2001):507-515.

Davidson et al. "Discovery and Characterization of a Substrate Selective p38α Inhibitor." *Biochem.* 43(2004):11658-11671.

Duong et al. "Inhibition of Osteoclast Function by Adenovirus Expressing Antisense Protein-Tyrosine Kinase 2." *J. Biol. Chem.* 276.10(2001):7484-7492.

Frame. "Src in Cancer: Deregulation and Consequences for Cell Behaviour." *Biochem. Biophys. Acta.* 1602(2002):114-130.

Garrido et al. "Synthesis of N,N'-Diacyl-1,2-di-(4-pyridylethylethylenediamines." *J. Het. Chem.* 18(1981):1305-1308.

Golub et al. "Molecular Classification of Cancer: Class Discovery and Class Prediction by Gene Expression Monitoring." *Science.* 286(1999):531-537.

Guo et al. "Tyrosine Phosphorylation of the NR2B Subunit of the NMDA Receptor in the Spinal Cord during the Development and Maintenance of Inflammatory Hyperalgesia." *J. Neurosci.* 22.14(2002):6208-6217.

Hadjeri et al. "Antimitotic Activity of 5-Hydroxy-7-methoxy-2-phenyl-4-quinolones." *J. Med. Chem.* 47(2004):4964-4970.

Han. "Advances in Characterization of Pharmaceutical Hydrates." *Trends in Bio/Pharmaceutical Industry.* 3(2006):25-29.

Honma et al. "Antiallergic Agents. 2. N-(1H-Tetrazol-5-yl)-6-phenyl-2-pyridinecarboxamides." *J. Med. Chem.* 26(1983):1499-1504.

Huff. "HIV Protease: A Novel Chemotherapeutic Target for AIDS." *J. Med. Chem.* 34.8(1991):2305-2314.

Lala et al. "Role of Nitric Oxide in Tumor Progression: Lessons from Experimental Tumors." *Cancer Metastasis Rev.* 17.1(1998):91-106.

Lesslie et al. "Combined Activity of Dasatinib (BMS-354825) and Oxaliplatin in an Orthotopic Model of Metastatic Colorectal Carcinoma." *Proc. Amer. Assoc. Cancer Res.* 47(2006). (Abstract #4745).

Liechti et al. "Salicylanilides as Inhibitors of the Protein Tyrosine Kinase Epidermal Growth Factor Receptor." *Eur. J. Med. Chem.* 39.1(2004):11-26.

Million et al. "Inhibition of the EGF-Stimulated Cellular Proliferation of ER 22 Cells by Hydroxybiphenyl Derivatives." *J. Med. Chem.* 38.23(1995):4693-4703.

Miyazaki et al. "Src Kinase Activity is Essential for Osteoclast Function." *J. Biol. Chem.* 279.17(2004):17660-17666.

Parang et al. "Recent Advances in the Discovery of Src Kinase Inhibitors." *Exp. Opin. Ther. Patents.* 15.9(2005):1183-1207.

Paul et al. "Src deficiency or Blockade of Src Activity in Mice Provides Cerebral Protection Following Stroke." *Nat. Med.* 7.2(2001):222-227.

Planas-Silva et al. "Targeting c-Src Kinase Enhances Tamoxifen's Inhibitory Effect on Cell Growth by Modulating Expression of Cell Cycle and Survival Proteins." *Cancer Chemother. Pharmacol.* 60.4(2006):535-543.

Rouhi et al., "The Right Stuff: From Research and Development to the Clinic, Getting Drug Crystals Right is Full of Pitfalls." *Chem. Eng. News.* (2003):32-35.

Stella et al. "Prodrugs: Challenges and Rewards." *Biotechnology: Pharmaceutical Aspects.* New York:Springer-Verlag. 1(2007):24.

U.S. Pharmacopia #23, National Formulary #18. (1995):1843-1844.

Vippagunta et al. "Cyrstalline Solids." *Advanced Drug Delivery Reviews.* 48(2001):3-26.

Yezhelyev et al. "Inhibition of Src Tyrosine Kinase as Treatment for Human Pancreatic Cancer Growing Orthotopically in Nude Mice." *Clin. Cancer Res.* 10(2004):8028-8036.

Yu et al. "Src, a Molecular Switch Governing Gain Control of Synaptic Transmission Mediated by N-methyl-D-aspartate Receptors." *PNAS.* 96(1999):7697-7704.

Zhang et al. "Design, Synthesis, and SAR of Anthranilamide-Based Factor Xa Inhibitors Incorporating Substituted Biphenyl P4 Motifs." *Bioorg. Med. Chem. Lett.* 14.4(2004):983-987.

\* cited by examiner

COMPOSITIONS FOR MODULATING A KINASE CASCADE AND METHODS OF USE THEREOF

RELATED APPLICATIONS

This application claims priority to and is a Continuation application of U.S. application Ser. No. 13/094,679 (now U.S. Pat. No. 8,309,549), filed Apr. 26, 2011, which claims priority to and is a Continuation application of U.S. application Ser. No. 12/468,694 (now U.S. Pat. No. 7,935,697), filed May 19, 2009, which is a Continuation In Part application of U.S. application Ser. No. 12/154,056 (now U.S. Pat. No. 7,939,529), filed May 19, 2008, which claims priority to U.S. provisional application Ser. No. 60/930,758, filed May 17, 2007. U.S. application Ser. No. 12/154,056 is a Continuation In Part application of U.S. application Ser. No. 12/005,792 (now U.S. Pat. No. 7,851,470), filed Dec. 28, 2007, which claims priority to U.S. provisional application Ser. No. 60/877,762, filed Dec. 28, 2006. The entire contents of each application are incorporated by reference herein.

FIELD OF THE INVENTION

The present invention is directed to certain polymorphs of 2-(5-(4-(2-morpholinoethoxy)phenyl)pyridin-2-yl)-N-benzylacetamide mesylate salt (KX2-391.MSA) and compositions and processes for the synthesis of substantially pure 2-(5-(4-(2-morpholinoethoxy)phenyl)pyridin-2-yl)-N-benzylacetamide (KX2-391), and its mesylate and bis-hydrochloride salts. The invention also relates to methods of using such compositions.

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers. In many transduction processes, an increasing number of enzymes and other molecules become engaged in the events that proceed from the initial stimulus. In such cases the chain of steps is referred to as a "signaling cascade" or a "second messenger pathway" and often results in a small stimulus eliciting a large response. One class of molecules involved in signal transduction is the kinase family of enzymes. The largest group of kinases are protein kinases, which act on and modify the activity of specific proteins. These are used extensively to transmit signals and control complex processes in cells.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate, ATP, in a highly conserved pocket. Protein phosphatases catalyze the transfer of phosphate in the opposite direction.

A tyrosine kinase is an enzyme that can transfer a phosphate group from ATP to a tyrosine residue in a protein. Phosphorylation of proteins by kinases is an important mechanism in signal transduction for regulation of enzyme activity. The tyrosine kinases are divided into two groups; those that are cytoplasmic proteins and the transmembrane receptor-linked kinases. In humans, there are 32 cytoplasmic protein tyrosine kinases and 58 receptor-linked protein-tyrosine kinases. The hormones and growth factors that act on cell surface tyrosine kinase-linked receptors are generally growth-promoting and function to stimulate cell division (e.g., insulin, insulin-like growth factor 1, epidermal growth factor).

Inhibitors of various known protein kinases or protein phosphatases have a variety of therapeutic applications. One promising potential therapeutic use for protein kinase or protein phosphatase inhibitors is as anti-cancer agents. About 50% of the known oncogene products are protein tyrosine kinases (PTKs) and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products). There are at least 9 members of the Src family of non-receptor PTKs with pp60$^{c-src}$ (hereafter referred to simply as "Src") being the prototype PTK of the family wherein the approximately 300 amino acid catalytic domains are highly conserved. The hyperactivation of Src has been reported in a number of human cancers, including those of the colon, breast, lung, bladder, and skin, as well as in gastric cancer, hairy cell leukemia, and neuroblastoma. Overstimulated cell proliferation signals from transmembrane receptors (e.g. EGFR and p185HER2/Neu) to the cell interior also appear to pass through Src. Consequently, it has recently been proposed that Src is a universal target for cancer therapy, because hyperactivation (without mutation) is involved in tumor initiation, progression, and metastasis for many important human tumor types.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders.

The compound KX2-391 is a biaryl compound for modulating a kinase cascade and is disclosed in U.S. Pat. No. 7,300,931; U.S. application Ser. No. 11/480,174; and PCT Application No. PCT/2008/004847. The dihydrochloride and mesylate salts of KX2-391 are described in U.S. application Ser. Nos. 12/005,792 and 12/154,056 respectively, including processes for synthesis. The aforementioned patents and applications do not disclose a certain polymorph of KX2-391•MSA with desirable properties related to stability, hygroscopicity, solubility, and crystallinity.

KX2-391 and its salts are useful in methods for modulating a kinase cascade and may be useful for treating or preventing cell proliferation disorders and/or diseases such as hearing loss, osteoporosis, diabetes, eye disease, stroke, atherosclerosis, neuropathic pain, and hepatitis B. Thus, there is an urgent need to discover a form of this compound with desirable physical properties.

SUMMARY OF THE INVENTION

The present invention relates to a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7. The present invention relates to a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ.

The present invention relates to a polymorph of the mesylate salt of 2-(5-(4-(2-morpholinoethoxy)phenyl)pyridin-2-yl)-N-benzylacetamide (Form A) characterized by a Differential Scanning Calorimetry (DSC) thermogram having a single maximum value at about 164, as measured by a Mettler 822$^e$ DSC instrument. In one aspect, the invention relates to a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7 and further characterized by a Differential Scanning Calorimetry (DSC) thermogram having a single maximum value at about 164, as measured by a Mettler 822$^e$ DSC instrument. In one aspect, the invention relates to a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ and further characterized by a Differential Scanning Calorimetry (DSC) thermogram having a single maximum value at about 164, as measured by a Mettler 822$^e$ DSC instrument.

The present invention relates to a pharmaceutical composition comprising a polymorph of the mesylate salt of 2-(5-(4-(2-morpholinoethoxy)phenyl)pyridin-2-yl)-N-benzylacetamide (Form A) and a pharmaceutically acceptable excipient or carrier.

The present invention relates to a method of treating or preventing disease or condition in a subject in need thereof, said method comprising the step of administering to said subject a pharmaceutical composition of the invention, wherein said disease or condition is selected from cancer, hearing loss, osteoporosis, obesity, diabetes, ophthalmic diseases, stroke, atherosclerosis, neuropathic pain, hepatitis B, autoimmune disease.

The present invention relates to a process for preparing the polymorph of the mesylate salt of 2-(5-(4-(2-morpholinoethoxy)phenyl)pyridin-2-yl)-N-benzylacetamide (Form A) comprising the step of adding methanesulfonic acid to 2-(5-(4-(2-morpholinoethoxy)phenyl)pyridin-2-yl)-N-benzylacetamide in acetone. In one aspect, the process comprises an amount of said acetone that is greater than 64 volumes.

DETAILED DESCRIPTION OF THE INVENTION

Figure 1:
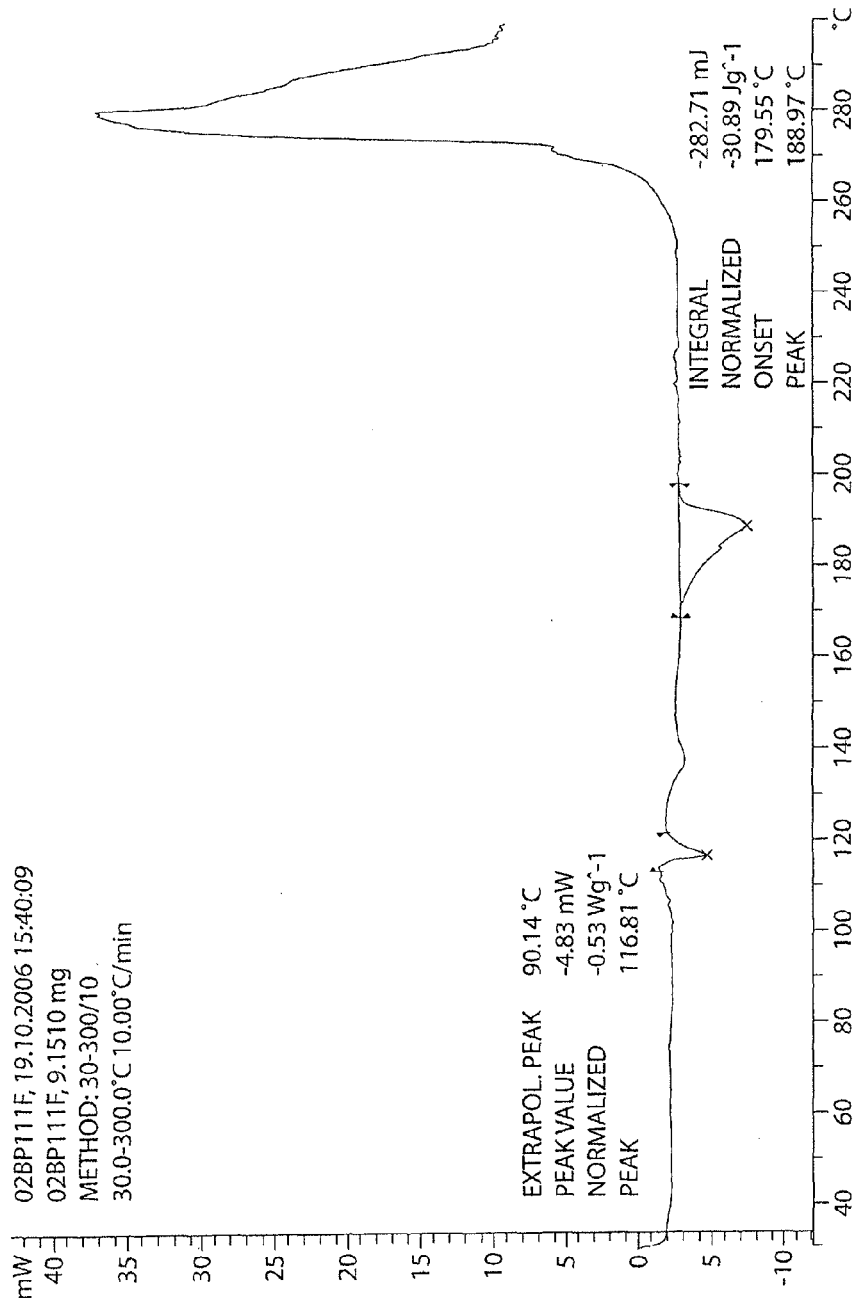
FIG. 1 is a graph indicating the DSC of KX2-391•2HCl lot 02BP111F.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control. All publications, patent applications, patents, and other references mentioned herein are incorporated by reference in their entirety.

Preparation of KX2-391 and its Salts

The synthesis of 4-(2-(4-(6-fluoropyridin-3-yl)phenoxy) ethyl)morpholine is shown in the scheme below:

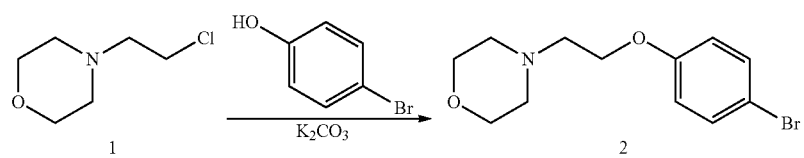

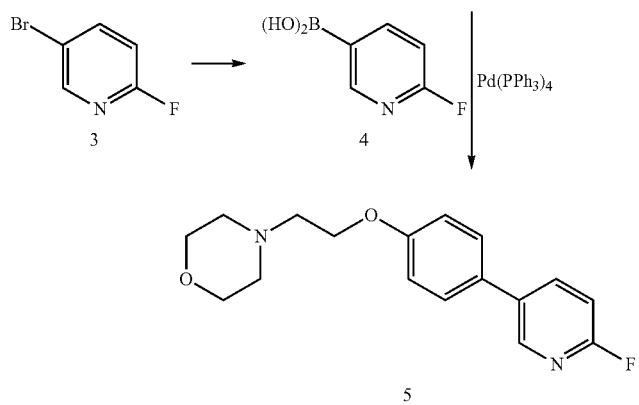

4-(2-(4-(6-fluoropyridin-3-yl)phenoxy)ethyl)morpholine (5) was synthesized in 3 steps. Intermediate 2 was synthesized using an ether coupling reaction e.g., using Williamson ether synthesis. Ether formation between 4-(2-chloroethyl) morpholine (1) and 4-bromophenol was carried out in the presence of potassium carbonate and DMF to afford 4-(2-(4-bromophenoxy)ethyl)morpholine (2). Rigorously dry conditions were not essential for this reaction and a basic wash with sodium hydroxide was used to remove any remaining 4-bromophenol. In another aspect of the invention, intermediate 2 is synthesized using any ether formation reaction. Intermediate 2 is synthesized starting from compound 1 containing any leaving group. For example, the skilled chemist would start with compounds of the general formula:

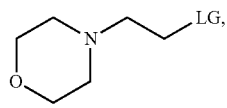

wherein the leaving group "LG" includes but is not limited to halogen, tosylate, mesylate, trifluate, etc.

Compound 5 was formed using a Suzuki reaction. Formation of the aryl borate, 6-fluoropyridin-3-yl-3-boronic acid (4), was carried out by forming the aryl anion using n-BuLi followed by in situ quenching with triisopropylborate (Li, et al., *J. Org. Chem.* 2002, 67, 5394-5397). The resulting 6-fluoropyridin-3-yl-3-boronic acid (4) was coupled to 4-(2-(4-bromophenoxy)ethyl)morpholine (2) in a solution of DME and aqueous sodium carbonate using tetrakis(triphenylphosphine)palladium to afford 4-(2-(4-(6-fluoropyridin-3-yl)phenoxy)ethyl)morpholine (5), which was purified using silica gel chromatography. The skilled chemist would know that other transition metal coupling reaction are used to prepare compound 5.

The synthesis of 2-(5-(4-(2-morpholinoethoxy)phenyl)pyridin-2-yl)-N-benzylacetamide dihydrochloride is shown below:

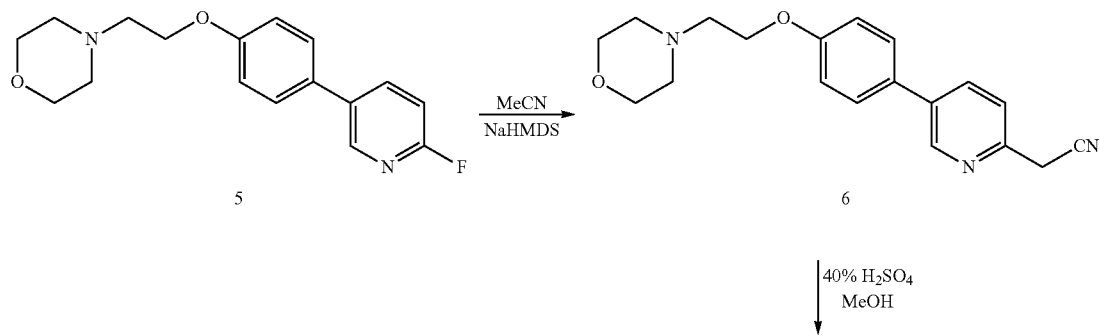

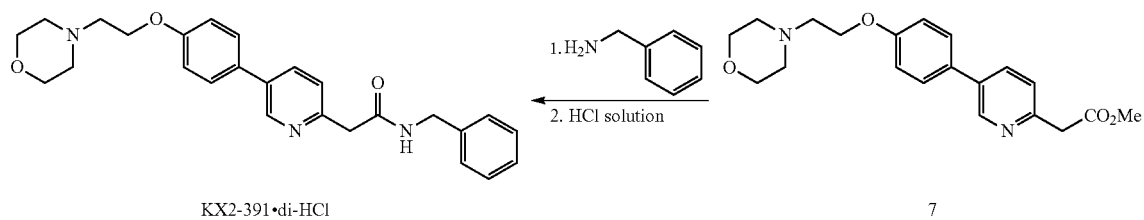

KX2-391•di-HCl

7

2-(5-(4-(2-morpholinoethoxy)phenyl)pyridin-2-yl)-N-benzylacetamide dihydrochloride (KX2-391•HCl) was synthesized in four linear steps. The fluoride of 4-(2-(4-(6-fluoropyridin-3-yl)phenoxy)ethyl)morpholine (5) was displaced by the anion of acetonitrile formed using commercially available NaHMDS. Acetonitrile was added slowly to a cooled mixture of compound 5 and base to form 2-(5-(4-(2-morpholinoethoxy)phenyl)pyridin-2-yl)acetonitrile (6). In another aspect of the invention, intermediate 5 may have a leaving group other than fluorine. Thus, compounds of the general formula:

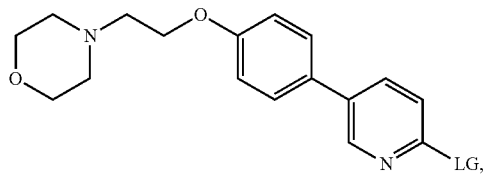

would be pursued where LG includes other leaving groups known to the skilled chemist.

Acid catalyzed methanolysis of 2-(5-(4-(2-morpholinoethoxy)phenyl)pyridin-2-yl)acetonitrile (6) was carried out using a mixture of concentrated sulfuric and fuming sulfuric acid. The use of fuming sulfuric acid removed residual water from the reaction mixture and reduced the amount of carboxylic acid by-product formed. The reaction mixture was quenched by adding the reaction mixture to a solution of saturated sodium bicarbonate and dichloromethane while maintaining the temperature below 20° C. Any carboxylic acid contaminant was readily removed with aqueous work-up. In another aspect of the invention, other acid catalyzed conditions are used by the skilled artisan for alcoholysis of the nitrile of compound 6 to produce compound 7.

The resulting methyl 2-(5-(4-(2-morpholinoethoxy)phenyl)pyridin-2-yl)acetate (7) and benzyl amine were coupled in anisole at high temperature to afford 2-(5-(4-(2-morpholinoethoxy)phenyl)pyridin-2-yl)-N-benzylacetamide (KX2-391). An HCl solution formed by adding acetyl chloride to absolute ethanol was added to KX2-391 to form the bis-HCl salt, 2-(5-(4-(2-morpholinoethoxy)phenyl)pyridin-2-yl)-N-benzylacetamide dihydrochloride, (KX2-di-HCl).

The synthesis of the mesylate salt of KX2-391 (KX2-391•MSA) is depicted in the scheme below:

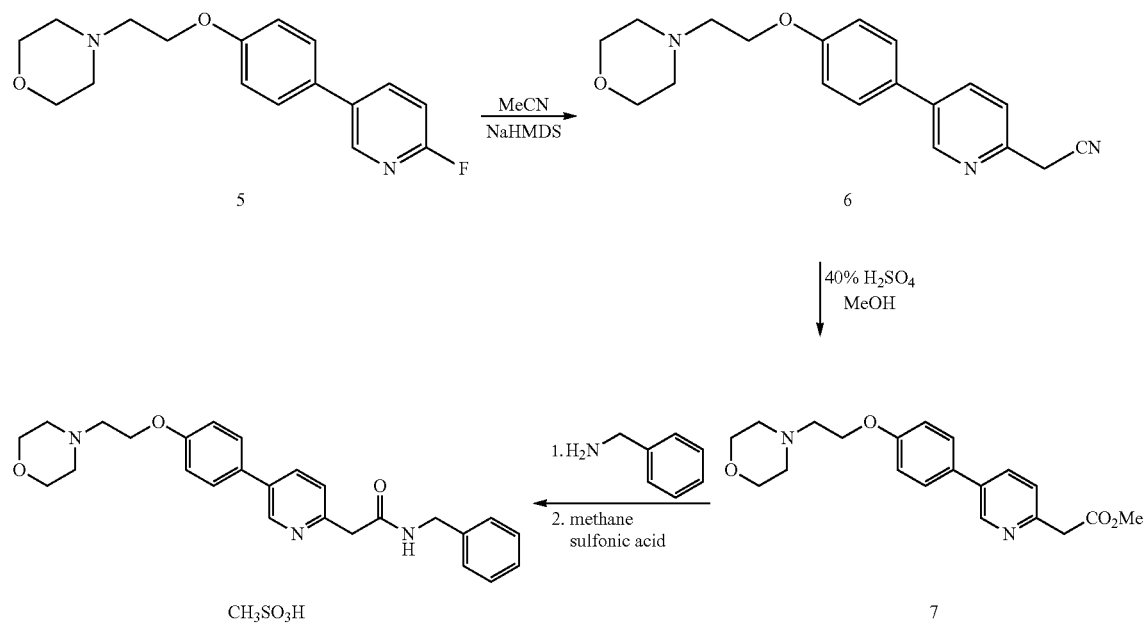

2-(5-(4-(2-morpholinoethoxy)phenyl)pyridin-2-yl)-N-benzylacetamide mesylate (KX2-391•MSA) was synthesized in four linear steps starting from compound 5. The first 3 steps were carried out similar to the procedure discussed above for KX2-391•2HCl to afford methyl 2-(5-(4-(2-morpholinoethoxy)phenyl)pyridin-2-yl)acetate (KX2-391). KX2-391 was converted to the methanesulfonate salt by treatment with methanesulfonic acid (MSA) in acetone at 50° C. to afford 2-(5-(4-(2-morpholinoethoxy)phenyl)pyridin-2-yl)-N-benzylacetamide mesylate (KX2-391•MSA).

In another aspect of the invention, intermediate 7 can be synthesized having a group other than —C(O)OMe. The skilled chemist would pursue intermediate compounds of the general formula:

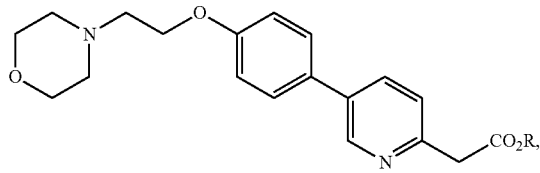

wherein the group "R" includes but is not limited to hydrogen and alkyl.

In one aspect, the invention relates to a process for preparing 2-(5-(4-(2-morpholinoethoxy)phenyl)pyridin-2-yl)-N-benzylacetamide comprising the steps of: reacting 4-(2-chloroethyl)morpholine with 4-bromophenol to yield 4-(2-(4-bromophenoxy)ethyl)morpholine; (2) coupling 4-(2-(4-bromophenoxy)ethyl)morpholine with 6-fluoropyridin-3-yl-3-boronic acid to yield 4-(2-(4-(6-fluoropyridin-3-yl)phenoxy)ethyl)morpholine; reacting 4-(2-(4-(6-fluoropyridin-3-yl)phenoxy)ethyl)morpholine with acetonitrile to yield 2-(5-(4-(2-morpholinoethoxy)phenyl)pyridin-2-yl)acetonitrile; (4) converting 2-(5-(4-(2-morpholinoethoxy)phenyl)pyridin-2-yl)acetonitrile to methyl 2-(5-(4-(2-morpholinoethoxy)phenyl)pyridin-2-yl)acetate; and (5) reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide.

In another aspect the invention relates to a process for preparing 2-(5-(4-(2-morpholinoethoxy)phenyl)pyridin-2-yl)-N-benzylacetamide mesylate comprising the steps of: (1) reacting 4-(2-chloroethyl)morpholine with 4-bromophenol to yield 44244-bromophenoxy)ethyl)morpholine; (2) coupling 4-(2-(4-bromophenoxy)ethyl)morpholine with 6-fluoropyridin-3-yl-3-boronic acid to yield 4-(2-(4-(6-fluoropyridin-3-yl)phenoxy)ethyl)morpholine; (3) reacting 4-(2-(4-(6-fluoropyridin-3-yl)phenoxy)ethyl)morpholine with acetonitrile to yield 2-(5-(4-(2-morpholinoethoxy)phenyl)pyridin-2-yl)acetonitrile; (4) converting 2-(5-(4-(2-morpholinoethoxy)phenyl)pyridin-2-yl)acetonitrile to methyl 2-(5-(4-(2-morpholinoethoxy)phenyl)pyridin-2-yl)acetate; (5) reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide; and (6) contacting 2-(5-(4-(2-morpholinoethoxy)phenyl)pyridin-2-yl)-N-benzylacetamide with methane sulfonic acid to yield 2-(5-(4-(2-morpholinoethoxy)phenyl)pyridin-2-yl)-N-benzylacetamide mesylate.

In another aspect, the invention relates to a process for preparing 2-(5-(4-(2-morpholinoethoxy)phenyl)pyridin-2-yl)-N-benzylacetamide mesylate comprising the step of contacting 2-(5-(4-(2-morpholinoethoxy)phenyl)pyridin-2-yl)-N-benzylacetamide with methane sulfonic acid to yield 2-(5-(4-(2-morpholinoethoxy)phenyl)pyridin-2-yl)-N-benzylacetamide mesylate.

In another aspect, the invention relates to a process for preparing 2-(5-(4-(2-morpholinoethoxy)phenyl)pyridin-2-yl)-N-benzylacetamide dihydrochloride comprising the steps of: (1) reacting 4-(2-chloroethyl)morpholine with 4-bromophenol to yield 4-(2-(4-bromophenoxy)ethyl)morpholine; (2) coupling 4-(2-(4-bromophenoxy)ethyl)morpholine with 6-fluoropyridin-3-yl-3-boronic acid to yield 4-(2-(4-(6-fluoropyridin-3-yl)phenoxy)ethyl)morpholine; (3) reacting 4-(2-(4-(6-fluoropyridin-3-yl)phenoxy)ethyl)morpholine with acetonitrile to yield 2-(5-(4-(2-morpholinoethoxy)phenyl)pyridin-2-yl)acetonitrile; (4) converting 2-(5-(4-(2-morpholinoethoxy)phenyl)pyridin-2-yl)acetonitrile to methyl 2-(5-(4-(2-morpholinoethoxy)phenyl)pyridin-2-yl)acetate; (5) reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide; and (6) contacting 2-(5-(4-(2-morpholinoethoxy)phenyl)pyridin-2-yl)-N-benzylacetamide with hydrochloric acid to yield 2-(5-(4-(2-morpholinoethoxy)phenyl)pyridin-2-yl)-N-benzylacetamide dihydrochloride.

In another aspect, the invention relates to a process for preparing 2-(5-(4-(2-morpholinoethoxy)phenyl)pyridin-2-yl)-N-benzylacetamide dihydrochloride comprising the step of contacting 2-(5-(4-(2-morpholinoethoxy)phenyl)pyridin-2-yl)-N-benzylacetamide with hydrochloric acid to yield 2-(5-(4-(2-morpholinoethoxy)phenyl)pyridin-2-yl)-N-benzylacetamide dihydrochloride.

In another aspect, the invention relates to a process for preparing 2-(5-(4-(2-morpholinoethoxy)phenyl)pyridin-2-yl)-N-benzylacetamide comprising the step of reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide.

In another aspect, the invention relates to the process for preparing 2-(5-(4-(2-morpholinoethoxy)phenyl)pyridin-2-yl)-N-benzylacetamide comprising the steps of converting 2-(5-(4-(2-morpholinoethoxy)phenyl)pyridin-2-yl)acetonitrile to methyl 2-(5-(4-(2-inorpholinoethoxy)phenyl)pyridin-2-yl)acetate; and reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide.

In another aspect, the invention relates to the process for preparing 2-(5-(4-(2-morpholinoethoxy)phenyl)pyridin-2-yl)-N-benzylacetamide comprising the steps of reacting 4-(2-(4-(6-fluoropyridin-3-yl)phenoxy)ethyl)morpholine with acetonitrile to yield 2-(5-(4-(2-morpholinoethoxy)phenyl)pyridin-2-yl)acetonitrile; converting 2-(5-(4-(2-morpholinoethoxy)phenyl)pyridin-2-yl)acetonitrile to methyl 2-(5-(4-(2-morpholinoethoxy)phenyl)pyridin-2-yl)acetate; and reacting methyl 2-(5-(4-(2-morpholinoethoxy)phenyl)pyridin-2-yl)acetate with benzylamine to yield 2-(5-(4-(2-morpholinoethoxy)phenyl)pyridin-2-yl)-N-benzylacetamide.

In another aspect, the invention relates to the process for preparing 2-(5-(4-(2-morpholinoethoxy)phenyl)pyridin-2-yl)-N-benzylacetamide comprising the steps of coupling 4-(2-(4-bromophenoxy)ethyl)morpholine with 6-fluoropyridin-3-yl-3-boronic acid to yield 4-(2-(4-(6-fluoropyridin-3-yl)phenoxy)ethyl)morpholine; reacting 4-(2-(4-(6-fluoropyridin-3-yl)phenoxy)ethyl)morpholine with acetonitrile to yield 2-(5-(4-(2-morpholinoethoxy)phenyl)pyridin-2-yl)acetonitrile; converting 2-(5-(4-(2-morpholinoethoxy)phenyl)pyridin-2-yl)acetonitrile to methyl 2-(5-(4-(2-morpholinoethoxy)phenyl)pyridin-2-yl)acetate; and reacting methyl 2-(5-

(4-(2-morpholinoethoxy)phenyl)pyridin-2-yl)acetate with benzylamine to yield 2-(5-(4-(2-morpholinoethoxy)phenyl) pyridin-2-yl)-N-benzylacetamide.

In another aspect, the invention relates to a process for preparing 2-(5-(4-(2-morpholinoethoxy)phenyl)pyridin-2-yl)-N-benzylacetamide comprising the step of reacting 4-(2-chloroethyl)morpholine with 4-bromophenol to yield 44244-bromophenoxy)ethyl)morpholine.

In another aspect, the invention relates to a process for preparing 2-(5-(4-(2-morpholinoethoxy)phenyl)pyridin-2-yl)-N-benzylacetamide comprising the step of coupling 4-(2-(4-bromophenoxy)ethyl)morpholine with 6-fluoropyridin-3-yl-3-boronic acid to yield 4-(2-(4-(6-fluoropyridin-3-yl) phenoxy)ethyl)morpholine.

In another aspect, the invention relates to a process for preparing 2-(5-(4-(2-morpholinoethoxy)phenyl)pyridin-2-yl)-N-benzylacetamide comprising the step of reacting 4-(2-(4-(6-fluoropyridin-3-yl)phenoxy)ethyl)morpholine with acetonitrile to yield 2-(5-(4-(2-morpholinoethoxy)phenyl) pyridin-2-yl)acetonitrile.

In another aspect, the invention relates to a process for preparing 2-(5-(4-(2-morpholinoethoxy)phenyl)pyridin-2-yl)-N-benzylacetamide comprising the steps of converting 2-(5-(4-(2-morpholinoethoxy)phenyl)pyridin-2-yl)acetonitrile to methyl 2-(5-(4-(2-morpholinoethoxy)phenyl)pyridin-2-yl)acetate.

In another aspect, the invention relates to the process described above for KX2-391 for preparing 2-(5-(4-(2-morpholinoethoxy)phenyl)pyridin-2-yl)-N-benzylacetamide mesylate comprising the step of: contacting 2-(5-(4-(2-morpholinoethoxy)phenyl)pyridin-2-yl)-N-benzylacetamide with methane sulfonic acid to yield 2-(5-(4-(2-morpholinoethoxy)phenyl)pyridin-2-yl)-N-benzylacetamide mesylate.

In another aspect, the invention relates to the process described above for KX2-391 for preparing 2-(5-(4-(2-morpholinoethoxy)phenyl)pyridin-2-yl)-N-benzylacetamide dihydrochloride comprising the step of contacting 2-(5-(4-(2-morpholinoethoxy)phenyl)pyridin-2-yl)-N-benzylacetamide with hydrochloric acid to yield 2-(5-(4-(2-morpholinoethoxy)phenyl)pyridin-2-yl)-N-benzylacetamide dihydrochloride.

In one aspect, the invention relates to a polymorph of the mesylate salt of 2-(5-(4-(2-morpholinoethoxy)phenyl)pyridin-2-yl)-N-benzylacetamide prepared by a process described herein and further produced by a purification process comprising the step of recrystallizing a crude preparation of said salt from acetone. In another aspect, the polymorph is produced by a purification process, wherein the amount of said acetone used is 80 volumes.

Compositions

The invention relates to substantially pure 2-(5-(4-(2-morpholinoethoxy)phenyl)pyridine-2-yl)-N-benzylacetamide (KX2-391), and salts, solvates, hydrates, or prodrugs thereof:

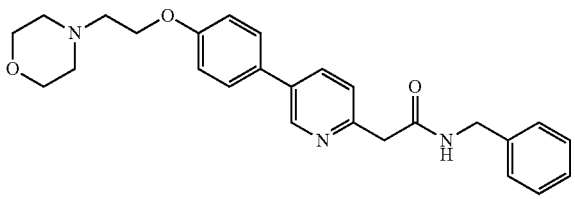 [SMILES: O=C(Cc1ccc(-c2ccc(OCCN3CCOCC3)cc2)cn1)NCc1ccccc1]

(KX2-391). Other names for the compound KX2-391 include 2-(5-(4-(2-morpholinoethoxy)phenyl)pyridin-2-yl)-N-benzylacetamide and KX2-391 free base.

The invention relates to compositions and processes for the synthesis of highly purified KX2-391 (>98.0% as determined by HPLC) which is safe and simple and which produces KX2-391 on a large scale (>100 g). Preferably the synthesis produces the compound in high yield (>80%) and with limited impurities.

In preferred embodiments, KX2-391 in the compositions of the instant invention has a purity of greater than 98%. For example, the purity of KX2-391 in the compositions of the invention is 98.5%, 99.0%, 99.5%, 99.6%, 99.7%, 99.8% or 99.9%.

In preferred embodiments, the compositions and formulations of the invention contain less than 2% impurities. For example, the compositions and formulations of the invention contain less than 2% of any one of the following impurities, or combinations thereof: ethyl chloride, ethanol, ethyl acetate, heptane, anisole, and palladium.

Some impurities are measured in parts per million, which is a relative weight measurement equal to weight of solute/ weight of solution ×1,000,000, for example, the weight of ethyl chloride/weight of KX2-391 di-HCl sample ×1,000,000; for example, the weight of ethyl chloride/weight of KX2-391 mesylate sample ×1,000,000.

In other preferred embodiments the composition contains less than 250 ppm ethyl chloride as determined by headspace gas chromatography residual solvent analysis. In an embodiment, the compounds and formulations of the present invention contain ethyl chloride in a range from about 0 ppm to about 250 ppm (or any value within said range). For example, the compositions contain less than 200 ppm, less than 200 ppm, less than 150 ppm, less than 100 ppm, or less than 50 ppm ethyl chloride.

The compounds, salts and formulations of the present invention contain less than about 100 ppm palladium. In an embodiment, the compounds, salts and formulations of the present invention contain palladium in a range from about 0 ppm to about 100 ppm (or any value within said range). For example, the compositions contain less than 75 ppm, less than 50 ppm, less than 30 ppm, less than 20 ppm, less than 10 ppm, or less than 5 ppm palladium.

In an embodiment, the compounds, salts and formulations of the present invention contain ethanol in a range from about 0 ppm to about 5000 ppm (or any value within said range). For example, the compositions contain less than 4500 ppm, less than 4000 ppm, less than 3500 ppm, less than 3000 ppm, less than 2500 ppm, or less than 2000 ppm ethanol.

In an embodiment, the compounds, salts and formulations of the present invention contain ethyl acetate in a range from about 0 ppm to about 50,000 ppm (or any value within said range). For example, the compositions contain less than 48,000 ppm, less than 45,000 ppm, less than 40,000 ppm, less than 35,000 ppm, less than 30,000 ppm, or less than 25,000 ppm ethyl acetate.

In an embodiment, the compounds, salts and formulations of the present invention contain heptane in a range from about 0 ppm to about 7,500 ppm (or any value within said range). For example, the compositions contain less than 7,000 ppm, less than 6,500 ppm, less than 6,000 ppm, less than 5,000 ppm, less than 3,000 ppm, or less than 1,000 ppm heptane.

In an embodiment, the compounds, salts and formulations of the present invention contain anisole in a range from about 0 ppm to about 100 ppm (or any value within said range). For example, the compositions contain less than 80 ppm, less than 75 ppm, less than 50 ppm, less than 25 ppm, less than 10 ppm, or less than 5 ppm anisole.

The invention relates to a composition that includes a substantially pure solvate of KX2-391.

The invention also relates to a composition that includes a substantially pure hydrate of KX2-391.

The invention also includes a substantially pure acid addition salt of KX2-391. For example, a hydrochloride salt. The acid addition salt can be, for example, a dihydrochloride salt. For example, the acid addition salt can be, for example, a mesylate salt.

The invention relates to a composition that includes a substantially pure acid addition salt of KX2-391.

The invention relates to a composition that includes a substantially pure hydrochloride salt KX2-391. The invention relates to a composition that includes a substantially pure dihydrochloride salt of KX2-391.

The invention relates to a composition that includes a substantially pure mesylate salt of KX2-391.

The invention also includes a prodrug of KX2-391.

The invention also includes a substantially pure, pharmaceutically acceptable salt of KX2-391.

The invention also relates to a composition that includes substantially pure KX2-391 or a solvate, hydrate, or salt thereof, and at least one pharmaceutically acceptable excipient.

The invention relates to substantially pure 2-(5-(4-(2-morpholinoethoxy)phenyl)pyridine-2-yl)-N-benzylacetamide dihydrochloride:

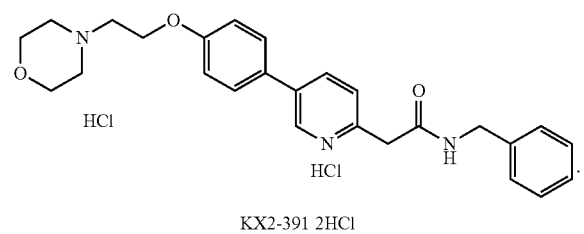 [SMILES: O=C(Cc1ccc(-c2ccc(OCCN3CCOCC3)cc2)cn1)NCc1ccccc1 ; Cl ; Cl]

KX2-391 2HCl

The invention relates to compositions and processes for the synthesis of highly purified KX2-391•2HCl or KX2-391•MSA (>98.0% as determined by HPLC) which is safe and simple and which produces KX2-391•2HCl or KX2-391•MSA respectively, on a large scale (>100 g) in high yield (>80%) and with limited ethyl chloride (<250 ppm ethyl chloride as determined by headspace gas chromatography residual solvent analysis).

In preferred embodiments, KX2-391•2HCl in the compositions of the instant invention has a purity of greater than 98%. For example, the purity of KX2-391•2HCl in the compositions of the invention is 98.5%, 99.0%, 99.5%, 99.6%, 99.7%, 99.8% or 99.9%.

In preferred embodiments, the compositions and formulations of the invention contain less than 2% impurities. For example, the compositions and formulations of the invention contain less than 2% of any one of the following impurities, or combinations thereof: ethyl chloride, ethanol, ethyl acetate, heptane, anisole, and palladium.

In other preferred embodiments the composition contains less than 250 ppm ethyl chloride as determined by headspace gas chromatography residual solvent analysis. In an embodiment, the compounds, salts and formulations of the present invention contain ethyl chloride in a range from about 0 ppm to about 250 ppm (or any value within said range). For example, the compositions contain less than 200 ppm, less than 200 ppm, less than 150 ppm, less than 100 ppm, or less than 50 ppm ethyl chloride.

The compounds, salts and formulations of the present invention contain less than about 100 ppm palladium. In an embodiment, the compounds, salts and formulations of the present invention contain palladium in a range from about 0 ppm to about 100 ppm (or any value within said range). For example, the compositions contain less than 75 ppm, less than 50 ppm, less than 30 ppm, less than 20 ppm, less than 10 ppm, or less than 5 ppm palladium.

The invention also relates to a composition that includes substantially pure KX2-391•2HCl and at least one pharmaceutically acceptable excipient.

The invention relates to substantially pure 2-(5-(4-(2-morpholinoethoxy)phenyl)pyridine-2-yl)-N-benzylacetamide mesylate (KX2-391•MSA):

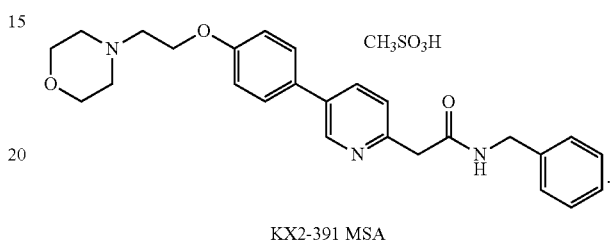

KX2-391 MSA

The invention relates to compositions and processes for the synthesis of highly purified KX2-391•MSA (>98.0% as determined by HPLC) which is safe and simple and which produces KX2-391•MSA on a large scale (>100 g) in high yield (>80%) and with limited ethyl chloride (<250 ppm ethyl chloride as determined by headspace gas chromatography residual solvent analysis).

In preferred embodiments, KX2-391•MSA in the compositions of the instant invention has a purity of greater than 98%. For example, the purity of KX2-391•MSA in the compositions of the invention is 98.5%, 99.0%, 99.5%, 99.6%, 99.7%, 99.8% or 99.9%.

In preferred embodiments, the compositions and formulations of the invention contain less than 2% impurities. For example, the compositions and formulations of the invention contain less than 2% of any one of the following impurities, or combinations thereof: ethyl chloride, ethanol, ethyl acetate, heptane, anisole, and palladium.

In other preferred embodiments the composition contains less than 250 ppm ethyl chloride as determined by headspace gas chromatography residual solvent analysis. In an embodiment, the compounds, salts and formulations of the present invention contain ethyl chloride in a range from about 0 ppm to about 250 ppm (or any value within said range). For example, the compositions contain less than 200 ppm, less than 200 ppm, less than 150 ppm, less than 100 ppm, or less than 50 ppm ethyl chloride.

The compounds, salts and formulations of the present invention contain less than about 100 ppm palladium. In an embodiment, the compounds, salts and formulations of the present invention contain palladium in a range from about 0 ppm to about 100 ppm (or any value within said range). For example, the compositions contain less than 75 ppm, less than 50 ppm, less than 30 ppm, less than 20 ppm, less than 10 ppm, or less than 5 ppm palladium.

The invention also relates to a composition that includes substantially pure KX2-391•MSA and at least one pharmaceutically acceptable excipient.

The invention relates to substantially pure 2-(5-(4-(2-morpholinoethoxy)phenyl)pyridine-2-yl)-N-benzylacetamide mesylate (KX2-391•MSA), Form A:

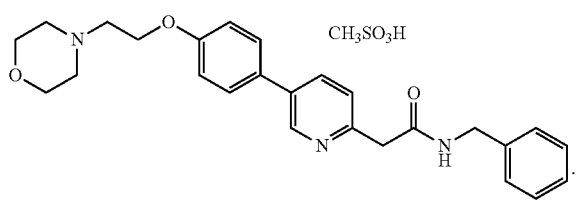

KX2-391 MSA, Form A

The invention relates to compositions and processes for the synthesis of highly purified KX2-391•MSA, Form A (>98.0% as determined by HPLC) which is safe and simple and which produces KX2-391•MSA, Form A on a large scale (>100 g) in high yield (>80%) and with limited ethyl chloride (<250 ppm ethyl chloride as determined by headspace gas chromatography residual solvent analysis).

In preferred embodiments, KX2-391•MSA, Form A in the compositions of the instant invention has a purity of greater than 98%. For example, the purity of KX2-391•MSA, Form A in the compositions of the invention is 98.5%, 99.0%, 99.5%, 99.6%, 99.7%, 99.8% or 99.9%.

In preferred embodiments, the compositions and formulations of the invention contain less than 2% impurities. For example, the compositions and formulations of the invention contain less than 2% of any one of the following impurities, or combinations thereof: ethyl chloride, ethanol, ethyl acetate, heptane, anisole, and palladium.

In other preferred embodiments the composition contains less than 250 ppm ethyl chloride as determined by headspace gas chromatography residual solvent analysis. In an embodiment, the compounds, salts and formulations of the present invention contain ethyl chloride in a range from about 0 ppm to about 250 ppm (or any value within said range). For example, the compositions contain less than 200 ppm, less than 200 ppm, less than 150 ppm, less than 100 ppm, or less than 50 ppm ethyl chloride.

The compounds, salts and formulations of the present invention contain less than about 100 ppm palladium. In an embodiment, the compounds, salts and formulations of the present invention contain palladium in a range from about 0 ppm to about 100 ppm (or any value within said range). For example, the compositions contain less than 75 ppm, less than 50 ppm, less than 30 ppm, less than 20 ppm, less than 10 ppm, or less than 5 ppm palladium.

The invention also relates to a composition that includes substantially pure KX2-391•MSA, Form A and at least one pharmaceutically acceptable excipient.

Certain compounds and salts of the invention are non-ATP competitive kinase inhibitors.

For example, the compounds of the invention or salts thereof are useful to treat or prevent a microbial infection, such as a bacterial, fungal, parasitic or viral infection.

A compound of the invention or salt thereof may be used as a pharmaceutical agent. For example, a compound of the invention or salt thereof is used as an anti-proliferative agent, for treating humans and/or animals, such as for treating humans and/or other mammals.

The compounds or salts may be used without limitation, for example, as anti-cancer, anti-angiogenesis, anti-microbial, anti-bacterial, anti-fungal, anti-parasitic and/or anti-viral agents. Additionally, the compounds or salts may be used for other cell proliferation-related disorders such as diabetic retinopathy, macular degeneration and psoriases. Anti-cancer agents include anti-metastatic agents.

The compound of the invention or salt thereof used as a pharmaceutical agent may be, for example, substantially pure KX2-391, KX2-391•2HCl, KX2-391•MSA, or KX2-391•MSA, Form A.

The present invention provides compositions and formulations which contain limited impurities. The compounds, salts and formulations of the present invention have a purity greater than about 98.0% as determined by known methods in the art, for example, HPLC. In an embodiment, the compounds, salts and formulations of the present invention have a purity ranging from about 99.0% to about 100% (or any value within said range). For example, such compounds, salts, compositions, or formulations can have a purity of 98.1%, 98.2%, 98.3%, 98.4%, 98.5%, 98.6%, 98.7%, 98.8%, 98.9%, 99.0%, 99.1%, 99.2%, 99.3, 99.4%, 99.5%, 99.6%, 99.7%, 99.8%, or 99.9%.

In order to elicit the maximum pharmacodynamic and therapeutic effect of the compositions and formulations of the present invention, it is beneficial to limit the levels of impurities such as ethyl chloride and palladium. These impurities can result in undesirable toxicity.

In preferred embodiments, the compositions and formulations of the invention contain less than 2% impurities. For example, the compositions and formulations of the invention contain less than 2% of any one of the following impurities, or combinations thereof: ethyl chloride, ethanol, ethyl acetate, heptane, anisole, and palladium.

In other preferred embodiments the composition contains less than 250 ppm ethyl chloride as determined by headspace gas chromatography residual solvent analysis. In an embodiment, the compounds and formulations of the present invention contain ethyl chloride in a range from about 0 ppm to about 250 ppm (or any value within said range). For example, the compositions contain less than 200 ppm, less than 200 ppm, less than 150 ppm, less than 100 ppm, or less than 50 ppm ethyl chloride.

The compounds, salts and formulations of the present invention contain less than about 100 ppm palladium. In an embodiment, the compounds, salts and formulations of the present invention contain palladium in a range from about 0 ppm to about 100 ppm (or any value within said range). For example, the compositions contain less than 75 ppm, less than 50 ppm, less than 30 ppm, less than 20 ppm, less than 10 ppm, or less than 5 ppm palladium.

Polymorph Compositions

Figure 7:
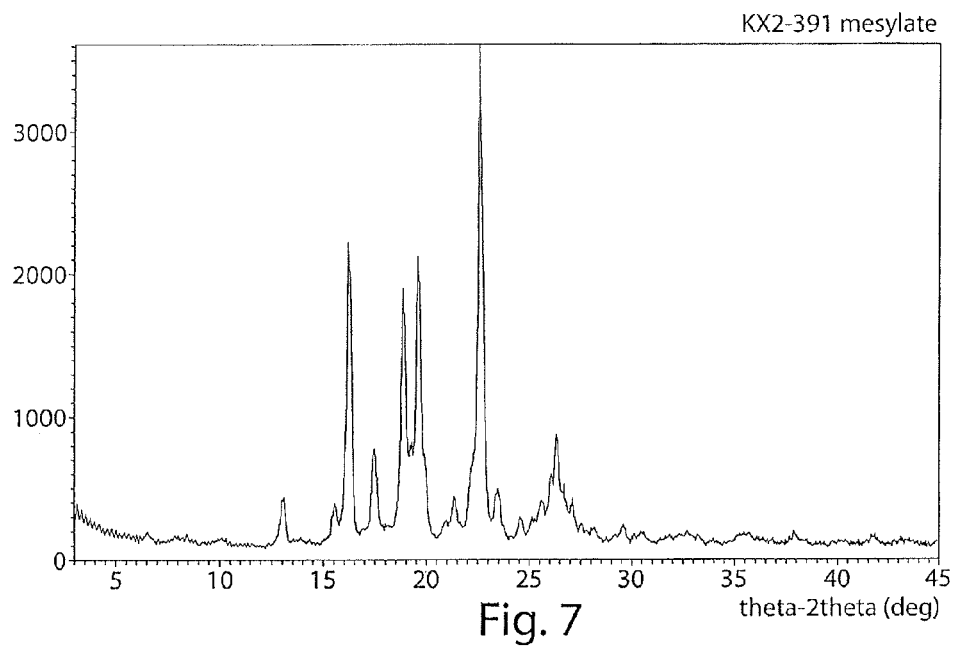
FIG. 7 is a graph indicating the XRPD of KX2-391•MSA, Form A (lot GJP-S10(1)).

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7.

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ.

In one aspect the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ.

In one aspect, the polymorph of the invention is characterized by an X-ray diffraction pattern measured by Cu Kα radiation.

In one aspect, the invention includes a polymorph of the mesylate salt of 2-(5-(4-(2-morpholinoethoxy)phenyl)pyridin-2-yl)-N-benzylacetamide (Form A) characterized by a Differential Scanning Calorimetry (DSC) thermogram having a single maximum value at about 164.

In one aspect, the polymorph of the invention is characterized by a DSC thermogram as measured by a Mettler 822$^e$ DSC instrument.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7 and by a Differential Scanning Calorimetry (DSC) thermogram having a single maximum value at about 164.

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ and by a Differential Scanning Calorimetry (DSC) thermogram having a single maximum value at about 164.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ and by a Differential Scanning Calorimetry (DSC) thermogram having a single maximum value at about 164.

In one aspect, the invention includes a polymorph of the mesylate salt of 2-(5-(4-(2-morpholinoethoxy)phenyl)pyridin-2-yl)-N-benzylacetamide (Form A) characterized by thermal gravimetric analysis as having negligible weight loss below 230° C.

In one aspect, the polymorph of the invention is characterized by thermal gravimetric analysis as measured by a Mettler851$^e$ STDA/TGA instrument.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7; by a Differential Scanning Calorimetry (DSC) thermogram having a single maximum value at about 164, and by thermal gravimetric analysis as having negligible weight loss below 230° C.

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ; by a Differential Scanning Calorimetry (DSC) thermogram having a single maximum value at about 164, and by thermal gravimetric analysis as having negligible weight loss below 230° C.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ; by a Differential Scanning Calorimetry (DSC) thermogram having a single maximum value at about 164, and by thermal gravimetric analysis as having negligible weight loss below 230° C.

In one aspect, the invention includes a polymorph of the mesylate salt of 2-(5-(4-(2-morpholinoethoxy)phenyl)pyridin-2-yl)-N-benzylacetamide (Form A) characterized by Moisture-Sorption Analysis having absorption of water around 1.1 wt % water at 60% RH and 5.7 wt % water at 90% RH.

In one aspect, the polymorph of the invention is characterized by Moisture-Sorption Analysis as measured by a Hiden IGAsorp Moisture Sorption Instrument.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7; by a Differential Scanning Calorimetry (DSC) thermogram having a single maximum value at about 164; by thermal gravimetric analysis as having negligible weight loss below 230° C., and by Moisture-Sorption Analysis having absorption of water around 1.1 wt % water at 60% RH and 5.7 wt % water at 90% RH.

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ; by a Differential Scanning Calorimetry (DSC) thermogram having a single maximum value at about 164; by thermal gravimetric analysis as having negligible weight loss below 230° C., and by Moisture-Sorption Analysis having absorption of water around 1.1 wt % water at 60% RH and 5.7 wt % water at 90% RH.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ; by a Differential Scanning Calorimetry (DSC) thermogram having a single maximum value at about 164; by thermal gravimetric analysis as having negligible weight loss below 230° C., and by Moisture-Sorption Analysis having absorption of water around 1.1 wt % water at 60% RH and 5.7 wt % water at 90% RH.

In one aspect, the invention includes a polymorph of the mesylate salt of 2-(5-(4-(2-morpholinoethoxy)phenyl)pyridin-2-yl)-N-benzylacetamide mesylate salt (Form A) characterized by High-Pressure Liquid Chromatography as having a peak at around 9.1.

In one aspect, the instrument parameters for obtaining the High-Pressure Liquid Chromatography are shown in Example 10.

In one aspect, a polymorph of the invention is characterized by High-Pressure Liquid Chromatography as measured by a Waters Alliance HPLC instrument.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7; by a Differential Scanning Calorimetry (DSC) thermogram having a single maximum value at about 164; by thermal gravimetric analysis as having negligible weight loss below 230° C.; by Moisture-Sorption Analysis having absorption of water around 1.1 wt % water at 60% RH and 5.7 wt % water at 90% RH, and by High-Pressure Liquid Chromatography as having a peak at around 9.1.

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ; by a Differential Scanning Calorimetry (DSC) thermogram having a single maximum value at about 164; by thermal gravimetric analysis as having negligible weight loss below 230° C.; by Moisture-Sorption Analysis having absorption of water at 60% RH and 5.7 wt % water at 90% RH, and by High-Pressure Liquid Chromatography as having a peak at around 9.1.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ; by a Differential Scanning Calorimetry (DSC) thermogram having a single maximum value at about 164; by thermal gravimetric analysis as having negligible weight loss below 230° C.; by Moisture-Sorption Analysis having absorption of water around 1.1 wt % water at 60% RH and 5.7 wt % water at 90% RH and by High-Pressure Liquid Chromatography as having a peak at around 9.1.

In one aspect, the invention includes a polymorph of the mesylate salt of 2-(5-(4-(2-morpholinoethoxy)phenyl)pyridin-2-yl)-N-benzylacetamide mesylate salt (Form A) characterized by Attenuated Total-Reflection Fourier Transform Infrared Spectroscopy (ATR-FTIR) having characteristic peaks at about 1641, 1211, 1163, 1150, 1035, 831, 771, and 746 Wavenumbers (cm$^{-1}$).

In one aspect, a polymorph of the invention is characterized by ATR-FTIR as measured by a Thermo-Nicolet Avatar 370 with Smart Endurance Attenuated Total-Reflection Attachment.

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern substantially similar to that set forth in FIG. 7; by a Differential Scanning Calorimetry (DSC) thermogram having a single maximum value at about 164; by thermal gravimetric analysis as having negligible weight loss below 230° C.; by Moisture-Sorption Analysis having absorption of water around 1.1 wt % water at 60% RH and 5.7 wt % water at 90% RH; by High-Pressure Liquid Chromatography as having a peak at around 9.1, and by Attenuated Total-Reflection Fourier Transform Infrared Spectroscopy (ATR-FTIR) having characteristic peaks at about 1641, 1211, 1163, 1150, 1035, 831, 771, and 746 Wavenumbers (cm$^{-1}$).

In another aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 22.7, 19.7, 18.9 and 16.3 degrees 2θ; by a Differential Scanning Calorimetry (DSC) thermogram having a single maximum value at about 164; by thermal gravimetric analysis as having negligible weight loss below 230° C.; by Moisture-Sorption Analysis having absorption of water around 1.1 wt % water at 60% RH and 5.7 wt % water at 90% RH; by High-Pressure Liquid Chromatography as having a peak at around 9.1, and by Attenuated Total-Reflection Fourier Transform Infrared Spectroscopy (ATR-FTIR) having characteristic peaks at about 1641, 1211, 1163, 1150, 1035, 831, 771, and 746 Wavenumbers (cm$^{-1}$).

In one aspect, the invention includes a polymorph of the mesylate salt of 2-(5-(4-(2-morpholinoethoxy)phenyl)pyridin-2-yl)-N-benzylacetamide (Form A) characterized by an X-ray diffraction pattern including peaks at about 13.1, 15.6, 16.3, 17.5, 18.9, 19.7, 20.1, 20.9, 21.4, 22.3, 22.7, 23.5, 25.7, 26.1, 26.4, 26.8, and 27.1 degrees 2θ; by a Differential Scanning Calorimetry (DSC) thermogram having a single maximum value at about 164; by thermal gravimetric analysis as having negligible weight loss below 230° C.; by Moisture-Sorption Analysis having absorption of water around 1.1 wt % water at 60% RH and 5.7 wt water at 90% RH; by High-Pressure Liquid Chromatography as having a peak at around 9.1, and by Attenuated Total-Reflection Fourier Transform Infrared Spectroscopy (ATR-FTIR) having characteristic peaks at about 1641, 1211, 1163, 1150, 1035, 831, 771, and 746 Wavenumbers (cm$^{-1}$).

In one aspect, the invention includes a pharmaceutical composition comprising a polymorph of the mesylate salt of 2-(5-(4-(2-morpholinoethoxy)phenyl)pyridin-2-yl)-N-benzylacetamide (Form A) and a pharmaceutically acceptable exipient or carrier.

In one aspect the invention includes a method of treating or preventing disease or condition in a subject in need thereof, said method comprising the step of administering to said subject a pharmaceutical composition of the invention, wherein said disease or condition is selected from cancer, hearing loss, osteoporosis, obesity, diabetes, ophthalmic diseases, stroke, atherosclerosis, neuropathic pain, hepatitis B, autoimmune disease.

In one aspect, the invention includes a process for preparing a polymorph of the mesylate salt of 2-(5-(4-(2-morpholinoethoxy)phenyl)pyridin-2-yl)-N-benzylacetamide (Form A) comprising the step of adding methanesulfonic acid to 2-(5-(4-(2-morpholinoethoxy)phenyl)pyridin-2-yl)-N-benzylacetamide in acetone. In one aspect, the amount of said acetone is greater than 64 volumes. In one aspect, the amount of said acetone is greater than 64 volumes and less than 100 volumes. In one aspect, the amount of said acetone is 80 volumes. The term "volumes" refers to the volume of liquid needed to dissolve a mass of material i.e., (mL solvent)/(grams of compound)=volumes.

Methods of Use

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders. Such diseases and disorders include, for example, cancers, osteoporosis, cardiovascular disorders, immune system dysfunction, type II diabetes, obesity, and transplant rejection.

Compounds of the invention or salts thereof are useful in modulation a component of the kinase signaling cascade. Some compounds or salts thereof may be useful in modulation of more than one component of a kinase signaling cascade. The phrase "modulates one or more components of a protein kinase signaling cascade" means that one or more components of the kinase signaling cascade are affected such that the functioning of a cell changes. Components of a protein kinase signaling cascade include any proteins involved directly or indirectly in the kinase signaling pathway including second messengers and upstream and downstream targets.

A number of protein kinases and phosphatases are known, and are targets for the development of therapeutics. See, e.g., Hidaka and Kobayashi, Annu. Rev. Pharmacol. Toxicol, 1992, 32:377-397; Davies et al., Biochem. J., 2000, 351:95-105, each of which is incorporated by reference herein.

One family of kinases, the protein tyrosine kinases are divided into two large families: receptor tyrosine kinases, or RTKs (e.g., insulin receptor kinase (IRK), epidermal growth factor receptor (EGFR), basic fibroblast growth factor receptor (FGFR), platelet-derived growth factor receptor (PDGFR), vascular endothelial growth factor receptor (VEGFR-2 or Flk1/KDR), and nerve growth factor receptor (NGFR)) and nonreceptor tyrosine kinases, or NRTKs (e.g., the Src family (Src, Fyn, Yes, Blk, Yrk, Fgr, Hck, Lek, and Lyn), Fak, Jak, Abl and Zap70). See, for example, Parang and Sun, Expert Opin. Ther. Patents, 2005, 15:1183-1207, incorporated by reference herein.

Because of the role of Src kinases in a variety of cancers, these kinases are the subject of a number of studies relating to the development of Src inhibitors as cancer therapeutics, including highly metastatic cancer cell growth. Src inhibitors are sought as therapeutics for a variety of cancers, including, for example, colon cancer, precancerous colon lesions, ovarian cancer, breast cancer, epithelial cancers, esophageal cancer, non-small cell lung cancer, pancreatic cancer, and others. See, e.g., Frame, Biochim. Biophys. Acta, 2002, 1602:114-130 and Parang and Sun, Expert Opin. Ther. Patents, 2005, 15:1183-1207.

Inhibition of other kinases may be useful in the treatment and modulation of other types of diseases and disorders. For example, various eye diseases may be inhibited or prevented by administration of VEGF receptor tyrosine kinase inhibitors. Inhibitors of the tyrosine phosphatase PTP-1B and/or glycogen phosphorylase may provide treatments for Type II diabetes or obesity. Inhibitors of p56lck may be useful in treating immune system disorders. Other targets include HIV reverse transcriptase, thromboxane synthase, EGFRTK, p55 fyn, etc.

Compounds of the invention or salts thereof may be Src signaling inhibitors that bind in the Src peptide substrate site. The activity of various compounds of the invention and salts has been studied in c-Src (527F, constitutively active and transforming) transformed NIH3T3 cells and in human colon cancer cells (HT29). For example, in these cell lines, KX2-391 was shown to reduce the phosphorylation level of known Src protein substrates in a dose-dependent fashion and in good correlation with growth inhibitory effects. Thus, in some embodiments, compounds of the invention or salts thereof may directly inhibit Src, and may do so by binding in the peptide binding site (as opposed to binding at an allosteric site).

Molecular modeling experiments have been performed which show that compounds of the invention fit into the model Src substrate site (See, e.g., U.S. Pat. Nos. 7,005,445 and 7,070,936). Modeling is also used to retool the Src kinase inhibitor scaffolds in order to target other kinases, simply by using a different set of side chains present on the molecules and/or modifying the scaffold itself.

Without wishing to be bound by theory, it is believed that the conformation of some kinases (e.g., Src) outside cells relative to the conformation inside cells is markedly different, because inside cells, many kinases are is embedded in multi-protein signaling complexes. Thus, because the peptide substrate binding site is not well formed in an isolated kinase (as shown by Src x-ray structures), it is believed that the activity against isolated kinase for a peptide substrate binding inhibitor would be weak. Binding to this site in an isolated kinase assay requires the inhibitor to capture the very small percentage of total protein in an isolated enzyme assay that is in the same conformation that exists inside cells. This requires a large excess of the inhibitor to drain significant amounts of the enzyme from the catalytic cycle in the assay in order to be detectable.

However, for cell-based assays, a large inhibitor excess is not needed because the peptide binding site is expected to be formed. In cell-based Src assays, SH2 & SH3 domain binding proteins have already shifted the Src conformation so that the peptide substrate binding site is fully formed. Thus, low concentrations of the inhibitor can remove the enzyme from the catalytic cycle since all of the enzyme is in the tight binding conformation.

The vast majority of known kinase inhibitors are ATP competitive and show poor selectivity in a panel of isolated kinase assays. However, many of the compounds of the invention or salts thereof are thought to be peptide substrate binding inhibitors. Thus, traditional high throughput screening of compounds and salts against isolated enzymes, such as Src, would not result in the discovery of compounds of the invention and salts thereof.

Compounds of the invention or salts thereof may be a kinase inhibitor. The compound of the invention or salt thereof may be a non-ATP competitive kinase inhibitor. The compound of the invention or salt thereof may inhibit a kinase directly, or it may affect the kinase pathway. In one embodiment, the compound or salt thereof inhibits one or more components of a protein kinase signaling cascade. In another embodiment, the compound or salt thereof is an allosteric inhibitor. In another embodiment, the compound or salt thereof is a peptide substrate inhibitor. In another embodiment, the compound or salt thereof does not inhibit ATP binding to a protein kinase. In one embodiment, the compound or salt thereof inhibits a Src family protein kinase. In another embodiment, the Src family protein kinase is $pp60^{c-src}$ tyrosine kinase.

The compounds of the present invention or salts thereof are useful as pharmaceutical agents, for example, as therapeutic agents for treating humans and animals. The compounds or salts thereof may be used without limitation, for example, as anti-cancer, anti-angiogenesis, anti-metastatic, anti-microbial, anti-bacterial, anti-fungal, anti-parasitic and/or anti-viral agents. Certain polymorphs may be used without limitation, for example, as anti-cancer, anti-angiogenesis, anti-metastatic, anti-microbial, anti-bacterial, anti-fungal, anti-parasitic and/or anti-viral agents.

In one embodiment, the administration of the composition of the invention is carried out orally, parentally, subcutaneously, intravenously, intramuscularly, intraperitoneally, by intranasal instillation, by intracavity or intravesical instillation, topically e.g., by administering drops into the ear, intraarterially, intralesionally, by metering pump, or by application to mucous membranes. In another embodiment, the compound or salt thereof is administered with a pharmaceutically acceptable carrier.

Cancer

There is considerable recent literature support for targeting pp60c-src (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al. (1999) Oncogene 18(33): 4654-4662). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hirano, et al., Proc. Annu. Meet. Am. Assoc. Cancer Res. 38:A1925 (1997)). Additionally, reduced VEGF mRNA expression was noted upon Src inhibition and tumors derived from these Src-inhibited cell lines showed reduced angiogenic development (Ellis et al., Journal of Biological Chemistry 273 (2):1052-1057 (1998)).

Src has been proposed to be a "universal" target for cancer therapy since it has been found to be overactivated in a growing number of human tumors (Levitzki, Current Opinion in Cell Biology, 8, 239-244 (1996); Levitzki, Anti-Cancer Drug Design, 11, 175-182 (1996)). The potential benefits of Src inhibition for cancer therapy appear to be four-fold inhibition of uncontrolled cell growth caused by autocrine growth factor loop effects, inhibition of metastasis due to triggering apoptosis upon breaking free from the cell matrix, inhibition of tumor angiogenesis via reduced VEGF levels, and low toxicity.

Prostate cancer cells have been reported to have both an over expression of paxillin and p130cas and are hyperphosphorylated (Tremblay et al., Int. J. Cancer, 68, 164-171, 1996) and may thus be a prime target for Src inhibitors.

The invention includes a method of preventing or treating a cell proliferation disorder by administering a pharmaceutical composition that includes a substantially pure KX2-391, or a salt, solvate, hydrate, or prodrug thereof, and at least one pharmaceutically acceptable excipient to a subject in need thereof. The invention includes substantially pure KX2-391 bis-HCl. The invention includes substantially pure KX2-391 mesylate. The invention includes a polymorph of KX2-391•MSA e.g., Form A.

For example, the cell proliferation disorder is pre-cancer or cancer. The cell proliferation disorder treated or prevented by the compounds of the invention or salts thereof may be a cancer, such as, for example, colon cancer or lung cancer. The cell proliferation disorder treated or prevented by the compounds of the invention or salts thereof may be a hyperproliferative disorder. The cell proliferation disorder treated or prevented by the compounds of the invention or salts thereof may be psoriases.

Treatment or prevention of the proliferative disorder may occur through the inhibition of a tyrosine kinase. For example, the tyrosine kinase can be a Src kinase or focal adhesion kinase (FAK).

In one embodiment, a compound of the invention or salt thereof may be used to treat or prevent brain cancer in a subject. Another aspect of the invention includes use of a compound of the invention or salt thereof in the manufacture of a medicament to treat or prevent brain cancer. In order to protect against brain cancer, the compound or salt may be administered prior to the development of brain cancer in a subject. Alternatively, the compound or salt may be used to treat brain cancer in a subject. A compound of the instant invention or salt thereof used to treat or prevent brain cancer may be involved in modulating a kinase signaling cascade e.g., a kinase inhibitor, a non-ATP competitive inhibitor, a tyrosine kinase inhibitor, a protein kinase phosphatase inhibitor or a protein-tyrosine phosphates 1B inhibitor.

The term "brain cancer" encompasses a variety of cancers. There can be actual brain tumors which arise from the brain itself, known as primary brain cancers of which there are several. The term "brain cancer" refers to malignant tumors i.e., tumors that grow and spread aggressively, overpowering healthy cells by taking up their space, blood, and nutrients. Tumors that do not spread aggressively are called benign tumors. Benign tumors are generally less serious than a malignant tumor, but a benign tumor can still cause problems in the brain. There can also be brain metastases, which represent the spread of other cancers, such as lung or breast to the brain.

Brain tumors are classified by both the cell of the brain that makes them up and how the tumor looks under the microscope. Primary brain tumors arise from any of the cells in the brain, or from specific structures in the brain. Glia cells support the neurons of the brain and tumors which arise from these cells are known as glial tumors. The membrane that surrounds the brain can also develop tumors and these are known as meningiomas. There are other types of tumors, which involve other structures of the brain including ependymoma. The most common primary brain tumors are gliomas, meningiomas, pituitary adenomas, vestibular schwannomas, and primitive neuroectodermal tumors (medullablastomas).

The present invention provides a method of treating or preventing glioblastoma, a malignant rapidly growing astrocytoma of the central nervous system and usually of a cerebral hemisphere. Synonyms for glioblastoma include glioblastoma multiforme (GBM), giant cell glioblastoma, and multiforme spongioblastoma multiforme. Gioblastoma is the most common malignant primary brain tumor and have proven very difficult to treat. These tumors are often aggressive and infiltrate surrounding brain tissue. Glioblastomas arise from glial cells, which are cells that form the tissue that surrounds and protects other nerve cells found within the brain and spinal cord. Gioblastomas are mainly composed of star-shaped glial cells known as astrocytes. The term "glioma" includes any type of brain tumor such as astrocytomas, oligodendrogliomas, ependymomas, and choroid plexus papillomas. Astrocytomas come in four grades based on how fast the cells are reproducing and the likelihood that they will infiltrate nearby tissue. Grades I or II astrocytomas are non-malignant and may be referred to as low-grade. Grades III and IV astrocytomas are malignant and may be referred to as high-grade astrocytomas. Grade II astrocytomas are known as anaplastic astrocytomas. Grade IV astrocytomas are known as glioblastoma multiforme.

The invention provides a method of treating or preventing medulloblastoma. Medulloblastoma is a highly malignant primary brain tumor that originates in the cerebellum or posterior fossa. Originally considered to be a glioma, medulloblastoma is now known to be of the family of cranial primitive neuroectodermal tumors (PNET).

Tumors that originate in the cerebellum are referred to as infratentorial because they occur below the tentorium, a thick membrane that separates the cerebral hemispheres of the brain from the cerebellum. Another term for medulloblastoma is infratentorial PNET. Medulloblastoma is the most common PNET originating in the brain. All PNET tumors of the brain are invasive and rapidly growing tumors that, unlike most brain tumors, spread through the cerebrospinal fluid (CSF) and frequently metastasize to different locations in the brain and spine. The peak of occurrence of medullablastoma is seven years of age. Seventy percent of medulloblastomas occur in individuals younger than 16. Desmoplastic medulloblastoma is encountered especially in adulthood. This type of tumor rarely occurs beyond the fifth decade of life.

The present invention provides a method for treating or preventing neuroblastoma, a cancer that forms in nerve tissue. The cells of neuroblastoma usually resemble very primitive developing nerve cells found in an embryo or fetus. The term neuro indicates "nerves," while blastoma refers to a cancer that affects immature or developing cells. Neurons (nerve cells) are the main component of the brain and spinal cord and of the nerves that connect them to the rest of the body. Neuroblastoma usually begins in the adrenal glands, but it may also begin in the spinal cord. Neuroblastoma is the most common extracranial solid cancer in childhood. In 2007, neuroblasoma was the most common cancer in infancy, with an annual incidence of about 650 new cases per year in the US. Close to 50 percent of neuroblastoma cases occur in children younger than two years old. It is a neuroendocrine tumor, arising from any neural crest element of the sympathetic nervous system or SNS. A branch of the autonomic nervous system, the SNS is a nerve network that carries messages from the brain throughout the body and is responsible for the fight-or-flight response and production of adrenaline or epinephrine.

The invention provides a method of treating or preventing neuroepithelioma, malignant tumors of the neuroepithelium. Neuroepithelioma is found most commonly in children and young adults. It arises most often in the chest wall, pelvis, or extremity, either in bone or soft tissue. Procedures used in the diagnosis may include blood and urine tests, X rays of the affected bone and the whole body and lungs, bone marrow aspirations, CT scans, and fluoroscopy. Treatments include surgery, radiation therapy and chemotherapy. Ewing's tumors are an example of a type of peripheral neuroepithelioma.

Kinases have been shown to play a role in brain cancers. Gene expression profiles of glioblastoma multiforme have identified tyrosine kinases as playing a role in glioma migration/invasion. For example, PYK2 is a member of the focal adhesion family of nonreceptor tyrosine kinases; it is closely involved with src-induced increased actin polymerization at the fibroblastic cell periphery. Its role in glioma migration/invasion has become more clear, as overexpression of PYK2 induced glioblastoma cell migration in culture. Levels of activated PYK2 positively correlated with the migration phenotype in four glioblastoma cell lines (SF767, G112, T98G and U118). Analysis of activated PYK2 in GBM invastion in situ revealed strong staining in infiltrating GBM cells. (See, Hoelzinger et al, Neoplasia, vol. 7(1)7-16. Thus, modulation of a kinase receptor using a compound of the invention may be useful in the prevention or treatment of brain cancers such as glioblastoma multiforme.

The invention is also drawn to a method of treating or preventing cancer or a proliferation disorder in a subject, comprising administering a composition comprising an effective amount of a substantially pure KX2-391, or a salt, solvate, hydrate, or prodrug thereof, for example, substantially pure KX2-391, KX2-391•2HCl or KX2-391•MSA. The invention includes administering an effective amount of a substantially pure polymorph of KX2-391•MSA e.g., Form A.

Hearing Loss

As described herein, a compound of the invention or salt thereof may be used to protect against or prevent hearing loss in a subject. In one aspect, a polymorph of the invention may be used to protect against or prevent hearing loss in a subject. In order to protect against hearing loss, the compound or salt may be administered prior to noise exposure or exposure to a drug which induces hearing loss to prevent hearing loss or to reduce the level of hearing loss. Such drugs which induce hearing loss may include chemotherapeutic drugs (e.g., platinum-based drugs which target hair cells) and aminoglycoside antibiotics. A compound of the invention or salt may provide a synergistic effect with certain cancer drugs. For example, promising inhibitors can be screened in primary human tumor tissue assays, particularly to look for synergy with other known anti-cancer drugs. In addition, the protein kinase inhibitors may reduce toxicity of certain cancer drugs (e.g., platinum-based drugs which are toxic to the cochlea and kidney), thereby allowing increased dosage.

Alternatively, a compound of the invention or salt thereof may be used to treat hearing loss in a subject. In this embodiment, the compound or salt is administered to the subject subsequent to the initiation of hearing loss to reduce the level of hearing loss. A compound of the invention may be involved in modulating a kinase cascade, e.g. a kinase inhibitor, a non-ATP competitive inhibitor, a tyrosine kinase inhibitor, a Src inhibitor or a focal adhesion kinase (FAK) modulator. Although not wishing to be bound by theory, it is believed that the administration of kinase inhibitors prevents apoptosis of cochlear hair cells, thereby preventing hearing loss. In one embodiment, administration of a compound of the invention or salt thereof is administered to a subject suffering from hearing loss in order to prevent further hearing loss. In another embodiment, administration of a compound of the invention or salt thereof is administered to a subject suffering from hearing loss in order to restore lost hearing. In particular, following noise exposure, the tight cell junctures between the cochlear hair cells, as well as the cell-extracellular matrix interaction, are torn and stressed. The stressing of these tight cell junctures initiates apoptosis in the cells through a complex signaling pathway in which tyrosine kinases act as molecular switches, interacting with focal adhesion kinase to transduce signals of cell-matrix disruptions to the nucleus. It is believed that the administration of kinase inhibitors prevents the initiation of apoptosis in this cascade.

The identification of apoptosis in the noise-exposed cochlea has generated a number of new possibilities for the prevention of noise-induced hearing loss (NIHL) (Hu, et al.; 2000, Acta. Otolaryngol., 120, 19-24). For example, the ear can be protected from NIHL by administration of antioxidant drugs to the round window of the ear (Hight, et al.; 2003, Hear. Res., 179, 21-32; Hu, et al.; Hear. Res. 113, 198-206). Specifically, NIHL has been reduced by the administration of FDA-approved antioxidant compounds (N-L-acetylcysteine (L-NAC) and salicylate) in the chinchilla (Kopke, et al.; 2000, Hear. Res., 149, 138-146). Moreover, Harris et al. have recently described prevention of NIHL with Src-PTK inhibitors (Harris, et al.; 2005, Hear. Res., 208, 14-25). Thus, it is hypothesized that the administration of a compound of the instant invention which modulates the activity of kinases, is useful for treating hearing loss.

Changes in cell attachment or cell stress can activate a variety of signals through the activation of integrins and through the phosphorylation of PTKs, including the Src family of tyrosine kinases. Src interactions have been linked to signaling pathways that modify the cytoskeleton and activate a variety of protein kinase cascades that regulate cell survival and gene transcription (reviewed in Giancotti and Ruoslahti; 1999, Science, 285, 1028-1032). In fact, recent results have indicated that outer hair cells (OHC), which had detached at the cell base following an intense noise exposure, underwent apoptotic cell death. Specifically, the Src PTK signaling cascade is thought to be involved in both metabolic- and mechanically-induced initiation of apoptosis in sensory cells of the cochlea. In a recent study, Src inhibitors provided protection from a 4 hour, 4 kHz octave band noise at 106 dB, indicating that Src-PTKs might be activated in outer hair cells following noise exposure (Harris, et al.; 2005, Hear. Res., 208, 14-25). Thus, compounds of the instant invention that modulate the activity of Src, are useful in treating hearing loss.

Another aspect of the invention includes a method of protecting against or treating hearing loss in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound is administered before initiation of hearing loss. In another embodiment, the compound is administered after initiation of hearing loss.

In one embodiment, the compound is administered in combination with a drug that causes hearing loss e.g., cis platinum or an aminoglycoside antibiotic. In another embodiment, the compound is administered in combination with a drug that targets hairy cells.

Osteoporosis

The present invention relates to a method for protecting against or treating osteoporosis in a subject. In one aspect, the method includes protecting against or treating osteoporosis using a polymorph of the invention. This method involves administering an effective amount of a compound of the invention or salt thereof to the subject to protect against or to treat osteoporosis. In order to protect against osteoporosis, the compound or salt may be administered prior to the development of osteoporosis. Alternatively, the compound or salt may be used to treat osteoporosis in a subject. In one embodiment, the compound or salt is administered to the subject subsequent to the initiation of osteoporosis to reduce the level of osteoporosis.

A compound of the invention or salt thereof can be, e.g. a non-ATP competitive inhibitor. The compound of the invention or salt thereof can modulate a kinase signaling cascade, depending upon the particular side chains and scaffold modifications selected. The compound of the invention can be a kinase inhibitor. For example, the compound or salt can be a protein tyrosine kinase (PTK) inhibitor. The proline-rich tyrosine kinase (PYK2; also known as cell adhesion kinase β, related adhesion focal tyrosine kinase, or calcium-dependent tyrosine kinase) and focal adhesion kinase (FAK) are members of a distinct family of non receptor protein-tyrosine kinases that are regulated by a variety of extracellular stimuli (Avraham, et al.; 2000, *Cell Signal.*, 12, 123-133; Schlaepfer, et al.; 1999, *Prog. Biophys. Mol. Biol.*, 71, 435-478). The compound of the invention or salt thereof can be a Src inhibitor. It has been shown that Src deficiency is associated with osteoporosis in mice, because of loss of osteoclast function (Soriano, et al.; 1991, *Cell*, 64, 693-702). Alternatively, the compound of the invention or salt thereof can modulate the expression of interleukin-1 receptor associated kinase M (IRAK-M). Mice that lack IRAK-M develop severe osteoporosis, which is associated with the accelerated differentiation of osteoclasts, an increase in the half-life of osteoclasts, and their activation (Hongmei, et al.; 2005, *J. Exp. Med.*, 201, 1169-1177).

Multinucleated osteoclasts originate from the fusion of mononuclear phagocytes and play a major role in bone development and remodeling via the resorption of bone. Osteoclasts are multinucleated, terminally differentiated cells that degrade mineralized matrix. In normal bone tissue, there is a balance between bone formation by osteoblasts and bone resorption by osteoclasts. When the balance of this dynamic and highly regulated process is disrupted, bone resorption can exceed bone formation resulting in quantitative bone loss. Because osteoclasts are essential for the development and remodeling of bone, increases in their number and/or activity lead to diseases that are associated with generalized bone loss (e.g., osteoporosis) and others with localized bone loss (e.g., rheumatoid arthritis, periodontal disease).

Osteoclasts and osteoblasts both command a multitude of cellular signaling pathways involving protein kinases. Osteoclast activation is initiated by adhesion to bone, cytoskeletal rearrangement, formation of the sealing zone, and formation of the polarized ruffled membrane. It is believed that protein-tyrosine kinase 2 (PYK2) participates in the transfer of signals from the cell surface to the cytoskeleton, as it is tyrosine phosphorylated and activated by adhesion-initiated signaling in osteoclasts (Duong, et al.; 1998, *J. Clin. Invest.*, 102, 881-892). Recent evidence has indicated that the reduction of PYK2 protein levels results in the inhibition of osteoclast formation and bone resorption in vitro (Duong, et al.; 2001, *J. Bio. Chem.*, 276, 7484-7492). Therefore, the inhibition of PYK2 or other protein tyrosine kinases might reduce the level of osteoporosis by decreasing osteoclast formation and bone resorption. Thus, without wishing to be bound by theory, it is hypothesized that the administration of a compound of the instant invention or salt thereof will modulate kinase (e.g. PTK) activity and therefore result in the inhibition of osteoclast formation and/or bone resorption, thereby treating osteoporosis.

Src tyrosine kinase stands out as a promising therapeutic target for bone disease as validated by Src knockout mouse studies and in vitro cellular experiments, suggesting a regulatory role for Src in both osteoclasts (positive) and osteoblasts (negative). In osteoclasts, Src plays key roles in motility, polarization, survival, activation (ruffled border formation) and adhesion, by mediating various signal transduction pathways, especially in cytokine and integrin signaling (Parang and Sun; 2005, *Expert Opin. Ther. Patents*, 15, 1183-1207). Moreover, targeted disruption of the src gene in mice induces osteopetrosis, a disorder characterized by decreased bone resorption, without showing any obvious morphological or functional abnormalities in other tissues or cells (Soriano, et al.; 1991, *Cell*, 64, 693-702). The osteopetrotic phenotype of src$^{-/-}$ mice is cell-autonomous and results from defects in mature osteoclasts, which normally express high levels of Src protein (Home, et al.; 1991, *Cell*, 119, 1003-1013). By limiting the effectiveness of Src tyrosine kinase, which triggers osteoclast activity and inhibits osteoblasts, Src inhibitors are thought to lessen bone break down and encourage bone formation. Because osteoclasts normally express high levels of Src, inhibition of Src kinase activity might be useful in the treatment of osteoporosis (Missbach, et al.; 1999, *Bone*, 24, 437-449). Thus, the PTK inhibitors of the instant invention that modulate the activity of Src, are useful in treating osteoporosis.

For example, a knock-out of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., (1997) Genes & Development 11: 2835-2844). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Another aspect of the invention includes a method of protecting against or treating osteoporosis in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before initiation of osteoporosis. In another embodiment, the compound or salt is administered after initiation of osteoporosis.

Obesity

As described herein, a compound of the invention or salt thereof may be used to protect against or prevent obesity in a subject. In one aspect, a polymorph of the invention may be used to protect against or prevent obesity in a subject. In order to protect against obesity, the compound or salt may be administered prior to the development of obesity in a subject. For example, the compound or salt may be administered to prevent or reduce weight gain. Alternatively, the compound or salt may be used to treat obesity in a subject. A compound of the instant invention or salt thereof may be involved in modulating a kinase signaling cascade, e.g., a kinase inhibitor, a non-ATP competitive inhibitor, a tyrosine kinase inhibitor, a protein tyrosine phosphatase inhibitor, or a protein-tyrosine phosphatase 1B inhibitor.

Obesity is often associated with diabetes and increased insulin resistance in insulin responsive tissues, such as skeletal muscle, liver, and white adipose tissue (Klaman, et al.; 2000, *Mol. Cell. Biol.*, 20, 5479-5489). Insulin plays a critical role in the regulation of glucose homeostasis, lipid metabolism, and energy balance. Insulin signaling is initiated by binding of insulin to the insulin receptor (IR), a receptor tyrosine kinase. Insulin binding evokes a cascade of phosphorylation events, beginning with the autophosphorylation of the IR on multiple tyrosyl residues. Autophosphorylation enhances IR kinase activity and triggers downstream signaling events. The stimulatory effects of protein tyrosine kinases and the inhibitory effects of protein tyrosine phosphatases largely define the action of insulin. Appropriate insulin signaling minimizes large fluctuations in blood glucose concentrations and ensures adequate delivery of glucose to cells. Since insulin stimulation leads to multiple tyrosyl phosphorylation events, enhanced activity of one or more protein-tyrosine phosphatases (PTPs) could lead to insulin resistance, which may lead to obesity. Indeed, increased PTP activity has been reported in several insulin-resistant states, including obesity (Ahmad, et al.; 1997, *Metabolism*, 46, 1140-1145). Thus, without wishing to be bound by theory, the administration of a compound of the instant invention or salt thereof modulates kinase (e.g., PTP) activity, thereby treating obesity in a subject.

Insulin signaling begins with the activation of the IR via tyrosine phosphorylation and culminates in the uptake of glucose into cells by the glucose transporter, GLUT4 (Saltiel and Kahn; 2001, *Nature*, 414, 799-806). The activated IR must then be deactivated and returned to a basal state, a process that is believed to involve protein-tyrosine phosphatase-1B (PTP-1B) (Ahmad, et al; 1997, *J. Biol. Chem.*, 270, 20503-20508). Disruption of the gene that codes for PTP-1B in mice results in sensitivity to insulin and increased resistance to diet-induced obesity (Elchebly, et al.; 1999, *Science*, 283, 1544-1548; Klaman, et al.; 2000, *Mol. Cell. Biol.*, 20, 5479-5489). The decreased adiposity in PTP-1B deficient mice was due to a marked reduction in fat cell mass without a decrease in adipocyte number (Klaman, et al.; 2000, *Mol. Cell. Biol.*, 20, 5479-5489). Moreover, leanness in PTP-1B-deficient mice was accompanied by increased basal metabolic rate and total energy expenditure, without marked alteration of uncoupling protein mRNA expression. The disruption of the PTP-1B gene demonstrated that altering the activity of PTP-1B can modulate insulin signaling and dietary-induced obesity in vivo. Thus, without wishing to be bound by theory, the administration of a compound of the instant invention that modulates insulin signaling (e.g., PTP-1B activity), is useful in treating obesity in a subject.

Another aspect of the invention includes a method of protecting against or treating obesity in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before the subject is obese. In another embodiment, the compound or salt is administered after the subject is obese.

Diabetes

As described herein, a compound of the invention or salt thereof may be used to protect against or prevent diabetes in a subject. In one aspect, a polymorph of the invention may be used to protect against or prevent diabetes. In order to protect against diabetes, the compound or salt may be administered prior to the development of diabetes in a subject. Alternatively, the compound or salt may be used to treat diabetes in a subject. The compound of the instant invention or salt thereof may be involved in modulating a kinase signaling cascade, e.g. a kinase inhibitor, a non-ATP competitive inhibitor, a tyrosine kinase inhibitor, a phosphatase and tension homologue on chromosome 10 (PTEN) inhibitor, or a sequence homology 2-containing inositol 5'-phosphatase 2 (SHIP2) inhibitor.

Type 2 diabetes mellitus (T2DM) is a disorder of dysregulated energy metabolism. Energy metabolism is largely controlled by the hormone insulin, a potent anabolic agent that promotes the synthesis and storage of proteins, carbohydrates and lipids, and inhibits their breakdown and release back into the circulation. Insulin action is initiated by binding to its tyrosine kinase receptor, which results in autophosphorylation and increased catalytic activity of the kinase (Patti, et al.; 1998, *J. Basic Clin. Physiol. Pharmacol.* 9, 89-109). Tyrosine phosphorylation causes insulin receptor substrate (IRS) proteins to interact with the p85 regulatory subunit of phosphatidylinositol 3-kinase (PI3K), leading to the activation of the enzyme and its targeting to a specific subcellular location, depending on the cell type. The enzyme generates the lipid product phosphatidylinositol-3,4,5-trisphosphate (PtdIns(3,4,5)P$_3$), which regulates the localization and activity of numerous proteins (Kido, et al.; 2001, *J. Clin. Endocrinol. Metab.*, 86, 972-979). PI3K has an essential role in insulin-stimulated glucose uptake and storage, inhibition of lipolysis and regulation of hepatic gene expression (Saltiel, et al.; 2001, *Nature*, 414, 799-806). Overexpression of dominant-interfering forms of PI3K can block glucose uptake and translocation of glutamate transporter four, GLUT4, to the plasma membrane (Quon, et al.; 1995, *Mol. Cell. Biol.*, 15, 5403-5411). Thus, the administration of a compound of the instant invention that modulates kinase (e.g. PI3K) activity, and therefore results in increased glucose uptake, is useful in treating diabetes.

PTEN is a major regulator of PI3K signaling in may cell types, and functions as a tumor suppressor due to antagonism of the anti-apoptotic, proliferative and hypertrophic activities of the PI3K pathway (Goberdhan, et al.; 2003, *Hum. Mol. Genet.*, 12, R239-R248; Leslie, et al.; 2004, *J. Biochem.*, 382, 1-11). Although not wishing to be bound by theory, it is believed that PTEN attenuates the PI3K pathway by dephosphorylation of the PtdIns(3,4,5)P$_3$ molecule, degrading this important lipid second messenger to PtdIns(4,5)P$_2$. In a recent study, reduction of endogenous PTEN protein by 50% using small interfering RNA (siRNA) enhanced insulin-dependent increases in PtdIns(3,4,5)P$_3$ levels, and glucose uptake (Tang, et al.; 2005, *J. Biol. Chem.*, 280, 22523-22529). Thus, without wishing to be bound by theory, it is hypothesized that the administration of a compound of the instant invention that modulates PTEN activity, and therefore results in increased glucose uptake, is useful for treating diabetes.

PtdIns(3,4,5)P$_3$ levels are also controlled by the family of SRC homology 2 (SH2)-containing inositol 5'-phosphatase (SHIP) proteins, SHIP1 and SHIP2 (Lazar and Saltiel; 2006, *Nature Reviews*, 5, 333-342). SHIP2, expressed in skeletal muscle, among other insulin-sensitive tissues, catalyzes the conversion of PtdIns(3,4,5)P$_3$ into PtdIns(3,4)P$_2$ (Pesesse, et al.; 1997; *Biochem Biophys. Res. Commun.*, 239, 697-700; Backers, et al.; 2003, *Adv. Enzyme Regul.*, 43, 15-28; Chi, et al.; 2004, *J. Biol. Chem.*, 279, 44987-44995; Sleeman, et al.; 2005, *Nature Med.*, 11, 199-205). Overexpression of SHIP2 markedly reduced insulin-stimulated PtdIns(3,4,5)P$_3$ levels, consistent with the proposed capacity of SHIP2 to attenuate the activation of downstream effectors of PI3K (Ishihara, et al.; 1999, *Biochem. Biophys. Res. Commun.*, 260, 265-272). Thus, without wishing to be bound by theory, it is hypothesized that the administration of a compound of the instant invention which modulates SHIP2 activity, and therefore results in increased glucose uptake, is useful for treating diabetes.

Another aspect of the invention includes a method of protecting against or treating diabetes in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before initiation of the diabetes. In another embodiment, the compound or salt is administered after initiation of disease.

Ophthalmic Disease

As described herein, a compound of the invention may be used to protect against or prevent ophthalmic (eye) disease in a subject. In one aspect, a polymorph of the invention may be used to protect against or prevent ophthalmic (eye) disease. In order to protect against eye disease, the compound or salt may be administered prior to the development of eye disease in a subject. Alternatively, the compound or salt may be used to treat eye disease in a subject, e.g. macular degeneration, retinopathy, and macular edema. The compound of the instant invention or salt may be involved in modulating a kinase cascade, e.g. a kinase inhibitor, a non-ATP competitive inhibitor, a tyrosine kinase inhibitor, e.g. a vascular endothelial growth factor (VEGF) receptor tyrosine kinase inhibitor.

Vision-threatening neovascularization of the physiologically avascular cornea can occur. The proliferative retinopathies, principally diabetic retinopathy and age-related macular degeneration, are characterized by increased vascular permeability, leading to retinal edema and subretinal fluid accumulation, and the proliferation of new vessels that are prone to hemorrhage. Angiogenesis, the formation of new blood vessels from preexisting capillaries, is an integral part of both normal development and numerous pathological processes. VEGF, a central mediator of the complex cascade of angiogenesis and a potent permeability factor, is an attractive target for novel therapeutics. VEGF is the ligand for two membrane-bound tyrosine kinase receptors, VEGFR-1 and VEGFR-2. Ligand binding triggers VEGFR dimerization and transphosphorylation with subsequent activation of an intracellular tyrosine kinase domain. The ensuing intracellular signaling axis results in vascular endothelial cell proliferation, migration, and survival. Thus, without wishing to be bound by theory, it is hypothesized that the administration of a compound of the instant invention or salt thereof which modulates kinase activity, e.g. tyrosine kinase activity, and results in the inhibition of angiogenesis and/or neovascularization, is useful for treating an eye disease, e.g. macular degeneration, retinopathy and/or macular edema.

Macular degeneration is characterized by VEGF-mediated retinal leakage (an increase in vascular permeability) and by the abnormal growth of small blood vessels in the back of the eye (angiogenesis). VEGF has been identified in neovascular membranes in both diabetic retinopathy and age-related macular degeneration, and intraocular levels of the factor correlate with the severity of neovascularization in diabetic retinopathy (Kvanta, et al.; 1996, *Invest. Ophthal. Vis. Sci.*, 37, 1929-1934.; Aiello et al., 1994, *N. Engl. J. Med.*, 331, 1480-1487). Therapeutic antagonism of VEGF in these models results in significant inhibition of both retinal and choroidal neovascularization, as well as a reduction in vascular permeability (Aiello, et al.; 1995, *Proc. Natl. Acad. Sci. USA.*, 92, 10457-10461; Krzystolik, et al.; 2002, *Arch. Ophthal.*, 120, 338-346; Qaum, et al.; 2001, *Invest. Ophthal. Vis. Sci.*, 42, 2408-2413). Thus, without wishing to be bound by theory, it is hypothesized that the administration of a compound of the instant invention which modulates VEGF activity, and results in the inhibition of angiogenesis and/or neovascularization, is useful for treating an eye disease, e.g. macular degeneration, retinopathy and/or macular edema.

Another aspect of the invention includes a method of protecting against or treating ophthalmic diseases e.g., macular degeneration, retinopathy, macular edema, etc. in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before initiation of the ophthalmic disease. In another embodiment, the compound or salt is administered after initiation of ophthalmic disease.

Stroke

The compounds of the invention or salts thereof are used in methods of treating, preventing, or ameliorating a stroke in a subject who is at risk of suffering a stroke, is suffering from a stroke or has suffered a stroke. In one aspect, a polymorph of the invention is used in methods of treating, preventing, or ameliorating a stroke. The compounds of the invention or salts thereof are useful in methods of treating patients who are undergoing post-stroke rehabilitation.

A stroke, also known as a cerebrovascular accident (CVA), is an acute neurological injury whereby the blood supply to a part of the brain is interrupted due to either blockage of an artery or rupture of a blood vessel. The part of the brain in which blood supply is interrupted no longer receives oxygen and/or nutrients carried by the blood. The brain cells become damaged or necrotic, thereby impairing function in or from that part of the brain. Brain tissue ceases to function if deprived of oxygen for more than 60 to 90 seconds and after a few minutes will suffer irreversible injury possibly leading to a death of the tissue, i.e., infarction.

Strokes are classified into two major types: ischemic, i.e., blockage of a blood vessel supplying the brain, and hemorrhagic, i.e., bleeding into or around the brain. The majority of all strokes are ischemic strokes. Ischemic stroke is commonly divided into thrombotic stroke, embolic stroke, systemic hypoperfusion (Watershed stroke), or venous thrombosis. In thrombotic stroke, a thrombus-forming process develops in the affected artery, the thrombus, i.e., blood clot, gradually narrows the lumen of the artery, thereby impeding blood flow to distal tissue. These clots usually form around atherosclerotic plaques. There are two types of thrombotic strokes, which are categorized based on the type of vessel on which the thrombus is formed. Large vessel thrombotic stroke involves the common and internal carotids, vertebral, and the Circle of Willis. Small vessel thrombotic stroke involves the intracerebral arteries, branches of the Circle of Willis, middle cerebral artery stem, and arteries arising from the distal vertebral and basilar artery.

A thrombus, even if non-occluding, can lead to an embolic stroke if the thrombus breaks off, at which point it becomes an embolus. An embolus refers to a traveling particle or debris in the arterial bloodstream originating from elsewhere. Embolic stroke refers to the blockage of arterial access to a part of the brain by an embolus. An embolus is frequently a blood clot, but it can also be a plaque that has broken off from an atherosclerotic blood vessel or a number of other substances including fat, air, and even cancerous cells. Because an embolus arises from elsewhere, local therapy only solves the problem temporarily. Thus, the source of the embolus must be identified. There are four categories of embolic stroke: those with a known cardiac source; those with a potential cardiac or aortic source (from trans-thoracic or trans-esophageal echocardiogram); those with an arterial source; and those with unknown source.

Systemic hypoperfusion is the reduction of blood flow to all parts of the body. It is most commonly due to cardiac pump failure from cardiac arrest or arrhythmias, or from reduced cardiac output as a result of myocardial infarction, pulmonary embolism, pericardial effusion, or bleeding. Hypoxemia (i.e., low blood oxygen content) may precipitate the hypoperfusion. Because the reduction in blood flow is global, all parts of the brain may be affected, especially the "watershed" areas which are border zone regions supplied by the major cerebral arteries. Blood flow to these area has not necessary stopped, but instead may have lessened to the point where brain damage occurs.

Veins in the brain function to drain the blood back to the body. When veins are occluded due to thrombosis, the draining of blood is blocked and the blood backs up, causing cerebral edema. This cerebral edema can result in both ischemic and hemorrhagic strokes. This commonly occurs in the rare disease sinus vein thrombosis.

Stroke is diagnosed in a subject or patient using one or more of a variety of techniques known in the art, such as, for example, neurological examination, blood tests, CT scans (without contrast enhancements), MRI scans, Doppler ultrasound, and arteriography (i.e., roentgenography of arteries after injection of radiopacque material into the blood stream). If a stroke is confirmed on imaging, various other studies are performed to determine whether there is a peripheral source of emboli. These studies include, e.g., an ultrasound/doppler study of the carotid arteries (to detect carotid stenosis); an electrocardiogram (ECG) and echocardiogram (to identify arrhythmias and resultant clots in the heart which may spread to the brain vessels through the bloodstream); a Holter monitor study to identify intermittent arrhythmias and an angiogram of the cerebral vasculature (if a bleed is thought to have originated from an aneurysm or arteriovenous malformation).

Compounds or salts useful in these methods of treating, preventing or ameliorating stroke or a symptom associated with stroke are compounds or salts that modulate kinase signaling cascade proceeding, during or after a stroke. In some embodiments, the compound or salt is a kinase inhibitor. For example, the compound or salt is a tyrosine kinase inhibitor. In an embodiment, the tyrosine kinase inhibitor is an Src inhibitor. For example, the compound or salt used in the methods of treating, preventing or ameliorating stroke or a symptom associated with stroke described herein is an allosteric inhibitor of kinase signaling cascade preceding, during or after a stroke. Preferably, the compound or salt used in the methods of treating, preventing or ameliorating stroke or a symptom associated with stroke described herein is a non-ATP competitive inhibitor of kinase signaling cascade preceding, during or after a stroke.

Inhibition of Src activity has been shown to provide cerebral protection during stroke. (See Paul et al., Nature Medicine, vol. 7(2):222-227 (2001), which is hereby incorporated by reference in its entirety). Vascular endothelia growth factor (VEGF), which is produced in response to the ischemic injury, has been shown to promote vascular permeability. Studies have shown that the Src kinase regulates VEGF-mediated VP in the brain following stroke, and administration of an Src inhibitor before and after stroke reduced edema, improved cerebral perfusion and decreased infarct volume after injury occurred. (Paul et al., 2001). Thus, Src inhibition may be useful in the prevention, treatment or amelioration of secondary damage following a stroke.

The compounds of the invention or salts thereof prevent, treat or ameliorate stroke or a symptom associated with stroke. Symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause.

Generally there are three treatment stages for stroke: prevention, therapy immediately after the stroke, and post-stroke rehabilitation. Therapies to prevent a first or recurrent stroke are based on treating the underlying risk factors for stroke, such as, e.g., hypertension, high cholesterol, atrial fibrillation, and diabetes. Acute stroke therapies try to stop a stroke while it is happening by quickly dissolving the blood clot causing an ischemic stroke or by stopping the bleeding of a hemorrhagic stroke. Post-stroke rehabilitation helps individuals overcome disabilities that result from stroke damage. Medication or drug therapy is the most common treatment for stroke. The most popular classes of drugs used to prevent or treat stroke are anti-thrombotics (e.g., anti-platelet agents and anticoagulants) and thrombolytics. The compounds or salts are administered to a patient who is at risk of suffering a stroke, is suffering from a stroke or has suffered a stroke at a time before, during, after, or any combination thereof, the occurrence of a stroke. The compounds of the invention or salts thereof are administered alone, in pharmaceutical compositions, or in combination with any of a variety of known treatments, such as, for example, an anti-platelet medication (e.g., aspirin, clopidogrel, dipyridamole), an anti-coagulant (e.g., warfarin), or a thrombolytic medication (e.g., tissue plasminogen activator (t-PA), reteplase, Urokinase, streptokinase, tenectaplase, lanoteplase, or anistreplase.

Another aspect of the invention includes a method of protecting against or treating stroke in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before a stroke has occurred. In another embodiment, the compound or salt is administered after a stroke has occurred.

Atherosclerosis

The compounds of the invention or salts thereof are used in methods of treating, preventing, or ameliorating atherosclerosis or a symptom thereof in a subject who is at risk for or suffering from atherosclerosis. In one aspect, a polymorph of the invention is used in methods of treating, preventing or ameliorating atherosclerosis or a symptom thereof.

Atherosclerosis is a disease affecting the arterial blood vessel and is commonly referred to as a "hardening" of the arteries. It is caused by the formation of multiple plaques within the arteries. Atherosclerotic plaques, though compensated for by artery enlargement, eventually lead to plaque ruptures and stenosis (i.e., narrowing) of the artery, which, in turn, leads to an insufficient blood supply to the organ it feeds. Alternatively, if the compensating artery enlargement process is excessive, a net aneurysm results. These complications are chronic, slowly progressing and cumulative. Most commonly, soft plaque suddenly ruptures, causing the formation of a blood clot (i.e., thrombus) that rapidly slows or stops blood flow, which, in turn, leads to death of the tissues fed by the artery. This catastrophic event is called an infarction. For example, coronary thrombosis of a coronary artery causes a myocardial infarction, commonly known as a heart attack. A myocardial infarction occurs when an atherosclerotic plaque slowly builds up in the inner lining of a coronary artery and then suddenly ruptures, totally occluding the artery and preventing blood flow downstream.

Atherosclerosis and acute myocardial infarction are diagnosed in a patient using any of a variety of clinical and/or laboratory tests such as, physical examination, radiologic or ultrasound examination and blood analysis. For example, a doctor or clinical can listen to a subject's arteries to detect an abnormal whooshing sound, called a bruit. A bruit can be heard with a stethoscope when placed over the affected artery. Alternatively, or in addition, the clinician or physician can check pulses, e.g., in the leg or foot, for abnormalities such as weakness or absence. The physician or clinical may perform blood work to check for cholesterol levels or to check the levels of cardiac enzymes, such as creatine kinase, troponin and lactate dehydrogenase, to detect abnormalities. For example, troponin sub-units I or T, which are very specific for the myocardium, rise before permanent injury develops. A positive troponin in the setting of chest pain may accurately predict a high likelihood of a myocardial infarction in the near future. Other tests to diagnose atherosclerosis and/or myocardial infarction include, for example, EKG (electrocardiogram) to measure the rate and regularity of a subject's heartbeat; chest X-ray, measuring ankle/brachial index, which compares the blood pressure in the ankle with the blood pressure in the arm; ultrasound analysis of arteries; CT scan of areas of interest; angiography; an exercise stress test, nuclear heart scanning; and magnetic resonance imaging (MRI) and positron emission tomography (PET) scanning of the heart.

Compounds or salts useful in these methods of treating, preventing or ameliorating atherosclerosis or a symptom thereof are compounds or salts that modulate kinase signaling cascade in a patient at risk for or suffering from atherosclerosis. In some embodiments, the compound or salt is a kinase inhibitor. For example, the compound or salt is a tyrosine kinase inhibitor. In an embodiment, the tyrosine kinase inhibitor is a Src inhibitor. Preferably, the compound or salt used in the methods of treating, preventing or ameliorating atherosclerosis or a symptom thereof described herein is an allosteric inhibitor of kinase signaling cascade involved in atherosclerosis. Preferably, the compound or salt used in the methods of treating, preventing or ameliorating atherosclerosis or a symptom associated with atherosclerosis described herein is a non-ATP competitive inhibitor of kinase signaling cascade involved in atherosclerosis.

Cellular signal transduction by Src is believed to play a key role in increased permeability of vessels, known as vascular permeability (VP). Vascular endothelia growth factor (VEGF), which is produced in response to the ischemic injury, including, e.g., myocardial infarction, has been shown to promote vascular permeability. Studies have shown that the inhibition of Src kinase decreases VEGF-mediated VP. (See Parang and Sun, Expert Opin. Ther. Patents, vol. 15(9): 1183-1206 (2005), which is hereby incorporated by reference in its entirety). Mice treated with a Src inhibitor demonstrated reduced tissue damage associated with trauma or injury to blood vessels after myocardial infarction, as compared to untreated mice. (See e.g., U.S. Patent Publication Nos. 20040214836 and 20030130209 by Cheresh et al., the contents of which are hereby incorporated by reference in their entirety). Thus, Src inhibition may be useful in the prevention, treatment or amelioration of secondary damage following injury due to atherosclerosis, such as, for example, myocardial infarction.

Atherosclerosis generally does not produce symptoms until it severely narrows the artery and restricts blood flow, or until it causes a sudden obstruction. Symptoms depend on where the plaques and narrowing develop, e.g., in the heart, brain, other vital organs and legs or almost anywhere in the body. The initial symptoms of atherosclerosis may be pain or cramps when the body requires more oxygen, for example during exercise, when a person may feel chest pain (angina) because of lack of oxygen to the heart or leg cramps because of lack of oxygen to the legs. Narrowing of the arteries supplying blood to the brain may cause dizziness or transient ischemic attacks (TIA's) where the symptoms and signs of a stroke last less than 24 hours. Typically, these symptoms develop gradually.

Symptoms of myocardial infarction are characterized by varying degrees of chest pain, discomfort, sweating, weakness, nausea, vomiting, and arrhythmias, sometimes causing loss of consciousness. Chest pain is the most common symptom of acute myocardial infarction and is often described as a tightness, pressure, or squeezing sensation. Pain may radiate to the jaw, neck, arms, back, and epigastrium, most often to the left arm or neck. Chest pain is more likely caused by myocardial infarction when it lasts for more than 30 minutes. Patients suffering from a myocardial infarction may exhibit shortness of breath (dyspnea) especially if the decrease in myocardial contractility due to the infarct is sufficient to cause left ventricular failure with pulmonary congestion or even pulmonary edema.

The compounds of the invention or salts thereof are administered alone, in pharmaceutical compositions, or in combination with any of a variety of known treatments for atherosclerosis, such as, for example, cholesterol-lowering drugs (e.g., statins), anti-platelet medications, or anti-coagulants.

Another aspect of the invention includes a method of protecting against or treating athrosclerosis in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before symptoms of atherosclerosis occur. In another embodiment, the compound is administered after the onset of symptoms of atherosclerosis.

Neuropathic Pain

The compounds of the invention or salts thereof are used in methods of treating, preventing, ameliorating neuropathic pain, such as chronic neuropathic pain, or a symptom thereof in a subject who is at risk of suffering from, is suffering from, or has suffered neuropathic pain. In one aspect, a polymorph of the invention is used in methods of treating, preventing, ameliorating neuropathic pain, such as chronic neuropathic pain, or a symptom thereof.

Neuropathic pain, also known as neuralgia, is qualitatively different from ordinary nociceptive pain. Neuropathic pain usually presents as a steady burning and/or "pins and needles" and/or "electric shock" sensations. The difference between nociceptive pain and neuropathic pain is due to the fact that "ordinary", nociceptive pain stimulates only pain nerves, while a neuropathy often results in the stimulation of both pain and non-pain sensory nerves (e.g., nerves that respond to touch, warmth, cool) in the same area, thereby producing signals that the spinal cord and brain do not normally expect to receive.

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury.

Neuropathic pain is diagnosed in a subject or patient using one or more of a variety of laboratory and/or clinical techniques known in the art, such as, for example, physical examination.

Compounds or salts useful in these methods of treating, preventing or ameliorating neuropathic pain, such as chronic neuropathic pain, or a symptom associated with neuropathic pain are compounds that modulate kinase signaling cascade involved in neuropathic pain.

c-Src has been shown to regulate the activity of N-methyl-D-aspartate (NMDA) receptors. (See Yu et al., Proc. Natl. Acad. Sci. USA, vol. 96:7697-7704 (1999), which is hereby incorporated by reference in its entirety). Studies have shown that PP2, a low molecular weight Src kinase inhibitor, decreases phosphorylation of the NMDA receptor NM2 subunit. (See Guo et al., J. Neuro., vol. 22:6208-6217 (2002), which is hereby incorporated by reference in its entirety). Thus, Src inhibition, which in turn, inhibits the activity NMDA receptors, may be useful in the prevention, treatment or amelioration of neuropathic pain, such as chronic neuropathic pain.

The compounds of the invention or salts thereof prevent, treat or ameliorate neuropathic pain, such as chronic neuropathic pain, or a symptom associated with neuropathic pain. Symptoms of neuropathic pain include shooting and burning pain, tingling and numbness.

The compounds of the invention or salts thereof are administered alone, in pharmaceutical compositions, or in combination with any of a variety of known treatments, such as, for example, analgesics, opioids, tricyclic antidepressants, anticonvulsants and serotonin norepinephrine reuptake inhibitors.

In one embodiment, the compound or salt is administered before the onset of chronic neuropathic pain. In another embodiment, the compound is administered after the onset of chronic neuropathic pain.

Another aspect of the invention includes a method of treating, preventing, ameliorating neuropathic pain or a symptom thereof, in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

Hepatitis B

The compounds of the invention or salts thereof are used in methods of treating, preventing, or ameliorating hepatitis B or a symptom thereof in a subject who is at risk for or suffering from hepatitis B. In one aspect, a polymorph of the invention is used in methods of treating, preventing, or ameliorating hepatitis B or a symptom thereof.

The hepatitis B virus, a member of the Hepadnavirus family, consists of a proteinaceous core particle containing the viral genome in the form of double stranded DNA with single-stranded regions and an outer lipid-based envelope with embedded proteins. The envelope proteins are involved in viral binding and release into susceptible cells. The inner capsid relocates the DNA genome to the cell's nucleus where viral mRNAs are transcribed. Three subgenomic transcripts encoding the envelope proteins are made, along with a transcript encoding the X protein. A fourth pre-genomic RNA is transcribed, which is exported to the cytosol and translates the viral polymerase and core proteins. Polymerase and pre-genomic RNA are encapsidated in assembling core particles, where reverse transcription of the pre-genomic RNA to genomic DNA occurs by the polymerase protein. The mature core particle then exits the cell via normal secretory pathways, acquiring an envelope along the way.

Hepatitis B is one of a few known non-retroviral viruses that employ reverse transcription as part of the replication process. Other viruses which use reverse transcription include, e.g., HTLV or HIV.

During HBV infection, the host immune response is responsible for both hepatocellular damage and viral clearance. While the innate immune response does not play a significant role in these processes, the adaptive immune response, particularly virus-specific cytotoxic T lymphocytes (CTLs), contributes to nearly all of the liver injury associated with HBV infection. By killing infected cells and by producing antiviral cytokines capable of purging HBV from viable hepatocytes, CTLs also eliminate the virus. Although liver damage is initiated and mediated by the CTLs, antigen-nonspecific inflammatory cells can worsen CTL-induced immunopathology and platelets may facilitate the accumulation of CTLs into the liver.

Hepatitis B is diagnosed in a patient using any of a variety of clinical and/or laboratory tests such as, physical examination, and blood or serum analysis. For example, blood or serum is assayed for the presence of viral antigens and/or antibodies produced by the host. In a common test for Hepatitis B, detection of hepatitis B surface antigen (HBsAg) is used to screen for the presence of infection. It is the first detectable viral antigen to appear during infection with this virus; however, early in an infection, this antigen may not be present and it may be undetectable later in the infection as it is being cleared by the host. During this 'window' in which the host remains infected but is successfully clearing the virus, IgM antibodies to the hepatitis B core antigen (anti-HBc IGM) may be the only serologic evidence of disease.

Shortly after the appearance of the HBsAg, another antigen named as the hepatitis B e antigen (HBeAg) will appear. Traditionally, the presence of HBeAg in a host's serum is associated with much higher rates of viral replication; however, some variants of the hepatitis B virus do not produce the "e" antigen at all. During the natural course of an infection, the HBeAg may be cleared, and antibodies to the "e" antigen (anti-HBe) will arise immediately afterward. This conversion is usually associated with a dramatic decline in viral replication. If the host is able to clear the infection, eventually the HBsAg will become undetectable and will be followed by antibodies to the hepatitis B surface antigen (anti-HBs). A person negative for HBsAg but positive for anti-HBs has either cleared an infection or has been vaccinated previously. A number of people who are positive for HBsAg may have very little viral multiplication, and hence may be at little risk of long-term complications or of transmitting infection to others.

Compounds or salts useful in these methods of treating, preventing or ameliorating hepatitis B or a symptom thereof are compounds or salts that modulate kinase signaling cascade in a patient at risk for or suffering from hepatitis B. In some embodiments, the compound or salt is a kinase inhibitor. For example, the compound or salt is a tyrosine kinase inhibitor. In an embodiment, the tyrosine kinase inhibitor is a Src inhibitor. Preferably, the compound or salt used in the methods of treating, preventing or ameliorating hepatitis B or a symptom thereof described herein is an allosteric inhibitor of kinase signaling cascade involved in hepatitis B. Preferably, the compound or salt used in the methods of treating, preventing or ameliorating hepatitis B or a symptom associated with hepatitis B described herein is a non-ATP competitive inhibitor of kinase signaling cascade involved in hepatitis B.

Src plays a role in the replication of the hepatitis B virus. The virally encoded transcription factor HBx activates Src in a step that is required from propagation of the HBV virus. (See, e.g., Klein et al., EMBO J., vol. 18:5019-5027 (1999); Klein et al., Mol. Cell. Biol., vol. 17:6427-6436 (1997), each of which is hereby incorporated by reference in its entirety). Thus, Src inhibition, which in turn, inhibits Src-mediated propagation of the HBV virus, may be useful in the prevention, treatment or amelioration of hepatitis B or a symptom thereof.

The compounds of the invention or salts thereof prevent, treat or ameliorate hepatitis B or a symptom associated with hepatitis B. Symptoms of hepatitis B typically develop within 30-180 days of exposure to the virus. However, up to half of all people infected with the hepatitis B virus have no symptoms. The symptoms of hepatitis B are often compared to flu, and include, e.g., appetite loss; fatigue; nausea and vomiting, itching all over the body; pain over the liver (e.g., on the right side of the abdomen, under the lower rib cage), jaundice, and changes in excretory functions.

The compounds of the invention or salts thereof are administered alone, in pharmaceutical compositions, or in combination with any of a variety of known treatments for hepatitis B, such as, for example, interferon alpha, lamivudine (Epivir-HBV) and baraclude (entecavir).

Another aspect of the invention includes a method of protecting against or treating hepatitis B in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

In one embodiment, the compound or salt is administered before the subject has contracted hepatitis B. In another embodiment, the compound or salt is administered after the subject has contracted hepatitis B.

Regulate Immune System Activity

As described herein, the compounds of the invention or salts thereof may be used to regulate immune system activity in a subject, thereby protecting against or preventing autoimmune disease, e.g., rheumatoid arthritis, multiple sclerosis, sepsis and lupus as well as transplant rejection and allergic diseases. Alternatively, the compound may be used to treat autoimmune disease in a subject. In one aspect, a polymorph of the invention may be used to regulate immune system activity in a subject. The compound or salt may result in reduction in the severity of symptoms or halt impending progression of the autoimmune disease in a subject.

The compound of the invention or salt thereof may be involved in modulating a kinase signaling cascade, e.g., a kinase inhibitor, a non-ATP competitive inhibitor, a tyrosine kinase inhibitor, e.g., a Src inhibitor, a p59fyn (Fyn) inhibitor or a p56lck (Lck) inhibitor.

Autoimmune diseases are diseases caused by a breakdown of self-tolerance such that the adaptive immune system responds to self antigens and mediates cell and tissue damage. Autoimmune diseases can be organ specific (e.g., thyroiditis or diabetes) or systemic (e.g., systemic lupus erythematosus). T cells modulate the cell-mediated immune response in the adaptive immune system. Under normal conditions, T cells express antigen receptors (T cell receptors) that recognize peptide fragments of foreign proteins bound to self major histocompatibility complex molecules. Among the earliest recognizable events after T cell receptor (TCR) stimulation are the activation of Lck and Fyn, resulting in TCR phosphorylation on tyrosine residues within immunoreceptor tyrosine-based activation motifs (Zamoyska, et al.; 2003, *Immunol. Rev.*, 191, 107-118). Tyrosine kinases, such as Lck (which is a member of the Src family of protein tyrosine kinases) play an essential role in the regulation of cell signaling and cell proliferation by phosphorylating tyrosine residues of peptides and proteins (Levitzki; 2001, *Top. Curr. Chem.*, 211, 1-15; Longati, et al.; 2001, *Curr. Drug Targets*, 2, 41-55; Qian, and Weiss; 1997, *Curr. Opin. Cell Biol.*, 9, 205-211). Thus, although not wishing to be bound by theory, it is hypothesized that the administration of a compound of the instant invention which modulates tyrosine kinase (e.g., Src) activity is useful in the treatment of autoimmune disease.

The tyrosine kinases lck and fyn are both activated in the TCR pathway; thus, inhibitors of lck and/or fyn have potential utility as autoimmune agents (Palacios and Weiss; 2004, *Oncogene*, 23, 7990-8000). Lck and Fyn are predominantly expressed by T cells through most of their lifespan. The roles of Lck and Fyn in T cell development, homeostasis and activation have been demonstrated by animal and cell line studies (Parang and Sun; 2005, *Expert Opin. The. Patents*, 15, 1183-1207). Lck activation is involved in autoimmune diseases and transplant rejection (Kamens, et al.; 2001, *Curr. Opin. Investig. Drugs*, 2, 1213-1219). Results have shown that the lck (−) Jurkat cell lines are unable to proliferate, produce cytokines, and generate increases in intracellular calcium, inositol phosphate, and tyrosine phosphorylation in response to T cell receptor stimulation (Straus and Weiss; 1992, *Cell.*, 70, 585-593; Yamasaki, et al.; 1996, *Mol. Cell. Blot.*, 16, 7151-7160). Therefore, an agent inhibiting lck would effectively block T cell function, act as an immunosuppressive agent, and have potential utility in autoimmune diseases, such as rheumatoid arthritis, multiple sclerosis, and lupus, as well as in the area of transplant rejection and allergic diseases (Hanke and Pollok; 1995, *Inflammation Res.*, 44, 357-371). Thus, although not wishing to be bound by theory, it is hypothesized that the administration of a compound of the instant invention or salt which modulates one or more members of the Src family of protein tyrosine kinases (e.g., lck and/or fyn) is useful in the treatment of autoimmune disease.

Another aspect of the invention includes a method of regulating immune system activity in a subject comprising administering a composition comprising an effective amount of a substantially pure KX2-391, or a salt, solvate, hydrate, or prodrug thereof, for example, substantially pure KX2-391, KX2-391•2HCl, or KX2-391•MSA. The invention includes administering an effective amount of a substantially pure polymorph of KX2-391•MSA e.g., Form A.

DEFINITIONS

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g. growth factor receptor PTKs) and the non-receptor PTKs (e.g. the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

"Inhibits one or more components of a protein kinase signaling cascade" means that one or more components of the kinase signaling cascade are effected such that the functioning of the cell changes. Components of a protein kinase signaling cascade include any proteins involved directly or indirectly in the kinase signaling pathway including second messengers and upstream and downstream targets.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the terms "psoriatic condition" or "psoriasis" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

"A therapeutically effective amount" means the amount of a compound or salt that, when administered to a mammal for treating a disease, is sufficient to effect such treatment for the disease. In one embodiment, a therapeutically effective amount is administered to a mammal to reduce reduce the level of the disease e.g., to reduce the level of hearing loss. In one embodiment, a therapeutically effective amount of a compound or salt is administered. In another embodiment, therapeutically effective amount of a composition is administered. The "therapeutically effective amount" will vary depending on the compound or salt, the disease and its severity and the age, weight, etc., of the mammal to be treated.

A therapeutically effective amount of one or more of the compounds or salts can be formulated with a pharmaceutically acceptable carrier for administration to a human or an animal. Accordingly, the compounds, salts or the formulations can be administered, for example, via oral, parenteral, or topical routes, to provide a therapeutically effective amount of the compound. In alternative embodiments, the compounds or salts prepared in accordance with the present invention can be used to coat or impregnate a medical device, e.g., a stent.

The term "prophylactically effective amount" means an effective amount of a compound or salt, of the present invention that is administered to effect prevention of the disease. In one embodiment, a prophylactically effective amount of a compound or salt is administered. In another embodiment, prophylatically effective amount of a composition is administered.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

Compounds of the present invention or salts thereof that contain nitrogens can be converted to N-oxides by treatment with an oxidizing agent (e.g., 3-chloroperoxybenzoic acid (m-CPBA) and/or hydrogen peroxides) to afford other compounds or salts of the present invention. Thus, all shown and claimed nitrogen-containing compounds or salts are considered, when allowed by valency and structure, to include both the compound or salt as shown and its N-oxide derivative (which can be designated as N→O or N$^+$—O$^-$). Furthermore, in other instances, the nitrogens in the compounds or salts of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds or salts are also considered, when allowed by valency and structure, to cover both the compound or salt as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

"Counterion" is used to represent a small, negatively charged species such as chloride, bromide, hydroxide, acetate, and sulfate.

An "anionic group," as used herein, refers to a group that is negatively charged at physiological pH. Anionic groups include carboxylate, sulfate, sulfonate, sulfonate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In one embodiment, an anionic group is a carboxylate.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds or salts described herein may have asymmetric centers. Compounds of the present invention or salts thereof containing an asymmetrically substituted atom may be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention or salts thereof are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds or salts are also considered to be part of the present invention.

In the present specification, the structural formula of the compound or salt represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

"Isomerism" means compounds or salts that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound or salt with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound or salt that has more than one chiral center has $2^{n-1}$ enantiomeric pairs, where n is the number of chiral centers. Compounds or salts with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds or salts discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds or salts whose structures differ markedly in arrangement of atoms, but which exist in easy and rapid equilibrium. It is to be understood that the compounds of the invention or salts thereof may be depicted as different tautomers. It should also be understood that when compounds have tautomeric forms, all tautomeric forms are intended to be within the scope of the invention, and the naming of the compounds or salts does not exclude any tautomer form.

Some compounds of the present invention or salts thereof can exist in a tautomeric form. Tautomers are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds or salts.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone—enol, amide—nitrile, lactam—lactim, amide—imidic acid tautomerism in heterocyclic rings (e.g. in the nucleobases guanine, thymine, and cytosine), amine—enamine and enamine—enamine.

It is to be understood accordingly that the isomers arising from asymmetric carbon atoms (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The compounds of this invention may exist in stereoisomeric form, therefore can be produced as individual stereoisomers or as mixtures.

A "pharmaceutical composition" is a formulation containing the disclosed compounds or salts thereof in a form suitable for administration to a subject. In one embodiment, the pharmaceutical composition is in bulk or in unit dosage form. It is can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the invention are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention or salt thereof include powders, sprays, ointments, pastes, creams, lotions, gels, solutions, patches and inhalants. In one embodiment, the active compound or salt is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound or salt from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound or salt from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, salts, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxylamine-containing, and imine-containing compounds of the present invention.

The compounds or salts of the present invention can be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds or salts of the present invention can be delivered in prodrug form. Thus, the present invention is intended to cover prodrugs of the presently claimed compounds and salts, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound or salt Prodrugs include compounds or salts of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds, and the like, See Bundegaard, H. "Design of Prodrugs" p1-92, Elesevier, New York-Oxford (1985).

"Protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

"Stable compound" and "stable structure" are meant to indicate a compound or salt that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

"Combination therapy" (or "co-therapy") includes the administration of a compound of the invention or salt thereof and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound or salt is administered orally. One skilled in the art will recognize the advantages of certain routes of administration.

The dosage regimen utilizing the compounds or salts is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention or salts thereof can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds or salts will be present in such pharmaceutical compositions in amounts sufficient to provide the desired dosage amount in the range described herein.

In one embodiment, the compound or salt is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds or salts, solvates, tautomers or polymorphs thereof, can be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds or salts are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds or salts as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

The active reagents can be prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The compositions and formulations of the instant invention can also comprise one or more desiccants. Suitable desiccants that can be used in the present invention are those that are pharmaceutically safe, and include, for example, pharmaceutical grades of silica gel, crystalline sodium, potassium or calcium aluminosilicate, colloidal silica, anhydrous calcium sulphate and the like. The desiccant may be present in an amount from about 1.0% to 20.0%, or from about 2% to 15% w/w (or any value within said range).

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention or salts thereof are also formulated as "pulsed release" formulations, in which the compound or salt is released from the pharmaceutical compositions in a series of releases (i.e., pulses). The compounds or salts are also formulated as "sustained release" formulations in which the compound or salt is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound or salt; mixing under appropriate conditions, e.g., heating, agitation, sonication, and the like; centrifuging or filtering the resulting mixtures to obtain clear solutions; and analyzing the solutions for concentration of the disclosed compound or salt.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Small Scale Synthesis of KX2-391

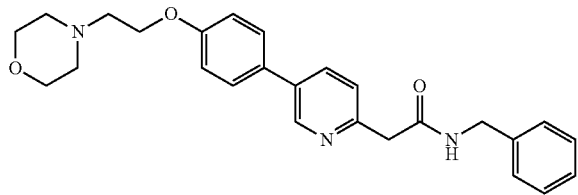 [SMILES: O=C(Cc1ccc(-c2ccc(OCCN3CCOCC3)cc2)cn1)NCc1ccccc1]

The preliminary synthesis described below was illustrated in US20060160800A1. This procedure is useful for small scale reactions, for example, reactions that produce up to 50 g of product.

For the following synthesis, unless otherwise noted, reagents and solvents were used as received from commercial suppliers. Proton and carbon nuclear magnetic resonance spectra were obtained on a Bruker AC 300 or a Bruker AV 300 spectrometer at 300 MHz for proton and 75 MHz for carbon. Spectra are given in ppm (δ) and coupling constants, J, are reported in Hertz. Tetramethylsilane was used as an internal standard for proton spectra and the solvent peak was used as the reference peak for carbon spectra. Mass spectra and LC-MS mass data were obtained on a Perkin Elmer Sciex 100 atmospheric pressure ionization (APCI) mass spectrometer. LC-MS analyses were obtained using a Luna C8(2) Column (100×4.6 mm, Phenomenex) with UV detection at 254 nm using a standard solvent gradient program (Method B). Thin-layer chromatography (TLC) was performed using Analtech silica gel plates and visualized by ultraviolet (UV) light, iodine, or 20 wt % phosphomolybdic acid in ethanol. HPLC analyses were obtained using a Prevail C18 column (53×7 mm, Alltech) with UV detection at 254 nm using a standard solvent gradient program (Method A or B).

Method A:

| Time (min) | Flow (mL/min) | % A | % B |
|---|---|---|---|
| 0.0 | 3.0 | 95.0 | 5.0 |
| 10.0 | 3.0 | 0.0 | 100.0 |
| 11.0 | 3.0 | 0.0 | 100.0 |

A = Water with 0.1 v/v Trifluoroacetic Acid
B = Acetonitrile with 0.1 v/v Trifluoroacetic Acid Method B:

| Time (min) | Flow (mL/min) | % A | % B |
|---|---|---|---|
| 0.0 | 2.0 | 95.0 | 5.0 |
| 4.0 | 2.0 | 5.0 | 95.0 |

A = Water with 0.02 v/v Trifluoroacetic Acid
B = Acetonitrile with 0.02 v/v Trifluoroacetic Acid Synthesis of N-benzyl-2-(5-bromopyridin-2-yl)acetamide

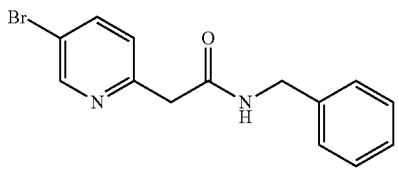 [SMILES: O=C(Cc1ccc(Br)cn1)NCc1ccccc1]

A flask was charged with 5-(5-bromopyridin-2(1H)-ylidene)-2,2-dimethyl-1,3-dioxane-4,6-dione (1.039 g, 3.46 mmol), benzylamine (0.50 mL, 4.58 mmol), and toluene (20 mL). The reaction was brought to reflux under nitrogen for 18 hours, then cooled and placed in a freezer until cold. The product was collected by filtration and washed with hexanes to yield a mass of bright white crystals (1.018 g, 96%).

Synthesis of 4-(2-(4-(4,4,5,5-tetramethyl[1,3,2]dioxaborolan-2-yl)-phenoxy)ethyl)morpholine

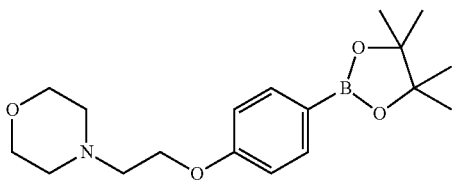 [SMILES: CC1(C)OB(c2ccc(OCCN3CCOCC3)cc2)OC1(C)C]

To a stirring solution of 4-(4,4,5,5-tetramethyl[1,3,2]dioxaborolan-2-yl)-phenol (2.55 g, 11.58 mmol), 2-morpholin-4-ylethanol (1.60 mL, 1.73 g, 13.2 mmol) and triphenyl phosphine (3.64 g, 13.9 mmol) in methylene chloride (60 mL) at 0° C. was added dropwise DIAD (2.82 g, 13.9 mmol). The reaction was allowed to warm to room temperature and stir overnight. After 18 hours, additional portions of triphenyl phosphine (1.51 g, 5.8 mmol), 2-morpholin-4-ylethanol (0.70 mL, 5.8 mmol), and DIAD (1.17 g, 5.8 mmol) were added.

After stirring an additional 2 hours at room temperature the reaction was concentrated and the residue purified by flash chromatography (5% to 25% EtOAc in CHCl₃) to provide the product as a white solid (2.855 g, 74%).

Synthesis of 2-(5-(4-(2-morpholinoethoxy)phenyl)pyridin-2-yl)-N-benzylacetamide KX2-391

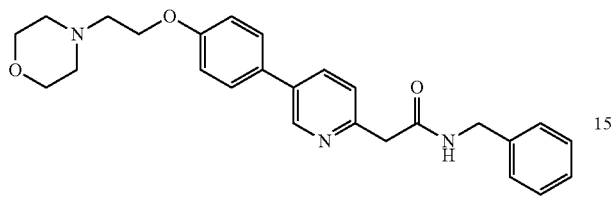

A 10 mL reaction tube with a septum closure and stir bar was charged with N-benzyl-2-(5-bromopyridin-2-yl)acetamide (123 mg, 0.403 mmol), 4-(2-(4-(4,4,5,5-tetramethyl[1,3,2]dioxaborolan-2-yl)-phenoxy)ethyl)morpholine (171 mg, 0.513 mmol), and FibreCat 1007 (30 mg, 0.015 mmol). Ethanol (3 mL) was added, followed by aqueous potassium carbonate solution (0.60 mL, 1.0 M, 0.60 mmol). The tube was sealed and heated under microwave conditions at 150° C. for 10 minutes. The reaction was cooled and concentrated to remove the majority of the ethanol, and then taken up in 10 mL of ethyl acetate and washed successively with water and saturated sodium chloride solution. The organic layer was dried with MgSO₄, filtered and concentrated to a white solid. This white solid was triturated with ethyl ether to give KX2-391 as a white solid (137 mg, 79%): mp 135-137° C.; ¹H NMR (300 MHz, CDCl₃) δ 8.70 (d, 1H, J=2.0 Hz), 7.81 (dd, 1H, J=2.4 Hz, J=8.0 Hz), 7.65 (br s, 1H), 7.49 (d, 2H, J=8.8 Hz), 7.37-7.20 (m, 6H), 7.01 (d, 2H, J=8.8 Hz), 4.49 (d, 2H, J=5.8 Hz), 4.16 (t, 2H, J=5.7 Hz, 3.82 (s, 2H), 3.78-3.72 (m, 4H), 2.84 (t, 2H, J=5.7 Hz), 2.62-2.58 (m, 4H); HPLC (Method B) 98.0% (AUC), $t_R$=1.834 min.; APCI MS m/z 432 [M+H]⁺.

Example 2

Intermediate Scale Synthesis of KX2-391 Di-Hydrochloride

The synthesis outlined in this example can be used on intermediate-scale reactions. The preparation of batches of at least 50 g of the dihydrochloride salt of KX2-391 is shown in Scheme 1. The linear synthesis consisted of 6 steps, a seventh step being the preparation of one of the reagents, 6-fluoropyridin-3-ylboronic acid (which is also available commercially). The overall yield of the sequence was 35% with an average yield of 83%, with the lowest yielding step being that of 68%. Of the seven steps only one required chromatography. The procedure listed below was performed on a 70 g scale.

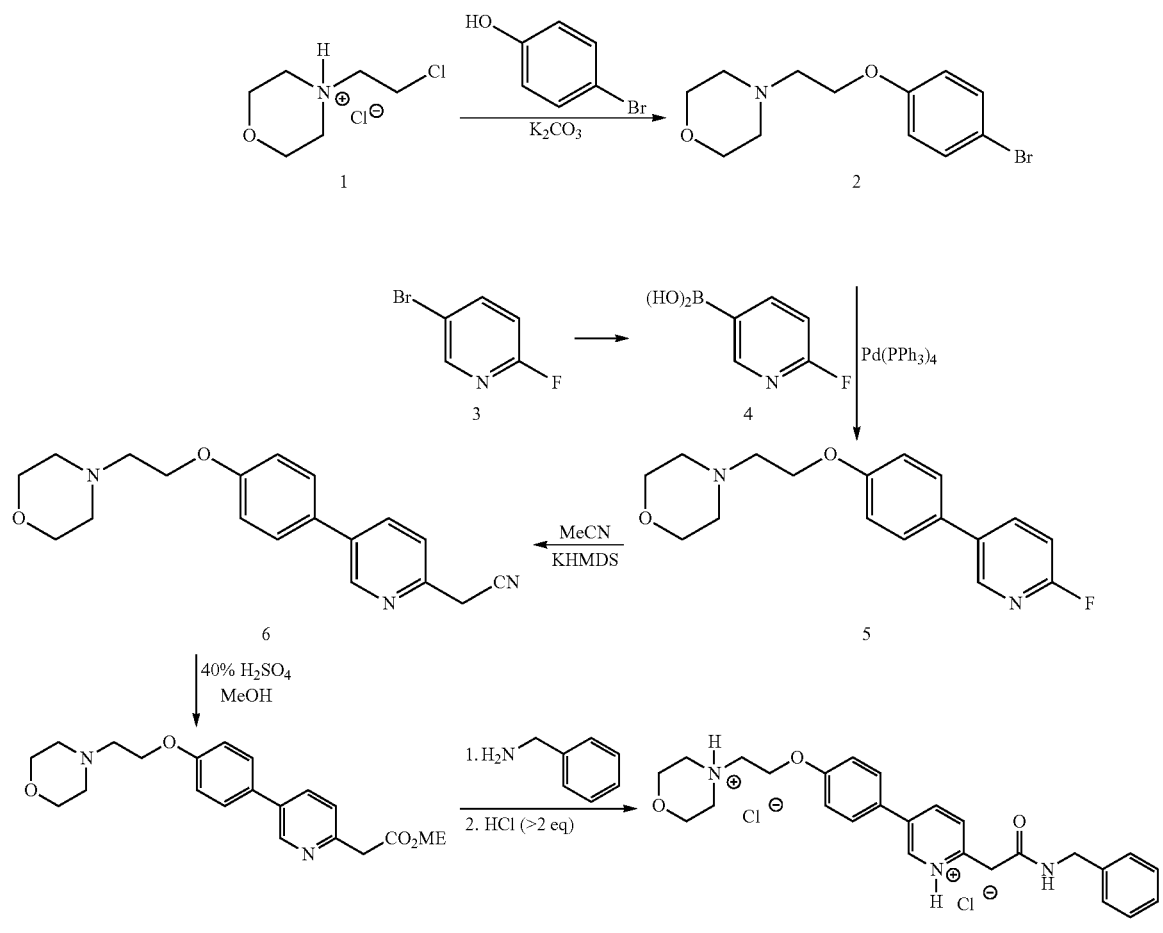

The first step is a Williamson ether synthesis between 4-bromophenol (131 g) and N-chloroethylmorpholine (1 as the HCl salt; 141 g) using $K_2CO_3$ powder (3 to 3.5 equivalents) as the base and having acetonitrile as the solvent. The ingredients were mixed and stirred at reflux overnight with high conversion (96.3-99.1%). After dilution with dichloromethane and heptane, the reaction mixture was filtered and evaporated to give the desired product 2 in essentially a quantitative yield (216 g). Note that with similar substrates (e.g., 4-bromo-3-fluorophenol), conversions (even with extensive heating) were not always so high (e.g., 59.9-98.3%). Both the alkyl chloride and the $K_2CO_3$ are preferably purchased from Aldrich. If continued heating does not drive reaction to completion, unreacted bromophenol can readily be removed by dissolving the crude reaction mixture in 4 parts toluene and washing out the phenol with 4 parts 15% aqueous NaOH.

One of the reagents required for the second step (Suzuki coupling) was 6-fluoropyridin-3-ylboronic acid (4). Although available commercially, this reagent was readily prepared by lithium-bromide exchange of 5-bromo-2-fluoropyridine (3, 102 g) with n-butyllithium (1.2 eq) at low temperatures (<−60° C.) in TBME followed by the addition of triisopropylborate (1.65 eq). Both stages of the reaction are brief, with an overall reaction time (including addition times) of ~3 h. Quenching is achieved with aqueous 24% NaOH, which also extracts the product leaving impurities in the organic layer. Once the aqueous layer is removed, it is then neutralized with HCl and extracted with EtOAc. After drying the organics and diluting with some heptane, concentration leads to precipitation/crystallization of the product. Filtration gave the boronic acid 4 in relatively high purity (96.4% AUC) and good yield (69 g, 79-90%; see note on estimation of yield in the experimental section), which can be used without further purification.

The second reaction step in the linear sequence (a Suzuki coupling) is a simple reaction to set up; all the reagents [2 (111 g), aqueous $Na_2CO_3$, DME, and $Pd(PPh_3)_4$ (0.04 eq)] were charged to the reaction flask and the mixture heated at reflux; note that the reaction mixture was degassed to remove oxygen. Once the reaction is complete (within 7 h), the work-up involved decanting (or siphoning off) of reaction solution from the organic salts on the side of the flask (there was no visible aqueous layer), the flask was rinsed, and dried, and the solvent was removed from the combined organics. Crystallization of crude 5 from isopropanol/heptane provided material of improved purity compared to the crude, but still required chromatography (ratio of silica gel to crude was ~8.5:1) to obtain material of adequate purity (>98%); the yield was 68% (79.5 g). Use of clean 5 prevented the need for chromatography in the next step, acetonitrile displacement of the fluorine atom.

The replacement of fluoride with acetonitrile was also a simple reaction, and a simple room temperature crystallization of the crude product provided clean 6 in high yield and purity. The reaction involved initial formation of the "enolate" from acetonitrile (6.5 eq) using potassium hexamethyldisilane KHMDS (8 eq)/THF at −10° C. followed immediately by the addition of fluoride 5 (79 g). The reaction was quick and after one hour quenching was achieved with saturated brine. After drying and evaporation of solvent of the organics, the resulting crude mixture consisted of only two components, the desired product and a much less polar product from apparent self-condensation of acetonitrile. The crude mixture was swirled in isopropanol/heptane and allowed to sit overnight, which resulted in complete crystallization of the product, which was filtered off and washed to provide high purity 6 (99.3% AUC) in good yield (64 g, 76%).

Methanolysis of 6 (64 g) was accomplished by heating in 40% $H_2SO_4$ (in MeOH) until the reaction was complete (25 h). The reaction was then cooled, stirred with $MgSO_4$ to convert traces of hydrolyzed product ($ArCH_2-CO_2Me$) back to product, and then added to cooled, aqueous $K_2CO_3$, with simultaneous extraction into dichloromethane. Drying and evaporation of most of the DCM followed by addition of 5% EtOAc (in heptane) and further concentration resulted in the crystallization of the product, Filtration of the solid and washing gave high purity (98.9% AUC) 7 in good yield (82%), additional high purity product (4 g) being obtained from the mother liquors for a total yield of 61.7 g (87%).

The amidation step also involved charging of the reaction vessel with the ingredients (7 (61 g), benzyl amine (3 eq), and high boiling anisole) and then heating at reflux until the reaction was complete. Cooling of the reaction mixture resulted in complete crystallization of the target compound with high purity (98.9%) and good yield (81%).

The final step was the formation of the dihydrochloric salt of the target compound. In order to ensure complete protonation at both basic sites, the reaction was conducted in absolute ethanol, which freely dissolved the dihydrochloride salt. After evaporation to near dryness, the reaction mixture was "chased" with ethanol twice to remove excess hydrogen chloride. The resulting viscous oil was dissolved in ethanol (2 parts) and then added, with rapid stirring, to a large volume (20 parts) EtOAc (ethyl acetate). Filtration, washing with ethyl acetate (no heptane) and vacuum drying provided the dihydrochloride salt of KX2-391 as a creamy-white powder. A total of 68 g (yield of 97%) was obtained of the final salt in high purity (99.6% AUC), which contained traces of EtOAc (4.8% w/w), EtOH (0.3% w/w), and heptane (0.6% w/w; from a final wash with heptane prior to vacuum drying). This salt was also crystallized (instead of the precipitation method described above) from hot EtOH/EtOAc to afford crystalline beads that had much lower entrapped solvent levels (only 0.26% w/w of EtOAc and 0.45% w/w of EtOH) and was free-flowing.

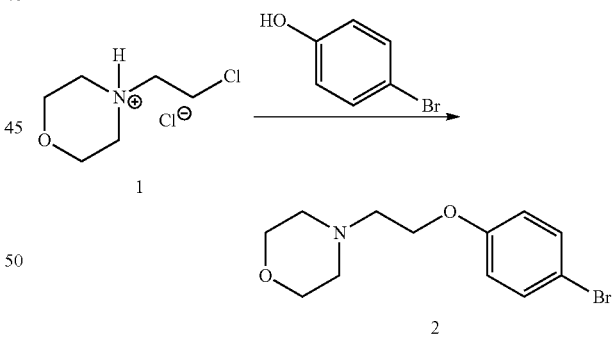

Preparation of 4-(2-(4-bromophenoxy)ethyl)morpholine (2)

A 5 L three-necked round-bottomed flask, equipped with mechanical stirrer, thermometer with adapter, condenser, and nitrogen inlet (on top of condenser), was charged with 1 (140.7 g, 0.756 mol), 4-bromophenol (130.6 g, 0.755 mol), anhydrous $K_2CO_3$ powder (367.6 g, 2.66 mol, 3.5 eq), and acetonitrile (1.3 L). The mixture was vigorously stirred (blade touching bottom of flask) at 80° C. (overnight), followed by dilution with DCM (500 mL) and heptane (200 mL) and filtration through Celite. Evaporation to dryness (rotovap, then high vac) gave 2 as a light yellow oil (216.00 g, yield of 100%, 96.3% AUC, contains 3.7% unreacted bromophenol). This material was used successfully without further purification.

¹H NMR (CDCl₃) δ 2.57 (t, 4H), 2.79 (t, 2H), 3.73 (t, 4H), 4.08 (t, 2H), 6.78 (d, 2H), 7.37 (d, 2H). MS (from LC/MS): m/z 287.1 [M+1].

That the bromophenol can be readily removed was demonstrated on a 2 g sample by first dissolving the sample in toluene (8 g) and washing with 8 g of 15% aqueous NaOH; liquid chromatography showed no trace of unreacted bromophenol in the recovered product (1.97 g; 98.5% recovery).

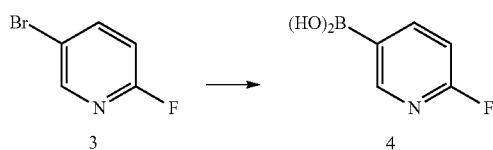 [SMILES: Fc1ccc(Br)cn1 ; OB(O)c1ccc(F)nc1]

Preparation of 6-fluoropyridin-3-ylboronic acid (4)

To stirred and cooled (dry ice-acetone bath) anhydrous [TBME] (620 mL; in a 3 L three-necked round-bottomed flask equipped with mechanical stirrer, temperature probe with adapter, and nitrogen inlet) was added (via syringe) 2 M BuLi (352 mL, 0.704 mol, 1.2 eq). To this rapidly stirred and cooled (<−75° C.) mixture was added a solution of 3 (102.2 g, 0.581 mol) in anhydrous TBME (100 mL) over a period of 13 min during which time the internal temperature rose to −62° C. The reaction was stirred for another 45 min (the temperature was maintained between −62° C. and −80° C.), followed by the rapid and sequential addition of four portions of triisopropylborate (total of 180 g, 0.957 mol, 1.65 eq). At the end of the addition the internal temperature had risen to −33° C. After stirring an additional 45 min over the cold bath (internal temperature lowered from −33° C. to −65° C.), the cold bath was removed and the stirred mixture on its own rose to −22° C. over a period of 50 min. After warming (via water bath) to 6° C. over a period of 15 min, the stirred reaction mixture was placed in an ice-water bath and then quenched under nitrogen with a cooled solution of NaOH (160 g) in water (500 mL). Once the addition was complete, the internal temperature was 20° C. This mixture was stirred at room temperature for 1.5 h. The aqueous layer was removed, neutralized to pH 7 with ~350 mL concentrated HCl, and then extracted with EtOAc (3×1 L). Because the pH was now 8-9, the aqueous layer was adjusted to pH 7 using ~15 mL concentrated HCl and extracted further (2×1 L) with ethyl acetate. The combined EtOAc extracts were dried (Na₂SO₄), filtered, and concentrated to a volume of ~150 mL. With swirling of the concentrate, heptane was added in portions (total volume of 300 mL) resulting in the precipitation/crystallization of the product. Filtration, washing of the solid with heptane (100 mL, 300 mL, then another 300 mL), and air drying gave the title product as an off-white solid (68.6 g, yield of 79-90%*; LC purity of 96.4%, NMR showed an estimated 5.5% w/w of heptane), which was used successfully without further purification. LC/MS showed it to be a mixture of the two following entities, the intensity of the higher molecular weight entity being major (*Note: yield of reaction is 79% if the boronic acid is assumed to be the only constituent and is 90% if it is assumed that the cyclic borate is the only constituent):

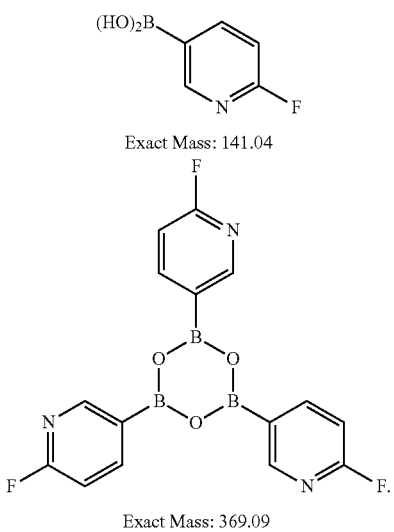

¹H NMR (CDCl₃) δ 7.14 (dd, 1H), 8.27 (ddd, 1H), 8.39 (br s, 2H, 20H), 8.54 (fine d, 1H). MS (from LC/MS): m/z 143.0 [M+1; for boronic acid] and 370.0 [M+1; for cyclic borate above].

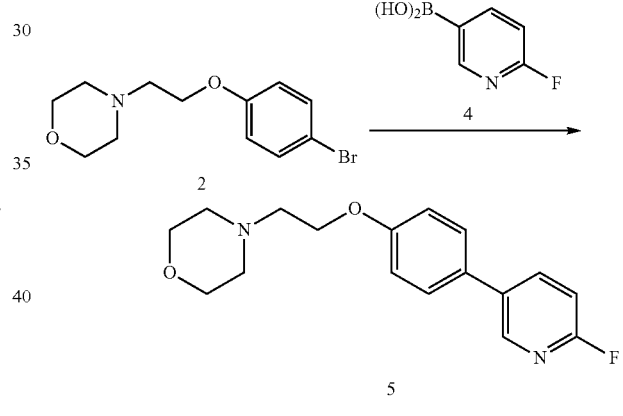

Preparation of 4-(2-(4-(6-fluoropyridin-3-yl)phenoxy)ethyl)morpholine (5)

A 2 L three-necked round-bottomed flask equipped with mechanical stirrer, thermometer and adapter, condenser, and nitrogen inlet (at top of condenser) was charged with 2 (110.7 g, 0.387 mol), 4 (71.05 g, 0.477 mol, 1.23 eq) and DME (700 mL). The resulting stirred solution was degassed by passing a rapid stream of nitrogen through the stirred solution over a period of 5 min followed by the addition of a degassed solution of Na₂CO₃ (121.06 g, 1.142 mol, 3 eq) in H₂O (250 mL) and also solid Pd(PPh₃)₄ (19.8 g, 0.044 eq). Immediately after the last addition, the head space above the reaction mixture was purged with nitrogen and the mixture then stirred at 80-85° C. (internal temperature) for 7 h, followed by cooling to room temperature. Because of the lack of an aqueous layer, the supernatant was decanted, leaving behind the inorganic salts (with adsorbed water). The reaction flask with the inorganic salts was washed with 50% dichloromethane/ethyl acetate (2×250 mL), the washes being added to the decanted supernatant. These combined organics were dried (Na₂SO₄), filtered, and evaporated to dryness to a dark brown oil (148 g). To this oil was added 150 g of 50% heptane/isopropyl alcohol (IPA) and after swirling and cooling (via ice water bath), crystallization began. Additional heptane (50 g) was added and the resulting solid was filtered, washed, and air dried to give 48 g of a light brown solid. After evaporating the filtrate to dryness, the resulting mixture was swirled in 100 mL of 50% heptane/IPA followed by the addition of more heptane (~100 mL), stoppering and placing in the freezer for crystallization. The resulting solid was filtered, washed with heptane, and air dried to give 61 g of a gummy solid. Evaporation of the resulting filtrate gave an oil (34 g) which contained significant less polar impurities including $Ph_3P=O$ and so it was partitioned between 2 N HCl (240 mL) and EtOAc (220 mL). The bottom aqueous layer was removed and then stirred with EtOAc while neutralizing with $K_2CO_3$ to a pH of 7-8. The EtOAc layer was dried, filtered, and evaporated to dryness (22 g). The 48 g, 61 g, and 22 g portions were chromatographed over silica gel (1.1 Kg) packed in DCM. Elution with DCM (400 mL), 50% DCM/EtOAc (5 L), and then 50% DCM/EtOAc (8 L) containing increasing amounts of MeOH/$Et_3N$ (beginning with 1.5% MeOH/1% $Et_3N$ and ending with 5% MeOH/3% $Et_3N$) gave 77.68 g of a viscous oil (purity 98.0%) which immediately crystallized upon swirling in heptane (300 mL). Filtration, washing with heptane and air drying gave 75.55 g (98.7% AUC) of solid 5. Additional pure 5 (total of 3.9 g, 98.6-99.3% AUC) was obtained from earlier chromatographic fractions containing $Ph_3P=O$ by cleaning them up as done for the above 34 g sample, followed by evaporative crystallization. The total yield of 5 was 79.5 g (68%).

$^1$H NMR (CDCl$_3$) δ 2.59 (t, 4H), 2.84 (t, 2H), 3.75 (t, 4H), 4.16 (t, 2H), 6.97 (dd, 1H), 7.01 (d, 2H), 7.46 (d, 2H), 7.92 (ddd, 1H), 8.37 (fine d, 1H). MS (from LC/MS): m/z 303.2 [M+1].

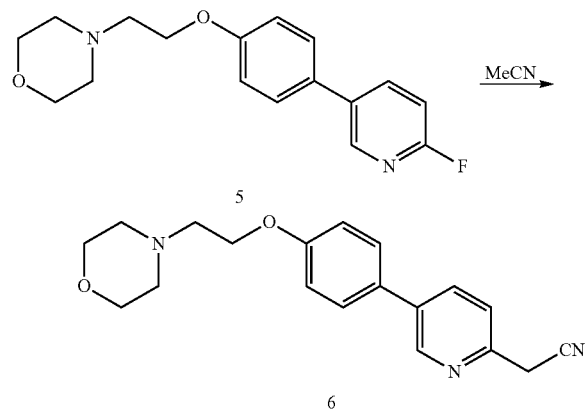

Preparation of 2-(5-(4-(2-morpholinoethoxy)phenyl)pyridin-2-yl)acetonitrile (6)

A 3 L three-necked round-bottomed flask was equipped with mechanical stirrer, thermometer and adapter, additional funnel, and nitrogen inlet (on top of addition funnel, positive pressure through a bubbler). With a rapid stream of nitrogen going through the bubbler, the stopper was removed and the flask was charged with KHMDS (415.8 g, 2.08 mol) and then anhydrous THF (1 L). To the stirred and cooled (ice/methanol bath, internal temperature of solution was −8° C.) KHMDS/THF solution was added dropwise a solution of MeCN (70 g) in THF (110 mL) over a period of 22 min followed immediately by the relatively rapid (4 min) addition of a solution of 5 (79.06 g, 0.262 mol) in THF (400 mL), after which time the internal temperature of the reaction mixture had reached 10° C. With continued cooling (1 h) the internal temperature was −6° C. and by TLC the reaction appeared complete. After an additional 30 min (internal temperature of −3° C.), the reaction mixture was quenched with saturated brine (1 L) and diluted with EtOAc (500 mL). After removing the aqueous layer, the organic solution was dried (Na$_2$SO$_4$), filtered, and evaporated to dryness (to an oil) followed by completely dissolving in IPA (150 mL), diluting with heptane (300 mL), adding seed crystals (prepared by dissolving ~100 mg of crude oil in IPA (~150 mg) and diluting with heptane (~2.5 mL)), and allowing to stand overnight. After stirring to break up the crystalline solid, the solid was filtered, washed with 250 mL 2:1 heptane/IPA and then multiple washes with heptane and air dried to give 64.38 g (yield of 76%) of title product 6 as a crystalline tan solid (LC purity of 99.3%). Another 5.88 g of less pure material was obtained from the filtrate.

$^1$H NMR (CDCl$_3$) δ 2.59 (t, 4H), 2.84 (t, 2H), 3.74 (t, 4H), 3.97 (s, 2H), 4.17 (t, 2H), 7.02 (d, 2H), 7.46 (d, 1H), 7.51 (d, 2H), 7.87 (dd, 1H), 8.77 (fine d, 1H). MS (from LC/MS): m/z 324.4 [M+1].

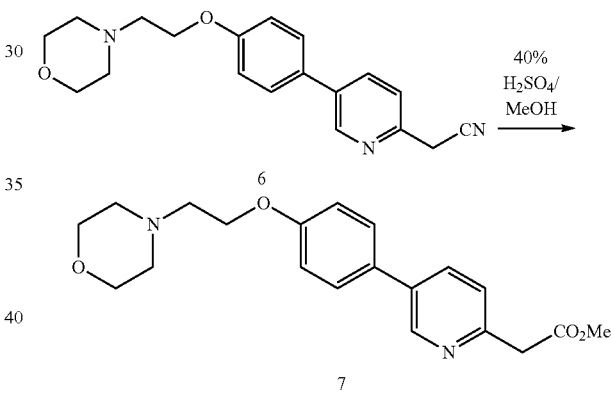

Preparation of methyl 2-(5-(4-(2-morpholinoethoxy)phenyl)pyridin-2-yl)acetate (7)

A 2 L single-necked round-bottomed flask was charged with 6 (64.00 g, 0.198 mol) and MeOH (360 g) followed by the slow, careful, and dropwise addition of H$_2$SO$_4$ (240 g) and the resulting homogeneous solution stirred at reflux (115° C. oil bath) until the reaction was complete (25 h with 0.8% unreacted starting material) with 3.5% ArCH$_2$CO$_2$H. After brief cooling, MgSO$_4$ (75 g) was added and the mixture swirled and allowed to stand an additional 45 min (composition now 96.3% product, 0.8% unreacted starting material, and 2.5% ArCH$_2$CO$_2$H). The reaction mixture was then added slowly to a rapidly stirred and cooled (ice-water bath) mixture of DCM (2 L) and a solution of K$_2$CO$_3$ (450 g) in H$_2$O (600 mL). The resulting emulsion was allowed to stand overnight. The clear portions of organic solution were siphoned off and the remainder portions were treated iteratively with water and DCM, the clear organics being combined with the original portion that was siphoned off. The combined organics were dried (Na$_2$SO$_4$), filtered, and concentrated to a volume of ~1.2 L followed by the addition of 300 mL of 5% EtOAc (in heptane) and then heptane (300 mL) and the mixture concentrated (rotovap with heat) again to remove the DCM. At this point 15 mL EtOAc was added and the hot mixture swirled until crystallization had begun, swirling continued until crystallization was near complete, and then allowed to stand and cool to room temperature for complete crystallization. The solid was then filtered, washed with 300 mL 5% EtOAc (in heptane) and heptane (100 mL) and then fully air dried to give 57.74 g (yield of 82%) of 7 as a light yellow solid (98.9% AUC). Another 3.94 g of clean product (97.9% AUC) was obtained from the filtrate (total yield of 87%).

$^1$H NMR (CDCl$_3$) δ 2.60 (t, 4H), 2.84 (t, 2H), 3.74 (overlapping t and s, 6H), 3.89 (s, 2H), 4.17 (t, 2H), 7.01 (d, 2H), 7.34 (d, 1H), 7.49 (d, 2H), 7.80 (dd, 1H), 8.74 (fine d, 1H). MS (from LC/MS): m/z 357.4 [M+1].

3 eq), and anhydrous anisole (300 g) and then stirred at reflux until reaction was essentially complete (23 h, 165° C. oil bath temperature; internal temperature was 147° C.) aid then allowed to cool to near room temperature. A portion (1 mL) of the reaction mixture was diluted with toluene (1 mL) resulting in the complete crystallization of that portion. This seed was then added to the reaction mixture and allowed to stand until the whole reaction mixture had crystallized to a single block. Toluene (150 mL) was added and the mixture swirled to break up the solid. Heptane/toluene (1:1, 100 mL) was added and the solid mixture broken up further. Finally, heptane (50 mL, then 25 mL) was added and the mixture broken up even further, allowing to stand an additional 30 min before filtering the solid. Filtration of the solid, washing with 2:1 toluene/heptane (300 mL), 1:2 toluene/heptane (300 mL), and then

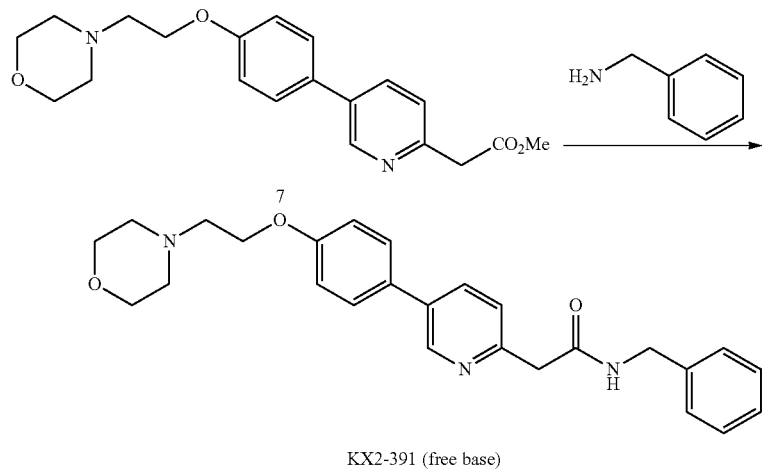

Preparation of 2-(5-(4-(2-morpholinoethoxy)phenyl)pyridin-2-yl)-N-benzylacetamide (KX2-391 free base)

A 1 L single-necked round-bottomed flask was charged with 7 (61.4 g, 0.172 mol), benzyl amine (55.6 g, 0.519 mol, heptane (2×300 mL), and then drying (air, then high vac) gave 60.16 g (yield of 81%) of title product as a white solid (≥98.9% AUC). Another 2.5 g of less pure (97.4%) material was obtained from the mother liquors.

$^1$H NMR (CDCl$_3$) δ 2.60 (t, 4H), 2.83 (t, 2H), 3.74 (t, 4H), 3.82 (s, 2H), 4.18 (t, 2H), 4.49 (d, 2H), 7.01 (d, 2H), 7.2-7.35 (m, 6H), 7.49 (d, 2H), 7.64 (br t, 1H), 7.81 (dd, 1H), 8.69 (fine d, 1H). MS (from LC/MS): m/z 432.5 [M+1].

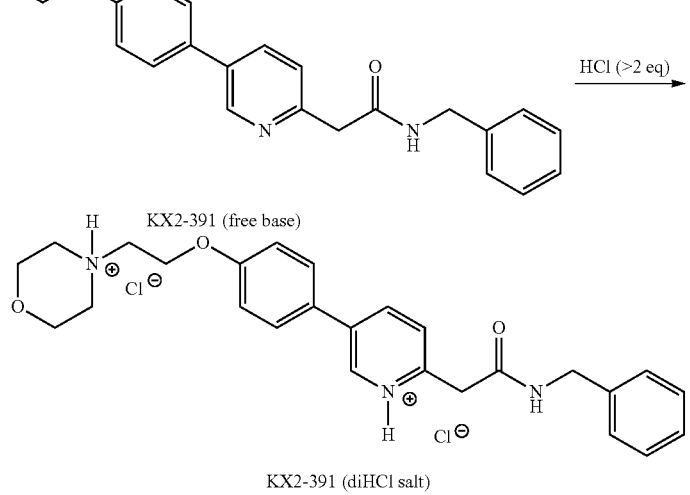

Preparation of 4-(2-(4-(6-(2-(benzylamino)-2-oxoethyl)pyridinium-3-yl)phenoxy)ethyl)-morpholin-4-ium chloride (KX2-391, diHCl salt)

To a stirred suspension of KX2-391 (free base, 60.00 g) in absolute EtOH (600 mL) was added 170 mL of 2.5 M HCl (in ethanol), 25 mL EtOH being added to wash down the sides of the flask. The resulting homogeneous solution was stirred at room temperature (20 min) and then evaporated to near dryness (to frothing). After chasing with EtOH (2×150 mL), the residue was taken up again in EtOH (150 mL) and then was followed by the slow addition of heptane until the mixture appeared saturated (33 mL required for cloudiness to remain). After sitting overnight, two layers had formed. After adding additional heptane (250 mL) crystallization still could not be induced and so the reaction mixture was concentrated to a volume of ~200 mL at which time the mixture was homogeneous. This thick homogeneous solution was added dropwise to very rapidly stirred (mechanical) EtOAc (2 L). After the addition was complete, a 25 mL EtOH rinse of the original flask and addition funnel was added to the rapidly stirred mixture. The rapid stirring was continued for another ~1 h and then the mixture was filtered and the solid (partly gummy) was washed with EtOAc (300 mL) and then heptane. As soon as the heptane wash began, the solid got much gummier. The fitted Buchner funnel and its contents were covered (paper towel/rubber band) and immediately placed in the vacuum oven. After overnight vacuum at ~45° C., the vacuum was released under nitrogen, and the Buchner funnel containing the product (foamy solid) was immediately placed in a ziplock back and then, under nitrogen (glove bag), transferred to a bottle and the foamy solid broken up (spatula) to a powder. A second night under high vacuum (~45° C.) resulted in only 1.3 g of additional weight loss. Constant weight was essentially attained with the third night of high vacuum (~45° C.) where only 0.2 g of weight was lost. The final weight of material was 68.05 g (yield of 97%), containing 0.29 eq (4.8% w/w) of EtOAc, 0.035 eq (0.3% w/w) EtOH, and 0.03 eq (0.6% w/w) heptane. The purity was 99.6%.

$^1$H NMR (DMSO-$d_6$) δ 3.1-3.3 (m, 2H), 3.45-3.65 (m, 4H), 3.8-4.0 (m, 4H), 4.11 (s, 2H), 4.32 (d, 2H), 4.57 (t, 2H), 7.19 (d, 2H), 7.2-7.4 (m, 5H), 7.88 (d, 2H), 7.93 (d, 1H), 8.68 (dd, 1H), 8.99 (br t, 1H), 9.10 (fine d, 1H), 11.8 (br s, 1H). MS (from LC/MS): m/z 432.5 [M+1 of free base].

Elemental analysis (for $C_{26}H_{29}N_3O_3 \cdot 2HCl \cdot 0.035EtOH \cdot 0.29EtOAc \cdot 0.03heptane \cdot 0.8H_2O$):

Calculated (%): C, 60.03; H, 6.54; N, 7.65; Cl, 12.91

Observed (%): C, 59.85/59.97; H, 6.54/6.47; N, 7.67/7.67; Cl, 13.10/13.24

Calculated FW: 534.63 (does not take into account the 0.8H$_2$O which probably arose during handling of this very hygroscopic powder, since $^1$H NMR shows no evidence for H$_2$O).

The ethyl chloride level in this material was measured and found to be 98 ppm. The sample was also analyzed and found to contain 5,800 ppm of heptane.

Analysis of another portion of this sample yielded the following results: 99.6% AUC, 1640 ppm ethanol, 41,480 ppm ethyl acetate, 5600 ppm heptane, no anisole detected, and 120 ppm ethyl chloride.

A procedure for recrystallizing the salt was also developed using the above dried salt. This procedure would work just was well on the highly pure crude salt (containing residual EtOH) obtained from concentrating the HCl salt-forming reaction mixture:

The salt (575 mg) was dissolved in twice the mass of absolute EtOH (1.157 g) and then heated under nitrogen. To this hot solution (stirred) was added 1.6 g of 25% EtOH (in EtOAc) followed by the addition of EtOAc (0.25 mL) resulting in a cloudiness that remained. The cloudy hot solution was allowed to cool to room temperature during which time crystallization occurred. After crystallization was complete (2 h), the crystalline solid was filtered, washed with anhydrous EtOAc (~40 mL), and vacuum dried to give 424 mg of the dihydrochloride salt of KX2-391 as a free-flowing solid (tiny beads, 99.8% AUC) containing only 0.05 eq (0.45% w/w) of EtOH and 0.015 eq (0.26% w/w) of EtOAc. Slightly better recovery (460 mg from 586 mg) was attained using isopropanol/EtOAc but the level of solvent entrapment was higher [0.085 eq (1.0% w/w) of isopropanol and 0.023 eq (0.4% w/w) of EtOAc].

Example 3

Large Scale Synthesis of KX2-391 Di-HCl

Reagents and solvents were used as received from commercial suppliers. Progress of the reactions was monitored by HPLC, GC/MS, or $^1$H NMR. Thin-layer chromatography (TLC) was performed using Analtech silica gel plates and visualized by UV light (254 nm). High pressure liquid chromatography (HPLC) was performed on an Agilent 1100 Series instruments. Proton and carbon nuclear magnetic resonance spectra were obtained using a Bruker AV 300 at 300 MHz for proton and 75 MHz for carbon. The solvent peak was used as the reference peak for proton and carbon spectra.

Preparation of
4-(2-(4-Bromophenoxy)ethyl)morpholine (2)

A 50 L jacketed reactor equipped with a reflux condenser and temperature probe was charged with 4-(3-chloropropyl)morpholine (2.44 kg, 0.54 mol), 4-bromophenol (2.27 kg, 0.54 mol, 1.0 equiv.), powdered potassium carbonate (6.331 kg, 1.88 mol, 3.50 equiv.), and DMF (12.2 L) and stirred. The reaction mixture was then heated to 60-65° C. and stirred overnight. After 17.5 h, the reaction mixture was cooled to 20-25° C. The reaction mixture was charged to a different reactor equipped with bottom valve for the work-up. While maintaining a temperature between 20-30° C., DI water (48.7 L) was charged to the reactor. The phases were separated. The aqueous layer was extracted with MTBE (3×24.4 L). To the combined organics, DI water (18.3 L) and then 6M sodium hydroxide (18.2 L) were added. The mixture was stirred for 2-5 minutes and the phases were separated. The organic phase was washed with water (24.4 L) and brine (24.4 L), dried over magnesium sulfate, filtered, and concentrated to give 3370 g of a yellow oil (89% crude yield, 99.4% AUC by HPLC).

Preparation of 6-fluoropyridin-3-ylboronic acid (4)

A 72 L reactor equipped with reflux condenser, and temperature probe. To the reactor 5-bromo-2-fluoropyridine (1.17 L, 0.568 mol), toluene (18.2 L), and triisopropyl borate (3.13 L, 0.68 mol, 1.2 equiv.) were charged and stirred. Tetrahydrofuran (4.4 L) was added to the reactor and the reaction mixture was cooled to between −35 to −50° C. While maintaining a temperature between −35 to −45° C., n-butyl lithium (2.5 M solution of hexanes, 5.44 L, 0.68 mol, 1.2 equiv.) was cautiously added to the reactor. After 5 h, the reaction was deemed complete and the reaction mixture was warmed to between −15 to −20° C. To the reaction was added 2M HCl (11.80 L) to the reactor while maintaining a temperature between −15° C. and 0° C. The reaction mixture was stirred at 18 to 23° C. for (16 h) and the phases were separated. The organics were then extracted with 6 M sodium hydroxide (6.0 L). The acidic anbasic aqueous phases were mixed in the reactor and 0.6 M HCl (2.5 L) was added until pH 7.5 was achieved. Sodium chloride (6.0 kg) was then added to the aqueous phase. The aqueous phase was then extracted with THF (3×20 L). The combined organics were dried with magnesium sulfate and concentrated to give 1300 g of a tan solid (81% crude yield).

Preparation of 4-(2-(4-(6-fluoropyridin-3-yl)phenoxy)ethyl)morpholine (5)

A 72 L reactor equipped with reflux condenser, sparging tube, bubbler, and temperature probe was charged with 6-fluoropyridin-3-ylboric acid (2.84 kg, 1.24 equiv.), 4-(2-(4-bromophenoxy)ethyl)morpholine (4.27 kg, 1.0 equiv.), and DME (27 L). Agitation was started and sodium carbonate (4.74 kg, 3.0 equiv.) as a solution in DI water (17.1 L) was then charged to the reaction mixture. Argon was bubbled through the reaction mixture for 50 minutes. Under an argon atmosphere, tetrakis(triphenylphosphine)palladium (750 g, 0.04 equiv.) was added to the reaction mixture as a slurry in DME (1.0 L). The reaction mixture was heated to 75-85° C. and stirred overnight (17 h). The reaction mixture was cooled to between 18-22° C. DI water (26.681 kg) and MTBE (26.681 L) were charged to the reactor and stirred for 5 minutes. The phases were separated and the aqueous phase was extracted with MTBE (2×26.7 L). The combined organics were extracted with 2M HCl (1×15.0 L, 3×21.8 L). The aqueous phase was then charged back to the reactor and ethyl acetate was added (26.7 L). The pH was adjusted to 6.2 using 6 M sodium hydroxide (26.7 L) while maintaining a temperature between 15-25° C. The phases were separated and the aqueous phase was extracted with ethyl acetate (2×26.7 L). The combined organics were dried with magnesium sulfate and concentrated to give 4555 g of a residue (101% crude yield, 67.1% AUC by HPLC).

Purification of 4-(2-(4-(6-fluoropyridin-3-yl)phenoxy)ethyl)morpholine (5)

The crude product (575 g) was purified by silica gel chromatography by eluting with methanol/ethyl acetate/heptane (30% ethyl acetate/heptane, 50% ethyl acetate/heptane, 75% ethyl acetate/heptane, 100% ethyl acetate, and 5% methanol/ethyl acetate). Concentration of the pure fractions by TLC (10% methanol/dichloromethane, $R_f$=0.3) provided 420 g of a light brown solid (73% recovery, >99.9% AUC by HPLC).

Preparation of 2-(5-(4-(2-morpholinoethoxy)phenyl) pyridin-2-yl)acetonitrile (6)

A 1 M solution of NaHMDS (2.0 L, 5.0 equiv.) in THF was charged to a 5-L flask and cooled to −20 to −15° C. While maintaining a temperature below −10° C., fluoride (119.7 g, 1.0 equiv.) in THF (500 mL) was charged to the flask over 20 minutes. Acetonitrile (82.5 mL, 4.0 equiv.) in THF (170 mL) was added to the flask over 20 minutes, while maintaining a temperature below −10° C. The reaction mixture was then stirred for 1 h. To the reaction was added brine (1.5 L, 12.6 vol.) at a rate as to maintain a temperature below 10° C. The solution was then warmed to room temperature and the layers were allowed to separate. The mixture was filtered over Celite and washed with THF (1×200 mL, 1×100 mL). The aqueous phase was extracted with toluene (750 mL). The combined organics were dried with magnesium sulfate, filtered, washed with toluene (2×250 mL), and concentrated to dryness. Toluene (1 L) was added and the solution was concentrated to dryness again to give 169.8 g of an oil. MTBE (1190 mL, 7 vol.) was added to the oil at 50° C. and stirred for 15 minutes. Heptane (850 mL, 5 vol.) was added over ten minutes at 50° C. The mixture was then cooled to room temperature over 1.5 h and stirred for 2 h. The slurry was filtered, washed with 1:4 MBTE/heptane (2×100 mL), and dried in an oven overnight at 45° C. to give 102.3 g of an off-white solid (80% yield, 98.8% AUC by HPLC).

Preparation of methyl 2-(5-(4-(2-morpholinoethoxy) phenyl)pyridin-2-yl)acetate (7)

Nitrile 6 (101 g) and methanol (1.01 L, 10 vol.) were charged to a 3-L flask equipped with stir bar and thermocouple. Concentrated $H_2SO_4$ (175 mL, 10.0 equiv.) was added drop wise to the solution over 15 minutes while maintaining a temperature below 60° C. Followed by 30% fuming sulfuric acid (124 mL) was added drop wise to the solution while maintaining a temperature below 60° C. The solution was then heated to reflux with a heating mantle and stirred overnight. When the reaction was deemed complete, it was cooled to 20° C. In a second flask (22 L), saturated sodium bicarbonate (10.7 L) and dichloromethane (1.1 L) were charged and cooled to 15° C. While maintaining a temperature below 20° C., the reaction mixture was added to the sodium bicarbonate/dichloromethane mixture. The quench was stirred for 15 minutes and the phases were separated. The aqueous phase was extracted with dichloromethane (1×550 mL, 1×300 mL). The combined organics were dried with magnesium sulfate and concentrated to dryness to give 105 g of an orange solid (94% crude yield, 97.7% AUC by HPLC).

Preparation of 2-(5-(4-(2-morpholinoethoxy)phenyl) pyridin-2-yl)-N-benzylacetamide (KX2-391)

Ester 7 (103 g), anisole (513 mL, 5 vol.), and benzylamine (94 mL, 3.0 equiv.) were charged to a 3 L flask equipped with thermocouple and overhead stirrer. The reaction mixture was then heated to 142° C. and stirred for two days. The reaction mixture was cooled to 45-50° C. and stirred for 2 hours. To the mixture was added n-heptane (1.5 L) dropwise over an hour. The solution was cooled to room temperature over three hours and then stirred overnight. The resulting slurry was filtered, washed with 4:1 Anisole/n-heptane (200 mL) and n-heptane (3×100 mL). Drying in the oven overnight, the resulting product was 112.1 g of a tan solid (90% yield, 99.6% AUC by HPLC). The use of a single isomer of heptane was essential to adequately quantitate the residual solvent. See FIG. 5 for $^1$H NMR of KX2-391.

Preparation of 2-(5-(4-(2-morpholinoethoxy)phenyl) pyridin-2-yl)-N-benzylacetamide dihydrochloride salt (KX2-391•2HCl)

EtOH (1.0 L) was charged to a 2-L flask and acetyl chloride (62.5 mL, 3.0 equiv.) was added slowly to the flask and stirred for 40 minutes. The resulting solution was added to KX2-391 (100 g) over 30 minutes while maintaining a temperature of 30° C. The solution was concentrated to a mass of 270 g. The concentrated solution was added to ethyl acetate (2 L) over 20 minutes with rapid stirring. The mixture was stirred overnight and then filtered under nitrogen to give two distinct solid products, tan solids (73.5 g) and darker solids (42.2 g). The solids were dry blended to give a combined yield of 99%. The HPLC analysis indicated 99.0% purity (AUC). Analysis indicated that ethanol was present at 2530 ppm, ethyl acetate at 48,110 ppm, ethyl chloride at 170 ppm, and no heptane and anisole were detected. Palladium content was assayed three times and measured to be 29 ppm, 2 ppm, and less than 1 ppm.

Crystallization Study of KX2-391•2HCl

The experiments shown in Table 1 were conducted to explore different crystallization and precipitation conditions of KX2-391•2HCl.

TABLE 1

Crystallization Study of KX2-391 2HCl

| | | Salt Formation Conditions | | | Crystallization Conditions | | | | |
|---|---|---|---|---|---|---|---|---|---|
| Expt | Amide (g) | Lot | Solvent | Acid | Solvent (vol) | Lot | EtOAc (vol) | Temp (C.) | Nice Solids (y/n) | Comments |
| 02BP097A | 0.1 | 02BP090D (off-white) | IPA | IPA-HCl (5M) | IPA (10) | — | 10 | 60 | N | Gummy solids/ slurry formed as EtOAc added |
| 02BP097B | 0.1 | 02BP091E (white) | IPA | IPA-HCl (5M) | IPA (10) | — | — | 60 | N | Gummed out w/ cooling |
| 02BP097C | 0.1 | 02BP091E (white) | IPA | IPA-HCl (5M) | IPA (15) | — | 6 | 65 | N | Dried w/EtOAc first; product oiled out w/cooling |
| 02BP097D | 0.1 | 02BP091E (white) | — | IPA-HCl (5M) | EtOAc/ IPA | — | — | 60 | N | IPA-HCl added to amide solution; gummed out during addition (2 drops) |
| 02BP097E | 0.3 | 02BP090D (off-white) | EtOH | IPA-HCl (5M) | EtOH (3.3) | Acros | 6.3 | 30-60 | Y | Solids observed at 30° C. after EtOAc added; slow filtering |
| 02BP097F | 0.3 | 02BP093G (tan solid) | EtOH | IPA-HCl (5M) | EtOH (3.3) | Acros | 6.6 | 60 | Y | Solids observed during cooling after EtOAc added; slow filtering |
| 02BP097G | 0.3 | 02BP093G (tan solid) | PrOH | IPA-HCl (5M) | PrOH (3.3) | — | 1.7 | 60 | Y | Solids observed during cooling after EtOAc added; slow filtering |
| 02BP097H | 0.3 | 02BP093G (tan solid) | BuOH | IPA-HCl (5M) | BuOH (5) | — | 1.2 | 60 | Y | Solids observed during cooling after EtOAc added; very slow filtering |
| 02BP098A,B,C | 1.0 | 02BP093G (tan solid) | EtOH | IPA-HCl (5M) | EtOH (3.3) | Ald | 4-6 | 60 | N | Cloudiness observed earlier than expected; oiled out |
| 02BP098D | 1.0 | 02BP093G (tan solid) | EtOH | EtOH-HCl (2.5M) | EtOH (3.3) | Ald | 4.6 | 60 | N | Oiled out upon cooling |
| 02BP098E | 0.3 | 02BP090D (off-white) | EtOH | EtOH-HCl (2.5M) | EtOH (3.3) | Ald | 5.3 | 60 | N | Oiled out from EtOAc addition |
| 02BP098F | 0.3 | 02BP091E (white) | EtOH | IPA-HCl (5M) | EtOH (3.3) | Acros | 6 | 60 | N | Oiled out upon addition of EtOAc |
| 02BP098G | 0.3 | 02BP091E (white) | PrOH | IPA-HCl (5M) | PrOH (3.3) | — | 4 | 60 | N | Oiled out w/ cooling |

Figure 2:
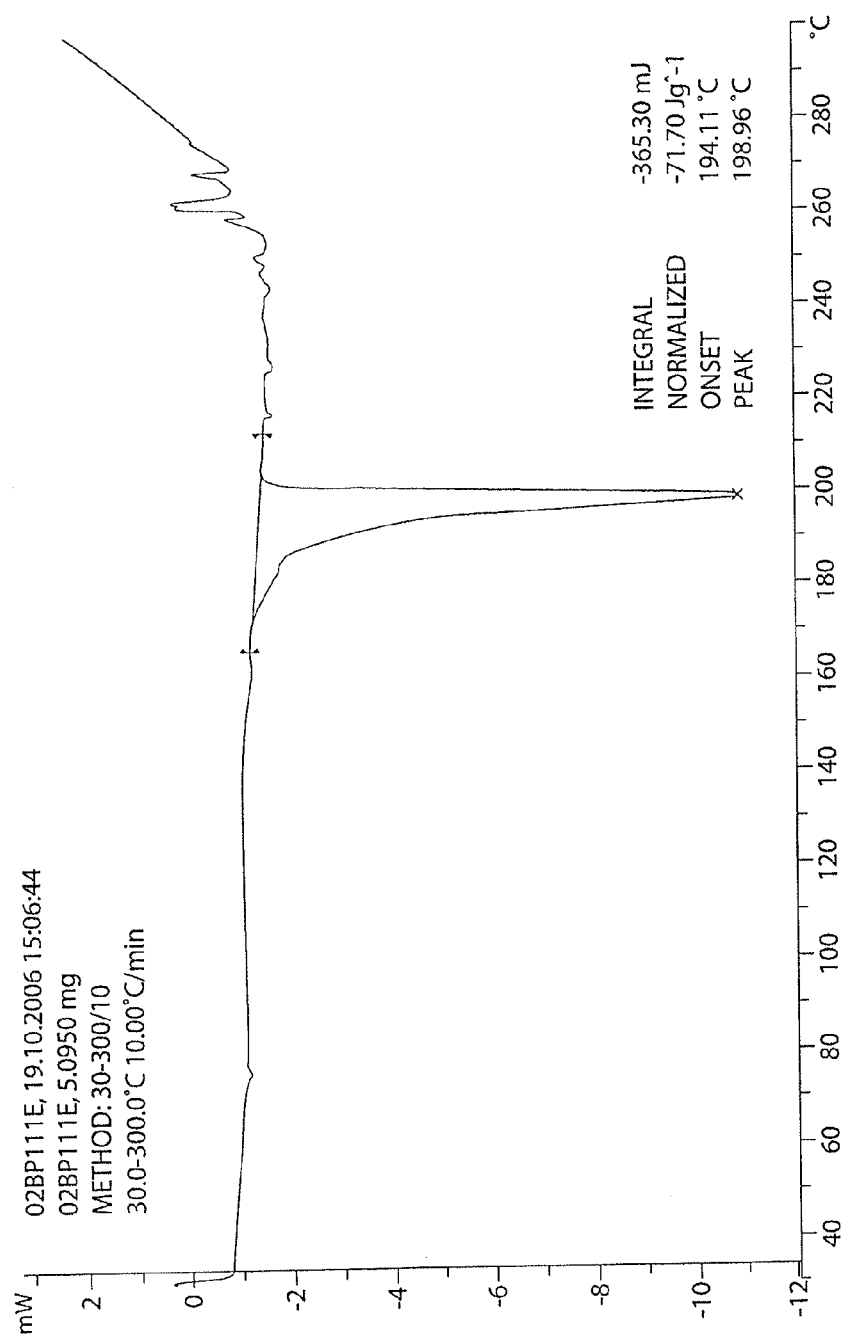
FIG. 2 is a graph indicating the DSC of KX2-391•2HCl lot 02BP111E.
Figure 3:
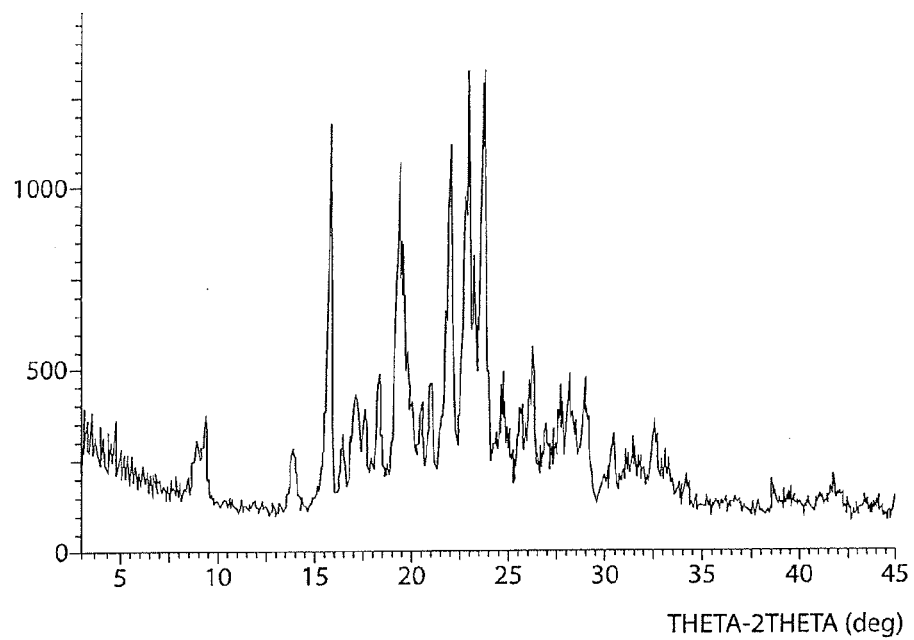
FIG. 3 is a graph indicating the XRPD of KX2-391•2HCl lot 02BP111E.
Figure 4:
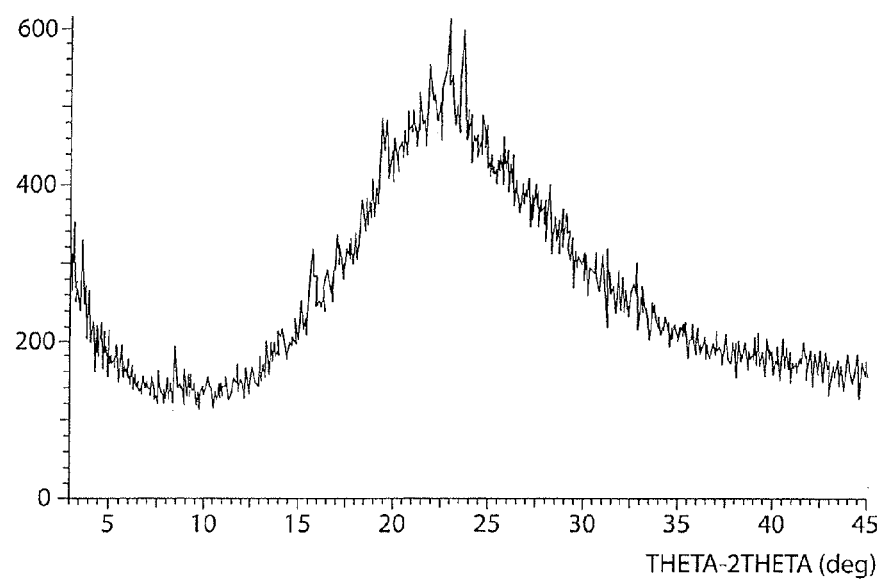
FIG. 4 is a graph indicating the XRPD of KX2-391•2HCl lot 02BP111F.

Precipitation was achieved by an inverse addition of KX2-391•2HCl in a concentrated solution of ethanol to a large volume of rapidly stirring ethyl acetate. This precipitation procedure was implemented for the demonstration batch resulting in the formation of two distinct solid types. The two distinct solid types were physically separated and filtered separately. A less dense tan solid (lot 02BP111E, 74 g, 99.1% AUC by HPLC) was filtered first followed by a denser darker solid (lot 02BP111F, 43 g, 99.1% AUC by HPLC). After drying in a vacuum oven and before blending the two solids a sample of each was retained for analysis. The data of interest is the Differential Scanning Calorimetry (DSC, FIGS. 1 and 2) and X-ray Powder Diffraction (XRPD, FIGS. 3 and 4). The HPLC data for the two samples were comparable while the DSC and XRPD were different.

Both of the HPLC preparations were greater than 99.0% pure (by area %), the lot 02BP111E sample showed a single endothermic event at approximately 198° C. while the lot 02BP111F sample showed two endothermic events at 117° C. and 189° C. The XRPD data for the two samples were also different the lot 02BP111E sample seemed crystalline while the lot 02BP111F sample appeared to be amorphous. The HPLC data, the XRPD data and the DSC data support that the two samples are different forms of the same material.

The two lots of KX2-391•2HCl (lot 02BP111E and 02BP111F) were dry blended resulting in a new lot of KX2-391⁻2HCl (lot 02BP111G). KX2-391•2HCl (lot 02BP111G) contained 170 ppm of ethyl chloride.

Example 4

Preparation of 2-(5-(4-(2-morpholinoethoxy)phenyl) pyridin-2-yl)-N-benzylacetamide mesylate (KX2-391•MSA)

Preparation of 2-(5-(4-(2-morpholinoethoxy)phenyl) pyridin-2-yl)acetonitrile (6)

To round bottom reactor 1 was charged sodium bis(trimethyldisilyl)amide (1.0 M in THF, 23.2 L) and the solution cooled to ≤−10° C. over 52 minutes. To a glass carboy, under nitrogen, was charged compound 5 (1400 g, 1 wt) and THF (7.0 L, anhydrous, 5 vol)). The batch was stirred with an air powered stirrer under nitrogen. The batch was not completely soluble and was a hazy solution. The solution of compound 5 was added to reactor 1 over 41 minutes via a 5-L addition funnel. A solution of acetonitrile (965 mL, anhydrous, 0.69 vol) in THF (2.0 L, anhydrous, 1.43 vol) was prepared and added to reactor 1 over 48 minutes at ≤−10° C. via the same addition funnel (a minor amount of a yellow solid was present on the reactor wall). After aging for 45 minutes at ≤−10° C. the batch was sampled for analysis and compound 5 was 0.03% by conversion (specification ≤1.5% by conversion). One hour 24 minutes after sampling, brine (17.6 L, 12.6 vol) was added to reactor 1 over 52 minutes and gave a poorly stirring batch (resembled an emulsion). A pad of diatomaceous earth was prepared on a 24-inch polypropylene funnel (1026 g Celite 545 slurried in 3.3 L water with the filtrate discarded). The batch was filtered under suction via the pad and the reactor rinsed with THF (1.75 L, 1.25 vol) and the rinse transferred to the cake. The cake was rinsed with a second portion of THF (1.75 L, 1.25 vol) and the total filtration time was 1 hour 17 minutes. The filtrate was transferred to reactor 2 and the phases separated and held overnight (the batch was held in the reactor under nitrogen). The organic phase (approximately 34.5 L) was drained and the aqueous phase extracted with toluene (8.1 L, 5.8 vol), stirring for 16 minutes and settling over 12 minutes. It is possible to omit the toluene extraction and simply add toluene directly to the organic phase after separation. The aqueous phase (approximately 19 L) was removed and the organic phases combined and dried in reactor 2 with magnesium sulfate (1400 g, 1 wt, anhydrous) over 55 minutes. The batch was filtered via a 24-inch polypropylene funnel equipped with an inline filter into a glass carboy. The batch was blanketed with argon and stored in the cold room (2-8° C.) pending concentration. The following day, the batch was concentrated to a residue and rinsed with toluene (11.8 L, 8.4 vol), which in turn was concentrated (water bath 50±5° C.). At the point of the toluene addition, the batch was an orange slurry and remained so after concentration. The total concentration time was 5 hours 3 minutes.

To reactor 3 was charged MTBE (13.9 L, 9.9 vol, ACS) which was then heated to 45±5° C. The MTBE was drained and approximately 2 L of MTBE was used to slurry the batch from the bulb into reactor 3. The remaining MTBE was added to reactor 3 maintaining the batch at 45±5° C. and the batch then aged for 33 minutes in this temperature range. n-Heptane (10 L, 7.1 vol, 99%) was then added to reactor 3 over 39 minutes maintaining the batch at 45±5° C. The heat source was disconnected the batch was cooled to 25±5° C. over 4 hours 5 minutes and aged at that temperature range for 27 hours 4 minutes. The batch was then filtered under suction via a 24-inch polypropylene funnel (PTFE cloth), covered and sucked dry under nitrogen. The total filtration time was 20 minutes. The orange batch (net wet weight 1322 g) was dried to constant weight over 48 hours 3 minutes in a vacuum oven set at 45±5° C. The batch was transferred to two 80 oz amber glass jars (Teflon lined closure) and blanketed with argon (1217 g of 6, 81% of theory).

Preparation of methyl 2-(5-(4-(2-morpholinoethoxy) phenyl)pyridin-2-yl)acetate (7)

To a 22-L reactor was charged compound 6 (900 g, 2.78 mol) and methanol (9.0 L, 10 vol, anhydrous). Sulfuric acid (1115 mL, fuming) was added to the suspension over 2 hours 11 minutes to give a dark solution. The maximum temperature was 65.5° C. (target <65° C.). Sulfuric acid (1565 mL, 1.74 vol, concentrated) was added to the batch over 1 hour 49 minutes and the batch then heated to visible reflux (74° C.) over 18 minutes. The batch was maintained at that temperature for 16 hours 57 minutes. The visible gentle reflux was noted to be absent, so the batch was then heated again to reflux at 79-80° C. over 2 hours 15 minutes. The batch was maintained at that temperature (80±5° C.) for 10 hours 57 minutes and the heat source then disconnected; an additional charge of methanol (0.75 L, 0.8 vol, anhydrous) was performed after 26 hours 4 minutes to replenish the lost solvent volume. It was estimated that 2.5-3.3 L of solvent was lost by evaporation. HPLC analysis after 42 hours 31 minutes from reflux indicated that the level of compound 6 was 0.6% by conversion (specification ≤1.0%). To each of reactor 1 and 2 was charged methylene chloride (4.8 L, 5.3 vol) and sodium hydrogen carbonate solution (48 L, 53.3 vol, saturated). The sodium hydrogen carbonate solutions were stored overnight at 2-8° C. and removed the next morning. Half the batch from the 22-L reactor was added in portions to each reactor over 47 and 44 minutes respectively (batch temperature was 12-13 and 14-15° C., respectively). The quench was accompanied by evolution of carbon dioxide (vigorous at the vortex). The batches from each reactor were then transferred to a 200-L reactor and the batch stirred for 16 minutes, then settled over 25 minutes and the organic phase separated. The aqueous phase was extracted successively with two portions of methylene chloride (5 L, 5.6 vol and 2.7 L, 3 vol); each extraction took place over 15 minutes stirring with settling over 6 and 9 minutes respectively. The combined organic phase was transferred to reactor 3 and dried with magnesium sulfate (900 g, 1 wt, anhydrous) over 35 minutes. The batch was then filtered under suction via a 24-inch polypropylene funnel fitted with Sharkskin cloth and equipped with an inline filter (10 micron, Pall P/N 12077). The filtrate was concentrated on a rotary evaporator over a total of 2 hours 18 minutes at 40±5° C. (water bath temperature). After 54 minutes the batch solidified and formed balls. These were broken up and concentration continued. The batch (a mixture of fine solids and brittle chunks) was then further ground and returned to the bulb and concentration continued. The batch was transferred to an 80-oz amber jar with a Teflon lined lid and blanketed with argon to give compound 7 (871 g, 88% of theory).

Preparation of 2-(5-(4-(2-morpholinoethoxy)phenyl) pyridin-2-yl)-N-benzylacetamide (KX2-391)

To a 22-L reactor was charged compound 7 (650 g, 1.82 mol), anisole (3.25 L, 5 vol, anhydrous) and benzylamine (600 mL, 0.92 vol, 3 equiv). The batch (approximately 18° C.) was heated to 142±5° C. over 1 hour 44 minutes, with dissolution occurring at 30° C. The batch was maintained at 142±5° C. for 69 hours 30 minutes at which point HPLC analysis indicated that compound 7 was 0.9% by conversion (specification ≤1.7% by conversion). The batch was cooled to 45-50° C. over 5 hours 12 minutes (to aid cooling the nitrogen flow was increased once the batch was approximately 72° C.). At that temperature range, the batch was poorly stirring and on mixing, the batch temperature increased to 52° C. It was >50° C. for ≤15 minutes. The batch was aged for 2 hours 2 minutes once initially <50° C., then n-heptane (9.75 L, 15 vol, 99%) was added to the batch over 1 hour 56 minutes, maintaining the batch temperature at 45-50° C. The heating was then discontinued and the batch cooled to 25° C. over 10 hours 32 minutes and then to approximately 20° C. over 20 minutes. The total time the batch was maintained ≤25° C. was 4 hours 50 minutes (2 hours 47 minutes at approximately 20° C.). The batch was filtered under suction via a 24-inch polypropylene filter funnel (fitted with a PTFE cloth) and the reactor rinsed with anisole/n-heptane (1.3 L, 4:1) and the rinse transferred to the cake. The cake was then washed successively with two portions of n-heptane (1.3 L, 0.65 L). The total filtration time was 39 minutes. The batch (net wet weight 1004 g of KX2•391) was transferred to three glass trays and placed into a vacuum oven set at 50° C. and dried to constant weight over 96 hours 26 minutes.

Preparation of 2-(5-(4-(2-morpholinoethoxy)phenyl) pyridin-2-yl)-N-benzylacetamide mesylate (KX2-391•MSA)

KX2-391 (520 g, 1.21 mol) was transferred to reactor 1 using acetone (41.6 vol, 80 vol, ACS) to facilitate the transfer. The batch was heated to 50±5° C. over 33 minutes with dissolution occurring at 30° C. The batch was clarified into a second reactor via a transfer pump fitted with an inline filter (Pall P/N 12077, 10 micron) and reheated from 46° C. to 50±5° C. Methanesulfonic acid (121.4 g, 1.05 equiv, 99% extra pure) was added to the pale yellow batch over 12 minutes and the heating then discontinued. After fourteen minutes, white solids were observed, which increased in number to give after 59 minutes a white suspension. The batch was in the range of 25±5° C. after 7 hours 51 minutes and aged for a further 19 hours 21 minutes (10 hours 30 minutes at ≤27° C.). The batch was filtered under suction via a 24-inch polypropylene filter (PTFE cloth) and the reactor rinsed with acetone (2.0 L, clarified, ACS) and the rinse transferred to the cake. The cake was covered with a stainless steel cover and sucked dry under a flow of nitrogen. The total filtration time was 21 minutes. The batch (net wet weight 764 g) was transferred to three glass drying trays and dried in a vacuum oven to constant weight at 25±5° C. over 21 hours 54 minutes (565 g, 89% of theory). A sample was removed for analysis and the batch maintained in vacuo at 25±5° C. The batch was then transferred to two 80-oz amber glass bottles (Teflon lined polypropylene closure), blanketed with argon and stored at −10 to −20° C.

Example 5

X-ray Powder Diffraction Analysis of KX2-391•MSA, Form A

X-ray powder diffraction (XRPD) analysis was performed using a Shimadzu XRD-6000 diffractometer on KX2-391•MSA, Form A obtained accordance with the process of the present invention (Example 4). The diffractometer was equipped with a Cu Kα X-ray tube operated at 40 kV, 40 mA. Samples were placed on a Si zero-return ultra-micro sample holders. The divergence slit was set at 1.00 degrees, scatter Slit was at 1.00 degrees and receiving slit was at 0.30 mm. The scan range was 3.0-45.0 degrees in continuous scan mode with a step size of 0.04 degrees and a scan Rate 2°/min. FIG. 7 depicts the X-ray diffractogram for KX2-391•MSA, Form A. The corresponding data for X-ray diffractograms is presented in Table 2.

TABLE 2

XRPD of KX2-391•MSA, Form A

Strongest 3 peaks

| no. | peak no. | 2Theta (deg) | d (A) | I/II | FWHM (deg) | Intensity (Counts) | Integrated Int (Counts) |
|---|---|---|---|---|---|---|---|
| 1 | 11 | 22.7377 | 3.90769 | 100 | 0.29390 | 2624 | 20079 |
| 2 | 3 | 16.3047 | 5.43208 | 62 | 0.29020 | 1623 | 13145 |
| 3 | 6 | 19.6782 | 4.50779 | 60 | 0.29280 | 1563 | 13084 |

Peak Data List

| peak no. | 2Theta (deg) | d (A) | I/II | FWHM (deg) | Intensity (Counts) | Integrated Int (Counts) |
|---|---|---|---|---|---|---|
| 1 | 13.0767 | 6.76484 | 10 | 0.29390 | 260 | 2343 |
| 2 | 15.6073 | 5.67320 | 7 | 0.29270 | 191 | 1749 |
| 3 | 16.3047 | 5.43208 | 62 | 0.29020 | 1623 | 13145 |
| 4 | 17.5438 | 5.05111 | 18 | 0.28760 | 467 | 4096 |
| 5 | 18.9449 | 4.68059 | 48 | 0.30900 | 1259 | 12580 |
| 6 | 19.6782 | 4.50779 | 60 | 0.29280 | 1563 | 13084 |
| 7 | 20.0800 | 4.41849 | 11 | 0.15360 | 298 | 2037 |
| 8 | 20.9600 | 4.23492 | 3 | 0.24000 | 87 | 682 |
| 9 | 21.4163 | 4.14571 | 8 | 0.30340 | 207 | 1843 |
| 10 | 22.2800 | 3.98692 | 14 | 0.35400 | 375 | 4393 |
| 11 | 22.7377 | 3.90769 | 100 | 0.29390 | 2624 | 20079 |
| 12 | 23.5116 | 3.78078 | 10 | 0.35120 | 260 | 2664 |
| 13 | 24.6429 | 3.60972 | 4 | 0.24270 | 108 | 641 |
| 14 | 25.2400 | 3.52566 | 4 | 0.28180 | 92 | 706 |
| 15 | 25.7200 | 3.46094 | 7 | 0.47700 | 190 | 1954 |
| 16 | 26.1200 | 3.40884 | 12 | 0.32600 | 321 | 2629 |
| 17 | 26.4400 | 3.36830 | 21 | 0.30440 | 557 | 4954 |
| 18 | 26.8000 | 3.32387 | 9 | 0.00000 | 229 | 0 |
| 19 | 27.1200 | 3.28537 | 7 | 0.37760 | 185 | 2917 |
| 20 | 29.6287 | 3.01266 | 3 | 0.28250 | 84 | 986 |

Example 6

Differential Scanning Calorimetric Analysis of KX2-391•MSA, Form A

Figure 8:
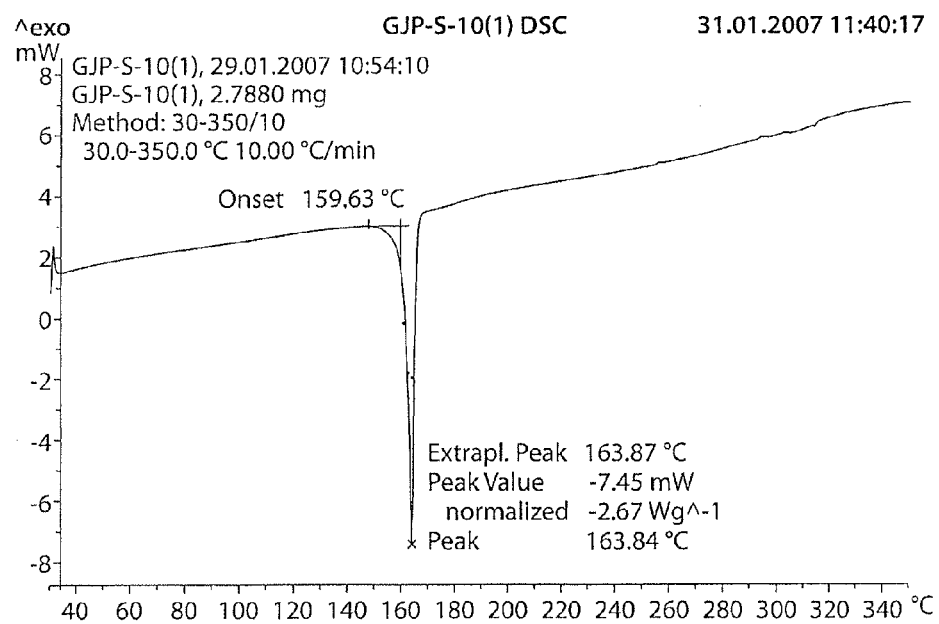
FIG. 8 is a graph indicating the DSC of KX2-391•MSA, Form A.

Differential Scanning Calorimetric (DSC) analysis was performed using a Mettler 822$^e$ DSC instrument on KX2-391•MSA, Form A obtained in accordance with the process of the present invention (Example 4). Samples were weighed in an aluminum pan, covered with a pierced lid, and then crimped. Analysis started at 30° C. to 300-350° C. ramped at 10° C./minute. A single endothermic event was recorded at 164° C. by DSC. FIG. 8 depicts the DSC thermogram for KX2-391•MSA, Form A.

Example 7

Thermal Gravimetric Analysis (TGA) of KX2-391•MSA, Form A

Figure 9:
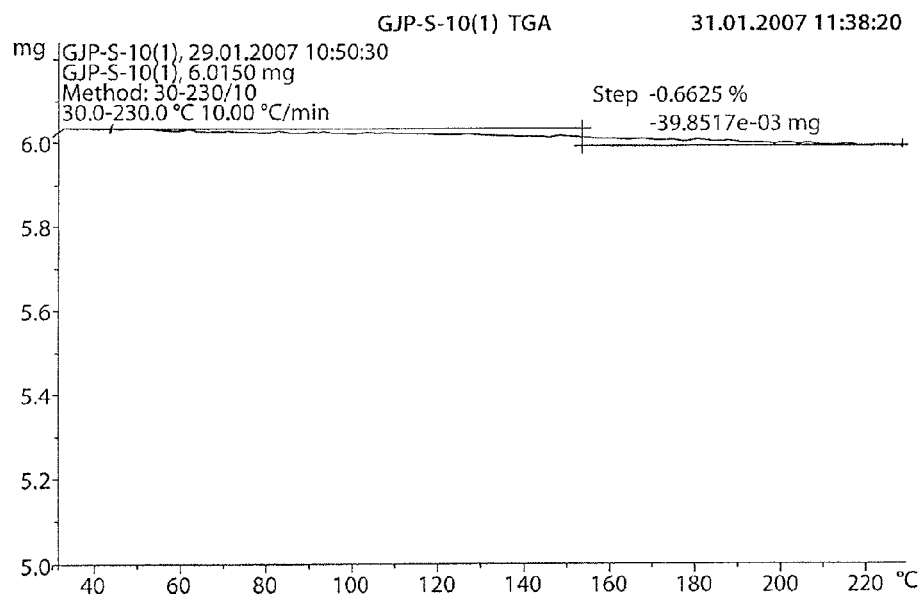
FIG. 9 is a graph indicating the TGA of KX2-391•MSA, Form A.

Thermal Gravimetric Analysis was performed using a Mettler 851$^e$ SDTA/TGA instrument on KX2-391•MSA, Form A obtained in accordance with the process of the present invention (Example 4). Samples were weighed in an alumina crucible and analyzed from 30° C. to 230° C. and a ramp rate of 10° C./minute. No weight loss was observed by TGA below 230° C. FIG. 9 depicts the TGA chromatogram for KX2-391•MSA, Form A.

Example 8

Moisture-Sorption Analysis and Humidity Chamber Studies of KX2-391•MSA

Figure 10:
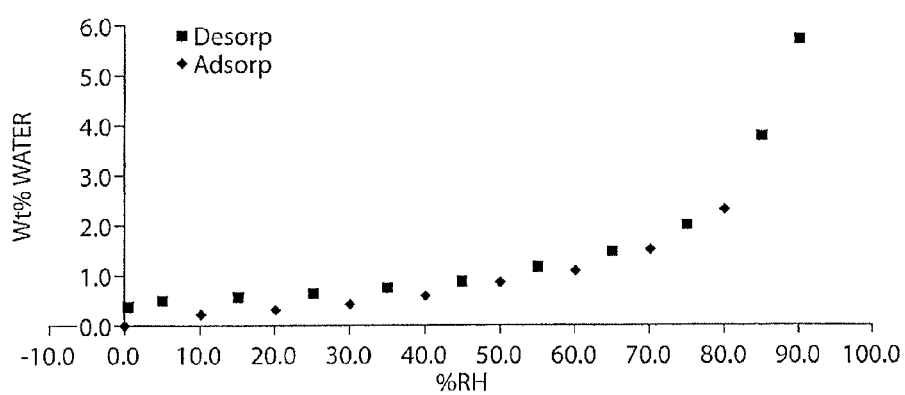
FIG. 10 is a graph indicating the Moisture Sorption Analysis of KX2-391•MSA, Form A.

Moisture-sorption experiments were performed using a Hiden IGAsorp Moisture Sorption instrument on KX2-391•MSA obtained in accordance with the process of the present invention (Example 4). First, the sample was dried at 0% Relative Humidity (RH) and 25° C. until an equilibrium weight was reached or for a maximum of four hours. The sample was then subjected to an isothermal (25° C.) adsorption scan from 10 to 90% RH in steps of 10%. The sample was allowed to equilibrate to an asymptotic weight at each point for a maximum of four hours. Following adsorption, a desorption scan from 85 to 0% RH (at 25° C.) was run in steps of −10% again allowing a maximum of four hours for equilibration to an asymptotic weight. The sample was then dried for one hour at 80° C. and the resulting solid analyzed by XRPD. In one aspect, moisture sorption analysis showed the sample KX2-391•MSA to be slightly-hygroscopic, absorbing 1.1 wt % water at 60% RH and 5.7 wt % water at 90% RH. The material resulting from the moisture sorption experiment was found to afford an XRPD pattern consistent with the starting form. FIG. 10 depicts percent change of water content as a function of relative humidity for KX2-391•MSA, Form A.

Further characterization of the hygroscopicity of the mesylate salt was performed using several humidity chambers to cover a range of humidity from 75, 88 to 95% RH. The 75, 88, and 95% RH chambers were prepared with NaCl, BaCl$_2$2H$_2$O, and Na$_2$HPO$_4$.12H$_2$O respectively and were equilibrated for 48 hours prior to introducing the samples. Samples were placed into aluminum pans and monitored by visual inspection for up to five days. Table 3 summarizes the observations at 0, 3, 5, 24, 48, 72, 96 and 120 hour time points. The mesylate salt was stable at 75% RH as the material did not deliquesce nor demonstrate decomposition by HPLC analysis. The material exposed to 88% RH conditions demonstrated a darker color yellow and degradation of roughly 10% area by HPLC. The 95% RH conditions were observed to deliquesce within three hours of exposure to high humidity.

TABLE 3

Summary of hygroscopicity study of KX2-391-MSA, Form A at 75, 88 and 95% Relative Humidity (RH)

| Sample Lot | Humidity Chamber ** (% RH/Salt) | Observations/Time (hr) | | | | | | | | XRPD* | HPLC Assay (% Area Purity) |
|---|---|---|---|---|---|---|---|---|---|---|---|
| | | 0 | 3 | 5 | 24 | 48 | 72 | 96 | 120 | | |
| GJP-S-17(1) | Initial | NA | NA | NA | NA | NA | NA | NA | NA | Consistent | 99.4 |
| | 75%-NaCl | FF | FF | FF | FF | FF | FF | FF | FF | Consistent | 99.4 |
| | 88%-BaCl$_2$•2H$_2$O | FF | CC | CC | CC | CC | CC | CC | CC | Consistent | 89.3 |
| | 95%-NA$_2$HPO$_4$•12H$_2$O | FF | D | D | D | D | D | D | D | NA | NA |

FF—Free flowing powder
D—Complete deliquescence of sample observed
CC—Colour change of sample observed
NA—Sample not analyzed
*Sample compared with XRPD pattern of sponsor lot
** Relative humidity based on literature values for salt solutions at 25-25° C.

Example 9

Stability Studies of KX2-391•MSA, Form A

Stability studies were performed on KX2-391•MSA obtained in accordance with the process of the present invention (Example 4) using the conditions listed in Table 4 to determine the effects of exposure to elevated temperature and/or relative humidity on the crystalline form of KX2-391•MSA, Form A. After 2 weeks, the samples were analyzed by XRPD and HPLC to determine if any form change or degradation had occurred. Results are shown in Table 5. Samples JSS-T-99 (6), (7), (8), (9), and (11) were observed to afford the same crystalline form by XRPD and HPLC did not show significant degradation. The material, JSS-T-99 (10), stored at 95% RH was observed to deliquesce under those conditions in less than 16 hours. The results showed KX2-391•MSA, Form A to be a stable crystalline form after exposure to the accelerated stability conditions utilized.

TABLE 4

60° C./ambient humidity, oven
51% RH, saturated salt chamber [Ca(NO3)2•4H2O]
75% RH, saturated salt chamber [NaCl]
88% RH, saturated salt chamber [BaCl2•2H2O]
95% RH, saturated salt chamber [Na2HPO4•12H2O]
40° C./75% RH, accelerated stability chamber

TABLE 5

Stability Studies

| NB Code | KX2-391-MSA Amt (mg) | Exposure Condition | Initial Form (XRPD) | Form After 2 Weeks (XRPD) | HPLC Purity (AUC) |
|---|---|---|---|---|---|
| JSS-T-99(6) | 17.9 | 60° C. | Form A | Form A | >99% |
| JSS-T-99(7) | 3.619 | 51% RH | | Form A | >99% |
| JSS-T-99(8) | 4.125 | 75% RH | | Form A | >99% |
| JSS-T-99(9) | 3.997 | 88% RH | | Form A | >99% |
| JSS-T-99(10) | 5.756 | 95% RH | | Deliquesced <16 hrs | NA |
| JSS-T-99(11) | 59.2 | 40° C./75% | | Form A | >99% |

Example 10

High Performance Liquid Chromatography of KX2-391•MSA, Form A

High Performance Liquid Chromatography (HPLC) was performed using a Waters Alliance HPLC system on KX2-391•MSA, Form A obtained in accordance with the process of the present invention (Example 4). The HPLC system was equipped with a UV detector, gradient capabilities, and electronic data collection and processing, or equivalent, auto sampler capable of 10 μL injection, analytical column Thermo Hypersil Gold, 4.6×150 mm, 3.0 μm, P/N 25003-154630, Analytical balance capable of weighing to ±0.01 mg, class A volumetric pipettes and flasks.

Figure 11:
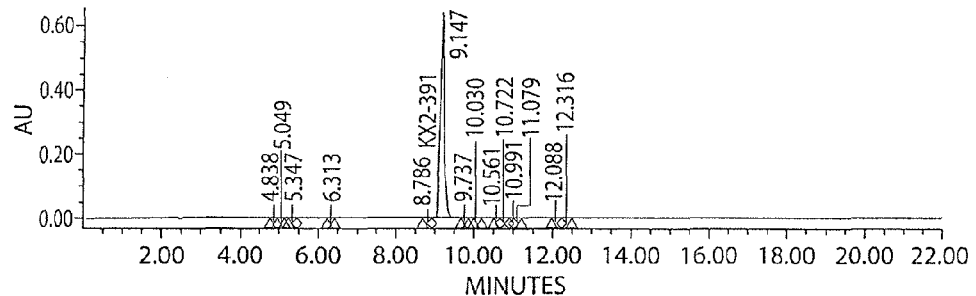
FIG. 11 is an HPLC chromatogram of KX2-391•MSA, Form A.

The column used for analyses was Thermo Hypersil Gold, 4.6×150 mm, 3.0 μm and the column and auto-sampler temperature was ambient. Detection of eluted compound occurred at 248 nm (KX2-391 was detected at 248 nm) and 210 nm (benzylamine was detected at 210 nm). Mobile phase A was 0.05% TFA in Water and Mobile Phase B was 0.05% TFA in acetonitrile with a flow rate of 1.0 mL/min. The elution gradient is depicted in Table 6. An injection volume of 10 μL was used for all samples with an analysis time of 30 min. Re-equilibration Time and Data Collection Time were 8 min and 22 min, respectively. Needle Wash upon run completion was completed in 50:50 acetonitrile/Water. FIG. 11 depicts the HPLC chromatogram and peak results for KX2-391•MSA, Form A.

TABLE 6

HPLC elution gradient for KX2-391•MSA, Form A

| Time (minutes) | % A | % B |
|---|---|---|
| 0.0 | 95 | 5 |
| 20.0 | 30 | 70 |
| 21.0 | 0 | 100 |
| 22.0 | 0 | 100 |
| 22.5 | 95 | 5 |
| 30.0 | 95 | 5 |

Example 11

Figure 12:
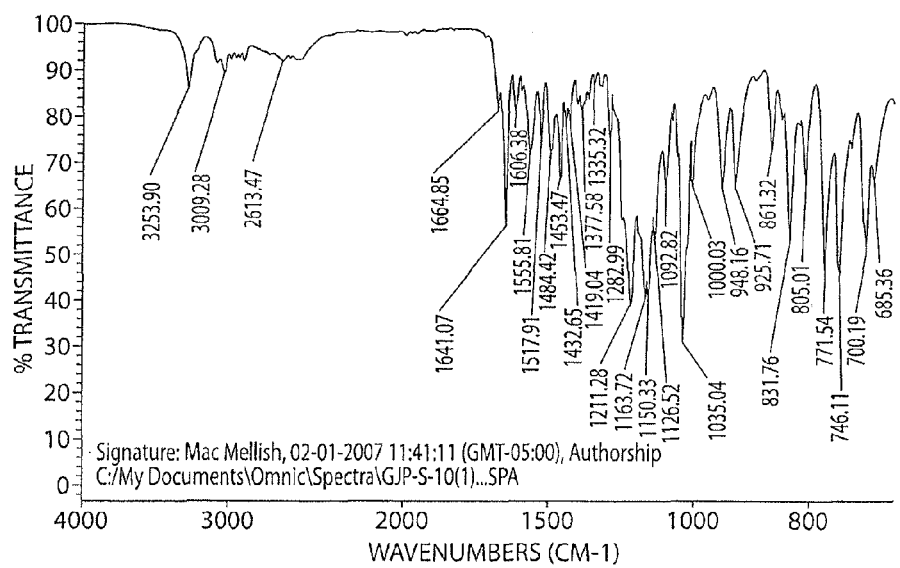
FIG. 12 is an ATR-FTIR spectrum of KX2-391•MSA, Form A.

Attenuated Total-Reflection Fourier Transform infrared Analysis of KX2-391•MSA, Form A Attenuated total-reflection Fourier-transform infrared analysis (ATR-FTIR) analyses were performed on KX2-391•MSA, Form A obtained in accordance with the process of the present invention (Example 4). After a background of ambient lab conditions was obtained, samples were placed on the ATR, compressed with the anvil and the spectrum was acquired. FIG. 12 depicts the ATR-FTIR spectrogram for KX2-391•MSA, Form A as measured by a Thermo-Nicolet Avatar 370 with Smart Endurance Attenuated Total-Reflection Attachment.

Example 12

XRPD of KX2-391•2HCl

Figure 13:
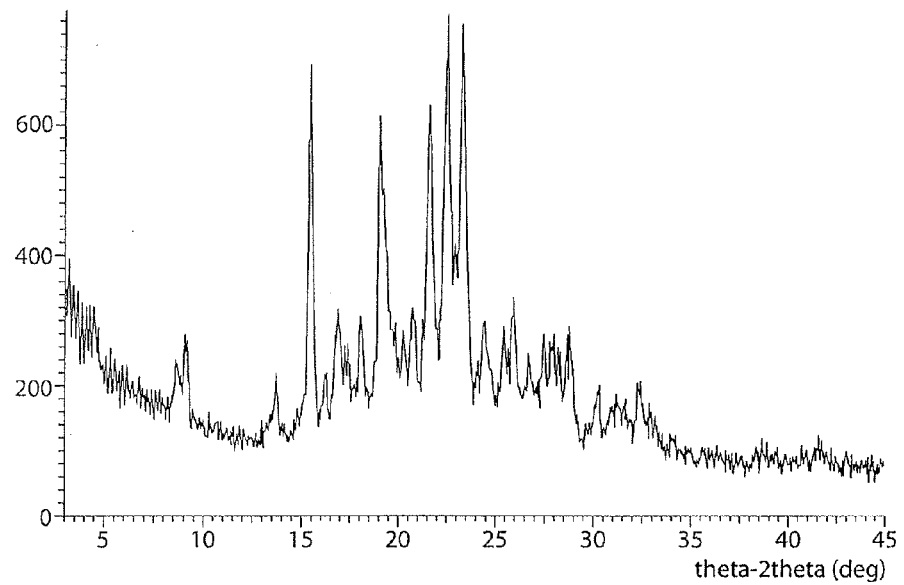
FIG. 13 is a graph indicating the XRPD of KX2-391•2HCl [lot 02BP111G].

X-ray powder diffraction (XRPD) analysis was performed using a Shimadzu XRD-6000 diffractometer on KX2-391•HCl obtained in accordance with the process of the present invention (Example 3). The diffractometer was equipped with a Cu Kα X-ray tube operated at 40 kV, 40 mA. Samples were placed on a Si zero-return ultra-micro sample holders. The divergence slit was set at 1.00 degrees, scatter Slit was at 1.00 degrees and receiving slit was at 0.30 mm. The scan range was 3.0-45.0 degrees in continuous scan mode with a step size of 0.04 degrees and a scan Rate 2°/min. FIG. 13 depicts the X-ray diffractogram for KX2-391•2HCl (lot 02BP 111G) The corresponding data for X-ray diffractograms is presented in Table 7.

TABLE 7

XRPD of KX2-391•2HCl

Strongest 3 peaks

| no. | peak no. | 2Theta (deg) | d (A) | I/II | FWHM (deg) | Intensity (Counts) | Integrated Int (Counts) |
|---|---|---|---|---|---|---|---|
| 1 | 19 | 22.7110 | 3.91222 | 100 | 0.45330 | 408 | 5232 |
| 2 | 20 | 23.5201 | 3.77944 | 96 | 0.38820 | 392 | 4280 |
| 3 | 8 | 15.5737 | 5.68537 | 82 | 0.32590 | 336 | 2893 |

Peak Data List

| peak no. | 2Theta (deg) | d (A) | I/II | FWHM (deg) | Intensity (Counts) | Integrated Int (Counts) |
|---|---|---|---|---|---|---|
| 1 | 3.1741 | 27.81298 | 6 | 0.15180 | 23 | 116 |
| 2 | 4.5300 | 19.49070 | 5 | 0.34000 | 22 | 294 |
| 3 | 8.7600 | 10.08629 | 14 | 0.38160 | 58 | 554 |
| 4 | 9.1153 | 9.69393 | 23 | 0.35070 | 93 | 802 |
| 5 | 13.3200 | 6.64181 | 3 | 0.32000 | 12 | 142 |
| 6 | 13.7571 | 6.43175 | 14 | 0.36220 | 56 | 552 |
| 7 | 14.9200 | 5.93296 | 3 | 0.28800 | 14 | 181 |

TABLE 7-continued

XRPD of KX2-391·2HCl

| | | | | | | |
|---|---|---|---|---|---|---|
| 8  | 15.5737 | 5.68537 | 82  | 0.32590 | 336 | 2893 |
| 9  | 16.3015 | 5.43314 | 12  | 0.27690 | 49  | 361  |
| 10 | 17.0241 | 5.20412 | 28  | 0.46820 | 114 | 1110 |
| 11 | 17.4400 | 5.08094 | 17  | 0.48000 | 68  | 728  |
| 12 | 18.1931 | 4.87228 | 22  | 0.34260 | 90  | 842  |
| 13 | 19.3172 | 4.59121 | 74  | 0.52120 | 301 | 3628 |
| 14 | 19.8800 | 4.46249 | 19  | 0.38400 | 77  | 929  |
| 15 | 20.3857 | 4.35291 | 16  | 0.34860 | 64  | 559  |
| 16 | 20.8704 | 4.25290 | 23  | 0.31920 | 94  | 743  |
| 17 | 21.4000 | 4.14883 | 12  | 0.22220 | 50  | 314  |
| 18 | 21.7790 | 4.07748 | 76  | 0.36530 | 309 | 3085 |
| 19 | 22.7110 | 3.91222 | 100 | 0.45330 | 408 | 5232 |
| 20 | 23.5201 | 3.77944 | 96  | 0.38820 | 392 | 4280 |
| 21 | 24.5793 | 3.61891 | 21  | 0.38530 | 86  | 1079 |
| 22 | 25.5200 | 3.48761 | 15  | 0.24620 | 63  | 525  |
| 23 | 26.0463 | 3.41832 | 27  | 0.35920 | 110 | 1113 |
| 24 | 26.8326 | 3.31991 | 14  | 0.40930 | 57  | 714  |
| 25 | 27.6000 | 3.22932 | 22  | 0.45860 | 89  | 1353 |
| 26 | 28.0000 | 3.18409 | 24  | 0.00000 | 97  | 0    |
| 27 | 28.3200 | 3.14883 | 18  | 0.00000 | 72  | 0    |
| 28 | 28.8464 | 3.09256 | 27  | 0.53290 | 111 | 1789 |
| 29 | 29.7600 | 2.99966 | 4   | 0.24000 | 15  | 142  |
| 30 | 30.2962 | 2.94778 | 14  | 0.34100 | 57  | 521  |
| 31 | 31.0000 | 2.88245 | 10  | 0.42000 | 41  | 570  |
| 32 | 31.3200 | 2.85372 | 11  | 0.00000 | 43  | 0    |
| 33 | 31.6000 | 2.82907 | 10  | 0.80000 | 40  | 709  |
| 34 | 32.4762 | 2.75472 | 17  | 0.46100 | 70  | 825  |
| 35 | 33.1600 | 2.69946 | 9   | 0.32000 | 35  | 415  |
| 36 | 34.1366 | 2.62443 | 3   | 0.32670 | 14  | 118  |
| 37 | 38.3914 | 2.34279 | 3   | 0.17710 | 13  | 64   |
| 38 | 38.7800 | 2.32021 | 3   | 0.28000 | 13  | 113  |
| 39 | 39.4166 | 2.28419 | 3   | 0.28670 | 13  | 169  |
| 40 | 40.9400 | 2.20264 | 3   | 0.20000 | 14  | 95   |
| 41 | 41.6020 | 2.16911 | 6   | 0.43600 | 24  | 303  |
| 42 | 43.0450 | 2.09967 | 3   | 0.15000 | 12  | 54   |

Example 13

DSC of KX2-391·2HCl

Figure 14:
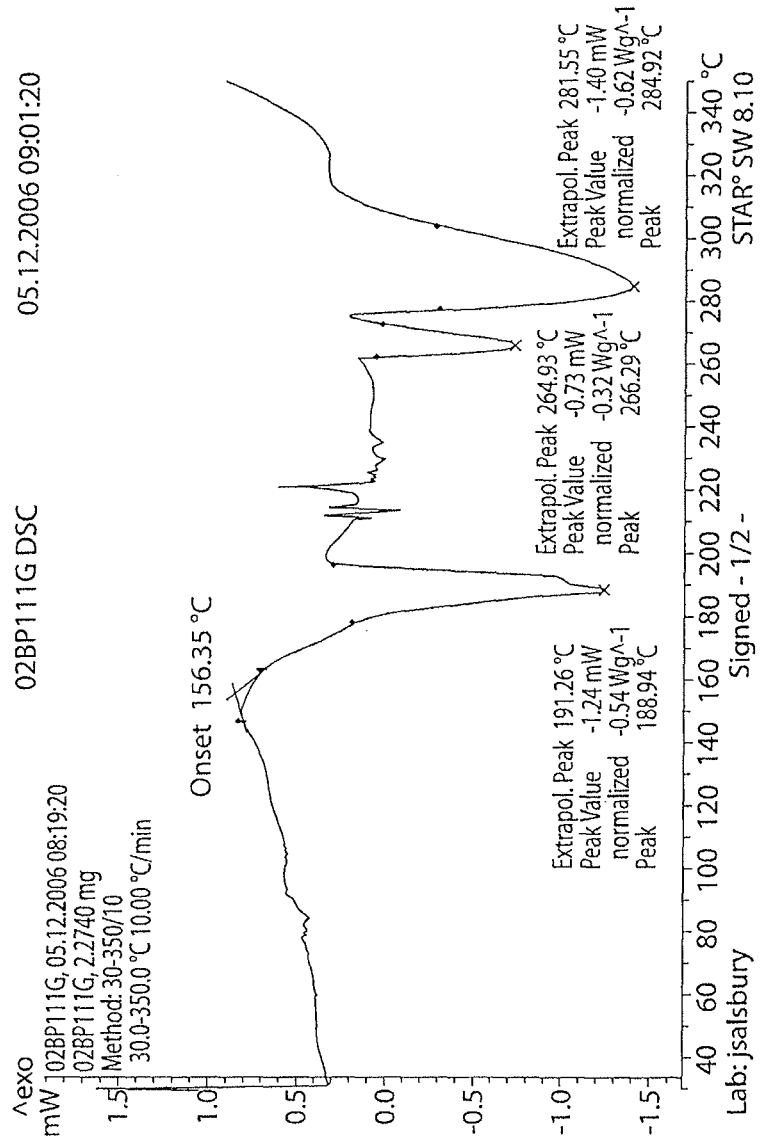
FIG. 14 is a graph indicating the DSC of KX2-391•2HCl [lot 02BP111G].

Differential Scanning Calorimetric (DSC) analysis was performed using a Mettler 822$^e$ DSC instrument on KX2-391·2HCl obtained in accordance with the process of the present invention (Example 3). Samples were weighed in an aluminum pan, covered with a pierced lid, and then crimped. Analysis started at 30° C. to 300-350° C. ramped at 10° C./minute. The DSC curve showed three endothermic events at 189, 266, and 285° C. FIG. 14 depicts the DSC thermogram for KX2-391·2HCl (lot 02BP111G).

Example 14

TGA of KX2-391·2HCl

Figure 15:
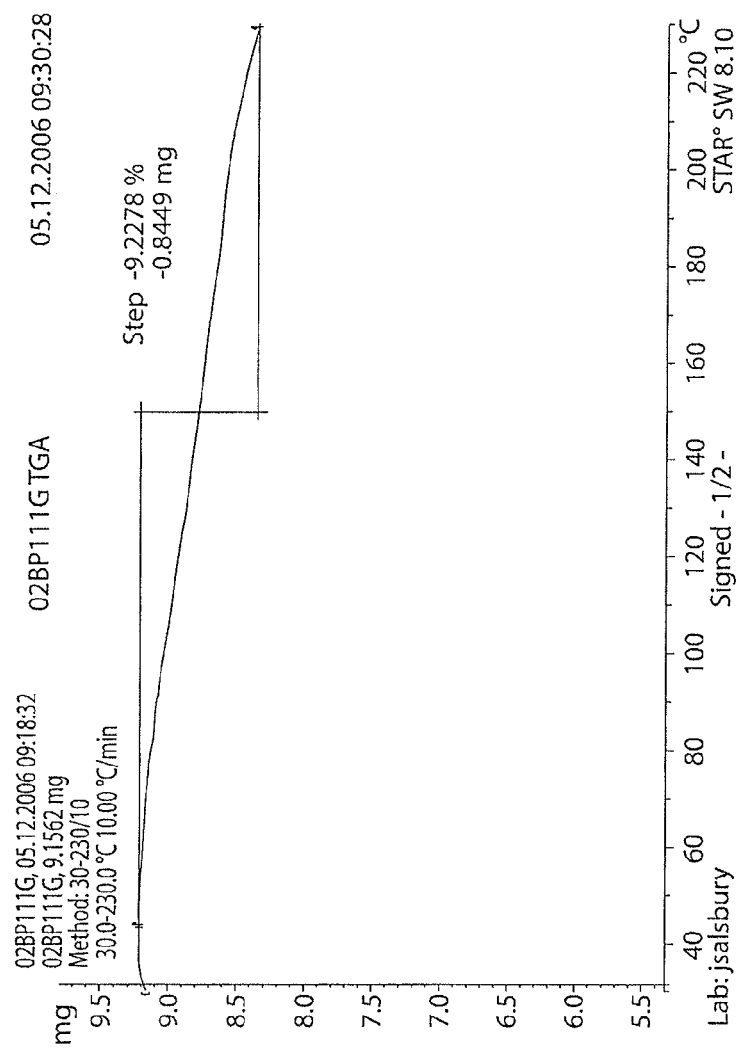
FIG. 15 is a graph indicating the TGA of KX2-391•2HCl [lot 021BP111G].

Thermal Gravimetric Analysis was performed using a Mettler 851$^e$ SDTA/TGA instrument on KX2-391·2HCl obtained in accordance with the process of the present invention (Example 3). Samples were weighed in an alumina crucible and analyzed from 30° C. to 230° C. and a ramp rate of 10° C./minute. A 9.2% weight loss was observed between 30-230° C. FIG. 15 depicts the TGA chromatogram for KX2-391·2HCl (lot 02BP111G).

Example 15

Moisture Sorption Analysis of KX2-391·2HCl

Figure 19:
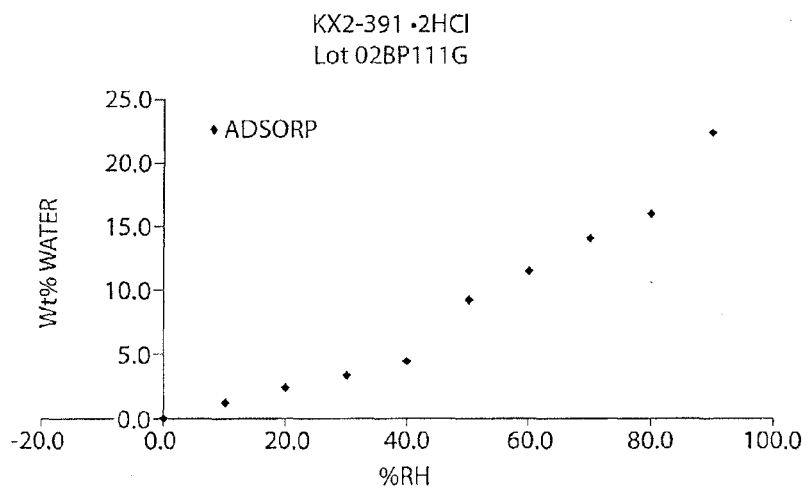
FIG. 19 is graph showing the gravimetric moisture curve of KX2•391•2HCl.

Moisture-sorption experiments were performed using a Hiden IGAsorp Moisture Sorption Instrument on KX2-391·2HCl obtained in accordance with the process of the present invention (Example 3). First, the sample was dried at 0% Relative Humidity (RH) and 25° C. until an equilibrium weight was reached or for a maximum of four hours. The sample was then subjected to an isothermal (25° C.) adsorption scan from 10 to 90% RH in steps of 10%. The sample was allowed to equilibrate to an asymptotic weight at each point for a maximum of four hours. Following adsorption, a desorption scan from 85 to 0% RH (at 25° C.) was run in steps of −10% again allowing a maximum of four hours for equilibration to an asymptotic weight. The sample was then dried for one hour at 80° C. and the resulting solid analyzed by XRPD. In one aspect, moisture sorption analysis showed the sample to be significantly hygroscopic, absorbing 16.7 wt % water at 60% RH and 27.0 wt % water at 90% RH suggesting deliquescence with an inflection point between 40-50% RH. FIG. 19 shows the gravimetric moisture curve of KX2-391·2HCl (lot 02BP111G).

Figure 17:
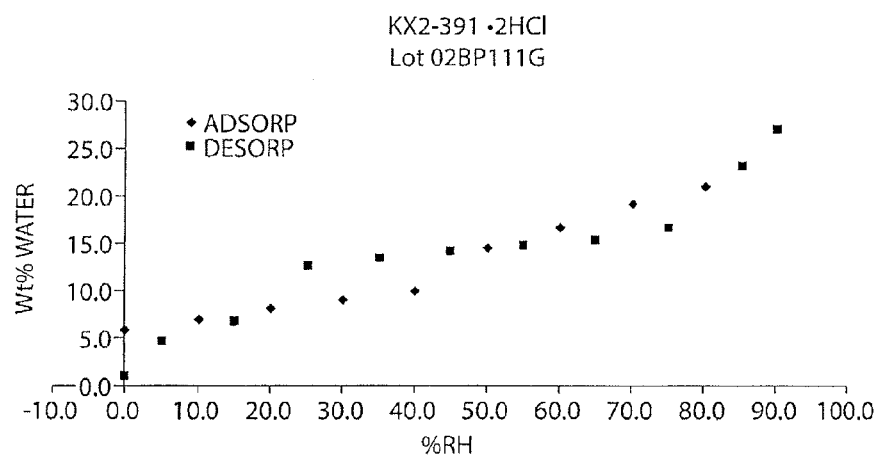
FIG. 17 is a graph indicating the Moisture Sorption Analysis of KX2-391•2HCl [lot 02BP111G].

Table 8 contains the data presented in FIG. 17. Moisture sorption studies conducted at ambient temperature utilizing salt solution humidity chambers were conducted to evaluate solid stability by visual inspection. The results are presented in Table 9. Samples were observed to completely deliquesce at 51 and 95% RH within 12 hours. When KX2-391·2HCl was subjected to 42% RH, deliquescence was observed within three hours and continued to remain in this state for the following seven days. However, when KX2-391·2HCl was subjected to 32% RH it was found to remain stable over the same seven day period indicating the deliquescence humidity at ambient temperature was between 32-42% RH.

TABLE 8

Moisture Sorption Analysis of KX2-391·2HCl

| % RH | TW/mg | Mg water | Wt %/ water | Mmol water | Mole ration (water:sample) |
|---|---|---|---|---|---|
| −0.0500 | 6.6919 | 0.3936 | 5.8814 | 0.0218 | 1.7493 |
| 10.0011 | 6.7707 | 0.4724 | 6.9776 | 0.0262 | 2.0998 |
| 20.0071 | 6.8565 | 0.5582 | 8.1412 | 0.0310 | 2.4810 |
| 29.9953 | 6.9250 | 0.6267 | 9.0498 | 0.0348 | 2.7855 |
| 39.9936 | 7.0029 | 0.7046 | 10.0615 | 0.0391 | 3.1317 |
| 50.0083 | 7.3749 | 1.0766 | 14.5986 | 0.0597 | 4.7853 |
| 59.9940 | 7.5634 | 1.2651 | 16.7261 | 0.0702 | 5.6228 |
| 70.0044 | 7.7942 | 1.4959 | 19.1922 | 0.0830 | 6.6487 |
| 80.0002 | 7.9711 | 1.6728 | 20.9856 | 0.0928 | 7.4350 |
| 90.0102 | 8.6234 | 2.3251 | 26.9630 | 0.1290 | 10.3345 |
| 90.0102 | 8.6234 | 2.3251 | 26.9630 | 0.1290 | 10.3345 |
| 84.9979 | 8.1862 | 1.8879 | 23.0617 | 0.1048 | 8.3910 |
| 75.0016 | 7.5530 | 1.2547 | 16.6119 | 0.0696 | 5.5767 |
| 64.9989 | 7.4448 | 1.1465 | 15.3997 | 0.0636 | 5.0957 |
| 54.9876 | 7.3912 | 1.0929 | 14.7870 | 0.0607 | 4.8578 |
| 45.0063 | 7.3402 | 1.0419 | 14.1945 | 0.0578 | 4.6309 |
| 35.0089 | 7.2811 | 0.9828 | 13.4981 | 0.0545 | 4.3683 |
| 25.0029 | 7.2130 | 0.9147 | 12.6812 | 0.0508 | 4.0655 |
| 15.0035 | 6.7598 | 0.4615 | 6.8271 | 0.0256 | 2.0512 |
| 4.9957 | 6.6101 | 0.3118 | 4.7176 | 0.0173 | 1.3860 |
| −0.0430 | 6.3667 | 0.0684 | 1.0737 | 0.0038 | 0.3038 |

TABLE 9

Hygroscopicity of KX2-391·2HCl

| % RH | Results | Time |
|---|---|---|
| 95 | Deliquescence | <12 h |
| 51 | Deliquescence | <12 h |
| 42 | Deliquescence | <3 h |
| 32 | Solid | 7 days |

Example 16

High Performance Liquid Chromatography of KX2-391·2HCl

High Performance Liquid Chromatography (HPLC) was performed on KX2-391·2HCl obtained in accordance with the process of the present invention (Example 3). The HPLC system was equipped with a UV detector, gradient capabilities, and electronic data collection and processing, or equivalent, auto sampler capable of 10 μL injection, analytical column Thermo Hypersil Gold, 4.6×150 mm, 3.0 μm, P/N 25003-154630, Analytical balance capable of weighing to ±0.01 mg, class A volumetric pipettes and flasks.

Figure 18:
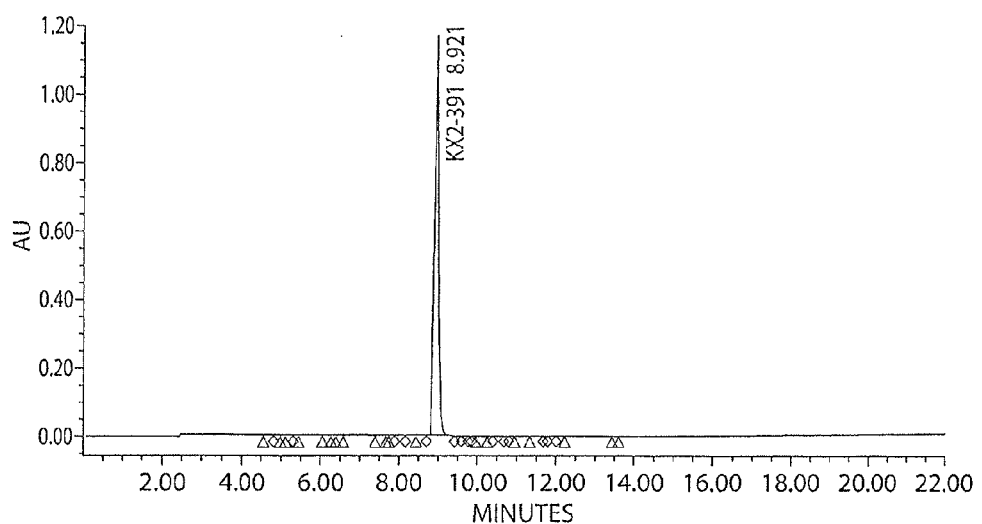
FIG. 18 is an HPLC chromatograms of KX2-391•2HCl [lot 02BP111G].

The column used for analyses was Thermo Hypersil Gold, 4.6×150 mm, 3.0 μm and the column and auto-sampler temperature was ambient. Detection of eluted compound occurred at 248 nm (KX2-391 was detected at 248 nm) and 210 nm (benzylamine was detected at 210 nm). Mobile phase A was 0.05% TFA in water whereas mobile phase B was 0.05% TFA in acetonitrile with a flow rate of 1.0 mL/min. The elution gradient is depicted in Table 10. An injection volume of 10 μL was used for all samples with an analysis time of 30 min. Re-equilibration time and data collection time were 8 min and 22 min, respectively. Needle wash upon run completion was completed in 50:50 acetonitrile/water. FIG. 18 depicts the HPLC chromatogram for KX2-391·2HCl (lot 02BP111G).

TABLE 10

HPLC elution gradient for KX2-391·2HCl

| Time (Minute) | % A | % B |
|---|---|---|
| 0.0 | 95 | 5 |
| 20.0 | 30 | 70 |
| 21.0 | 0 | 100 |
| 22.0 | 0 | 100 |
| 22.5 | 95 | 5 |
| 30.0 | 95 | 5 |

Example 17

Proton Nuclear Magnetic Resonance Spectroscopy of KX2-391·MSA, Form A

Figure 6:
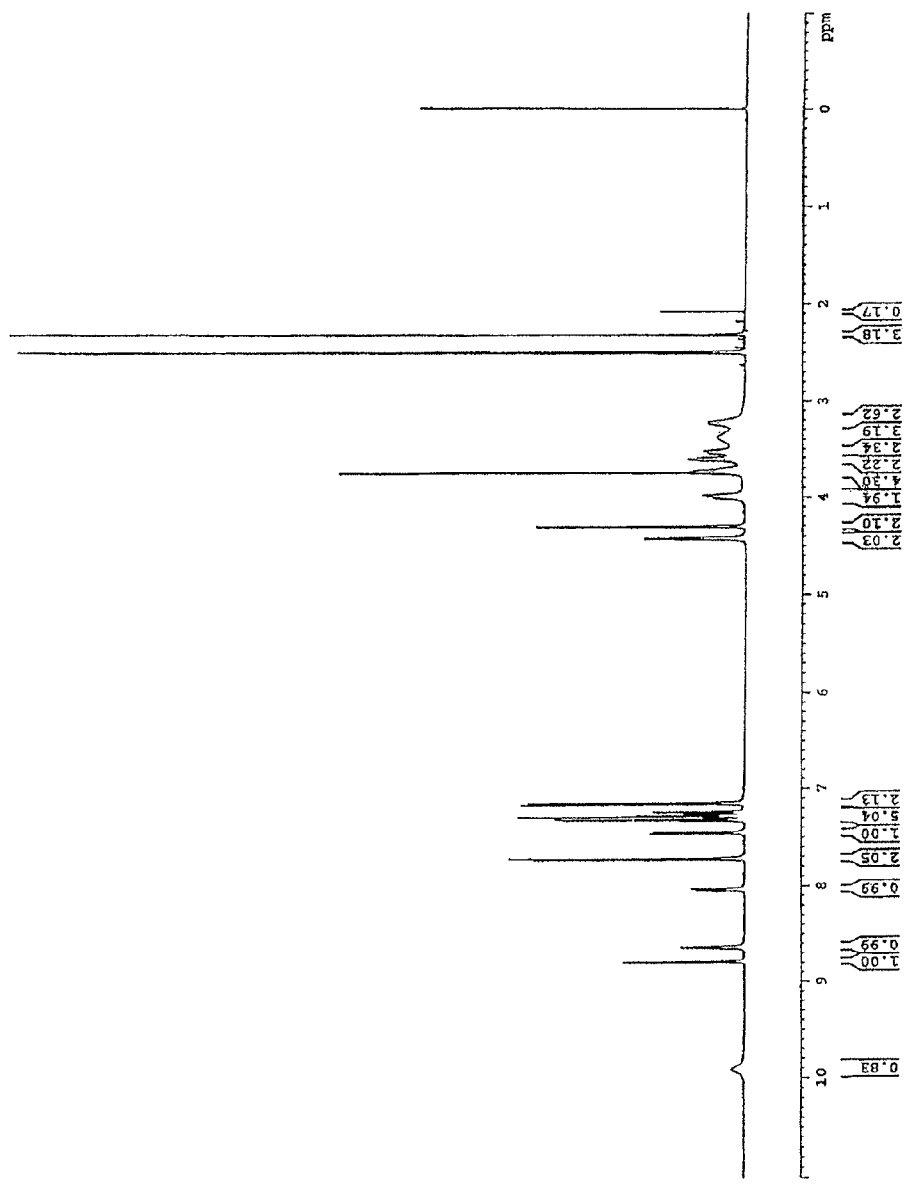
FIG. 6 is a 1H NMR spectrum of KX2-391•MSA, Form A.

Acquisition of $^1$H NMR spectra were performed with 2-10 mg of sample dissolved in 0.8 mL of DMSO-$d_6$. Spectra were acquired using 32 to 64 scans with a pulse delay of 1.0 sec and 10 μs (30°) pulse width. FIG. 6 depicts the $^1$H NMR spectrum for KX2-391·MSA, Form A.

Example 18

Proton Nuclear Magnetic Resonance Spectroscopy of KX2-391·2HCl

Figure 5:
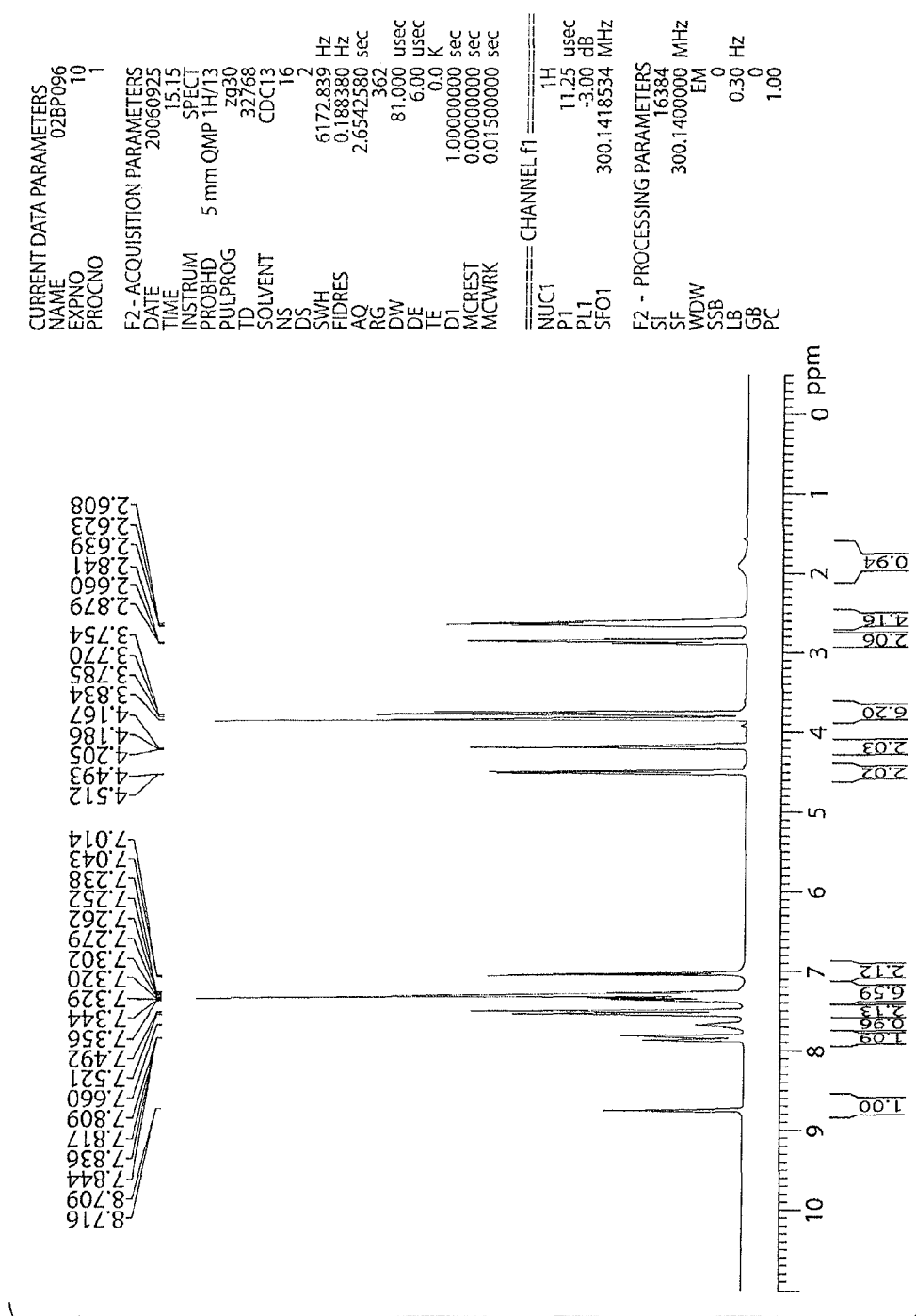
FIG. 5 is a 1H NMR spectrum of KX2-391 (lot 02BP096K).
Figure 16:
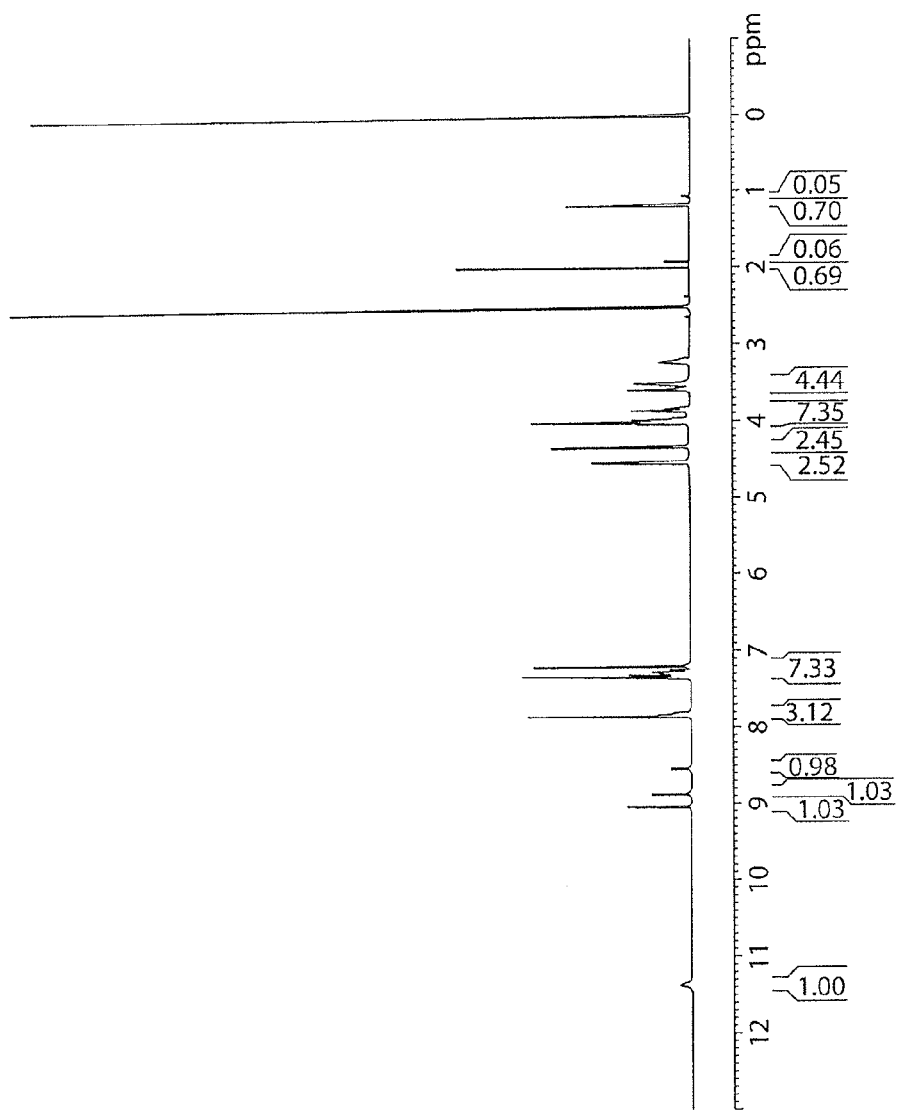
FIG. 16 is a 1H NMR spectrum of KX2-391•2HCl [lot 02BP111G].

Acquisition of $^1$H NMR spectra were performed with 2-10 mg of sample dissolved in 0.8 mL of DMSO-$d_6$. Spectra were acquired using 32 to 64 scans with a pulse delay of 1.0 sec and 10 μs (30°) pulse width. FIG. 5 depicts the $^1$H NMR spectrum for KX2-391 free base. FIG. 16 depicts the 1H NMR spectrum for KX2-391·2HCl (lot 02BP111G).

Example 19

Process Optimization for KX2-391·MSA, Form A

Process optimization of the mesylate salt was initiated due the decision that the mesylate salt was the most desired. In the salt screen acetone with 200 volumes of solvent was used to form the mesaylate salt. To make a scalable process, the amount of acetone had to be reduced to a workable volume. The table below summarizes the data generated.

| NB Code | Material Amt (mg) | Solvent | Solvent Amt (mL) | Vol of Solvent Used | Temp °C. | Recovery (mg) | Yield (%) | XRPD Results* | Stoichiometry (HNMR) | HPLC (Area % Purity) |
|---|---|---|---|---|---|---|---|---|---|---|
| GJP-S-15(1) | 155.0 | Acetone | 10.0 | 64 | 50 | 171.0 | 90.2 | Consistent | 1.03:1 | 99.3 |
| GJP-S-16(1) | 100.3 | MEK | 5.0 | 50 | 70 | 104.6 | 85.3 | Consistent | 1.09:1 | 98.7 |
| GJP-S-16(2) | 104.8 | MIBK | 5.0 | 50 | 90 | 118.0 | 92.1 | Consistent | 1.10:1 | 99.0 |
| GJP-S-17(1) | 100.3 | Acetone | 8.0 | 80 | 50 | 106.0 | 86.4 | Consistent | 1.04:1 | 99.4 |
| GJP-S-18(1) | 3507.4 | Acetone | 280 | 80 | 50 | 4019.7 | 93.2 | Consistent | 1:01:1 | 99.5 |

*Indicated result describes similarity to scale up lot GJP-S-10(1)

The first experiment was completed using 64 volumes of acetone and the addition of neat MSA. This amount was picked as a starting point and corresponded to 10 mL of solvent for the 0.155 g used in the experiment. The volumes of acetone was calculated as follows: (10 mL acetone)/(0.155 g)=64 volumes. A slightly oily material observed during the reaction solidified upon cooling and precipitated out of solution following the addition of the acid. This free flowing solid afforded consistent results by XRPD, 1H NMR and HPLC when compared to the final scale up of the mesylate salt. Based on this experiment, the amount of solvent needed to keep the material from oiling out was determined to be higher than 64 volumes.

In an attempt to reduce the amount of oily material produced during the reactions, ketone solvents with higher boiling points such as methyl ethyl ketone (MEK, 80° C.) and methyl isobutyl ketone (MIBK, 117° C.) were investigated.

Using MEK, the free base was weighed into a vial and dissolved in 5 mL of MEK (50 vol.). This solution was stirred at 70° C. for five minutes to ensure dissolution. The methanesulfonic acid (coned) was added in one portion (16 µL, 1.05 equiv). The solution became turbid after the addition of the acid and brown oil formed on the bottom of the vial. The turbid solution was stirred for two minutes before the reaction was cooled to ambient temperature at a rate of 10° C./hour. Precipitation occurred during the cooling phase. The reaction was stirred at ambient temperature for 18 hours. The solids were collected by vacuum filtration. The oil had hardened and was removed from the flask. All solids were dried in vacuo at ambient temperature and 30 in. Hg. This reaction afforded 105 mg (90.2% yield) of an off-white solid. XRPD results were consistent with the results for scale up lot GJP-S-10(1). HPLC purity was 98.7.

Using MIBK, the free base was weighed into a vial and dissolved in 5 mL of MIBK (50 vol). This solution was stirred at 90° C. for five minutes to ensure dissolution. The methanesulfonic acid (coned) was added in one portion (16.5 µL, 1.05 equiv). The solution became turbid after the addition of the acid and a brown oil formed on the bottom of the vial. The turbid solution was stirred for 2 minutes before the reaction was cooled to ambient temperature at a rate of 10° C./hour. Precipitation occurred during the cooling phase. The reaction was stirred at ambient temperature for 18 hours. The solids were collected by vacuum filtration. The oil had hardened and was removed from the flask. All solids were dried in vacuo at ambient temperature and 30 in. Hg. This reaction afforded 118.0 mg (92.1% yield) of an off-white solid. XRPD results were consistent with the results for scale up lot GJP-S-10(1). HPLC purity was 99.0.

While the solvents MEK and MIBK were heated hotter than the acetone reaction, both reactions produced larger amounts of the oily material compared to the acetone reactions. Both reactions also produced a free flowing solid which yielded consistent results by XRPD, $^1$H NMR and HPLC when compared to the final scale up mesylate salt lot; however slight degradation was observed with the use of MEK as the primary solvent.

Acetone was re-investigated using a larger amount of volumes (80 vs. 64). This reaction formed a turbid solution after the addition of the acid, but did not produce any oily material while cooling to ambient temperature. This reaction afforded an 86% yield of an off-white solid with consistent results XRPD, 1H NMR and HPLC when compared to the final scale up mesylate salt lot. This process was used in the scale up for the 3.5 g reaction which yielded 4.0 g of an off-white solid with a 93.7% yield and this process has been transferred to cGMP for the final step of the synthesis.

Example 20

Differential Scanning Calorimetry

Differential Scanning Calorimetric (DSC) analysis was performed on KX2-391•MSA, Form A obtained in accordance with the process described herein (Example 4), and on several samples of other KX2-391 salts. Samples were weighed in an aluminum pan, covered with a pierced lid, and then crimped. Analysis started at 30° C. to 300-350° C. ramped at 10° C./minute.

| Sample of KX2•391 | Onset Temp (° C.) | Peak Temp (° C.) |
|---|---|---|
| Free base | 131.9 | 136.2 |
| di-HCl salt | 156.4 | 188.9 |
| mono-p-tosylate salt Form A | 110.3 | 112.7 |
|  | 130.2 | 158.9 |
| mono-p-tosylate salt Form B | 105.8 | 111.1 |
|  | 157.9 | 162.8 |
| mono-fumarate salt | 136.1 | 153.4 |
| mono-maleate salt | 143.7 | 149.9 |
| mono-mesylate salt, Form A | 159.6 | 163.8 |
| bis-maleate salt | 50.2 | 63.8 |
| bis-fumarate salt Form A | 128.8 | 141.5 |
| bis-fumarate salt Form B | 155.6 | 157.3 |
| bis-phosphate salt | 78.0 | 93.7 |
|  | 120.7 | 128.0 |
|  | 188.3 | 211.6 |
| bis-p-tosylate salt | 84.2 | 94.6 |
|  | 171.6 | 171.6 |

As evidenced from the data presented herein, KX2-391•MSA, Form A has a unique DSC thermogram, differentiating it from other KX2-391 salts. The DSC of KX2-391•MSA, Form A consistently produces a single DSC peak, in contrast to some of the other salt forms of KX2-391, which appear as a doublet.

Example 21

Figure 20:
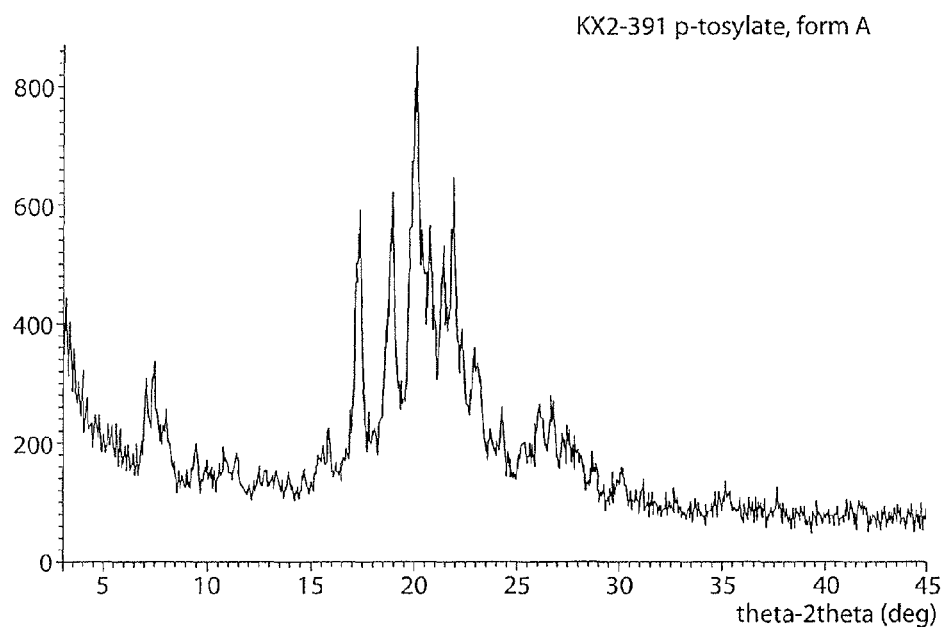
FIG. 20 is a graph indicating the XRPD of KX2-391•p-TSA, Form A.
Figure 21:
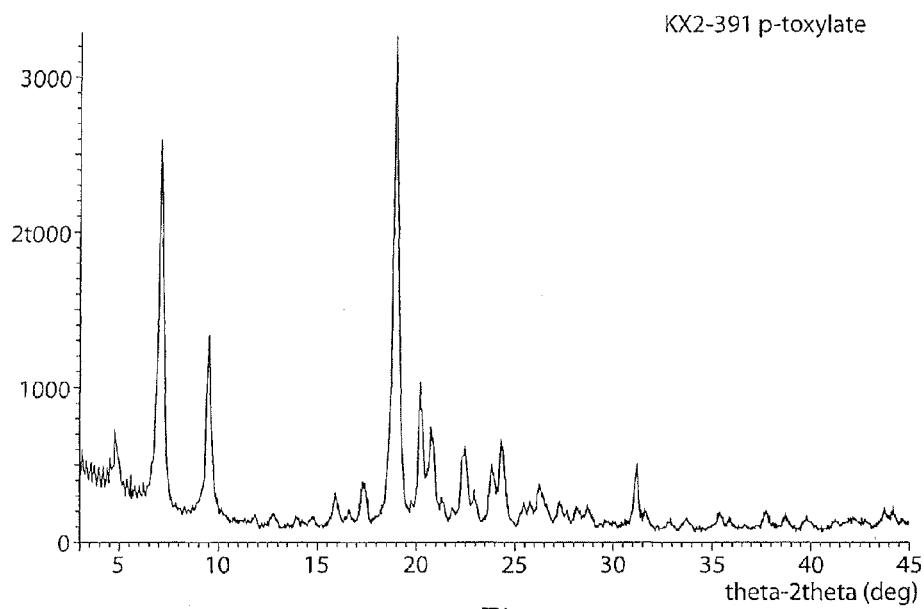
FIG. 21 is a graph indicating the XRPD of KX2-391•p-TSA, Form B.

Characterization of the KX2-391 Mono Salts: p-Tosylate, Fumarate, and Maleate Salt Mono-tosylate of KX2-391 Form A was made with 1 equivalent of p-TSA in dioxane and afforded a semi-cystalline pattern by XRPD as shown in FIG. 20. Mono-tosylate KX2-391 Form B was generated from 1 equivalent of p-TSA in dioxane and afforded a crystalline pattern by XRPD that was found to be unique compared to the 1 equivalent intermediate scale Form A. The XRPD for Form B is shown in FIG. 21.

Figure 22:
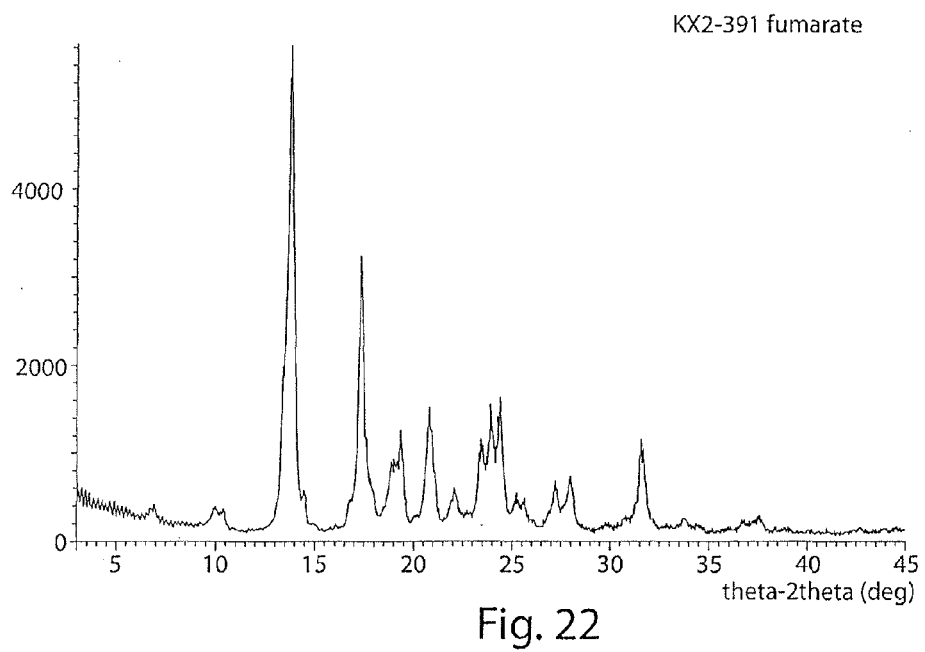
FIG. 22 is a graph indicating the XRPD of KX2-391•fumarate.

The fumarate salt of KX2-391 was generated with 1 equivalent of fumaric acid and the XRPD is shown in FIG. 22.

Figure 23:
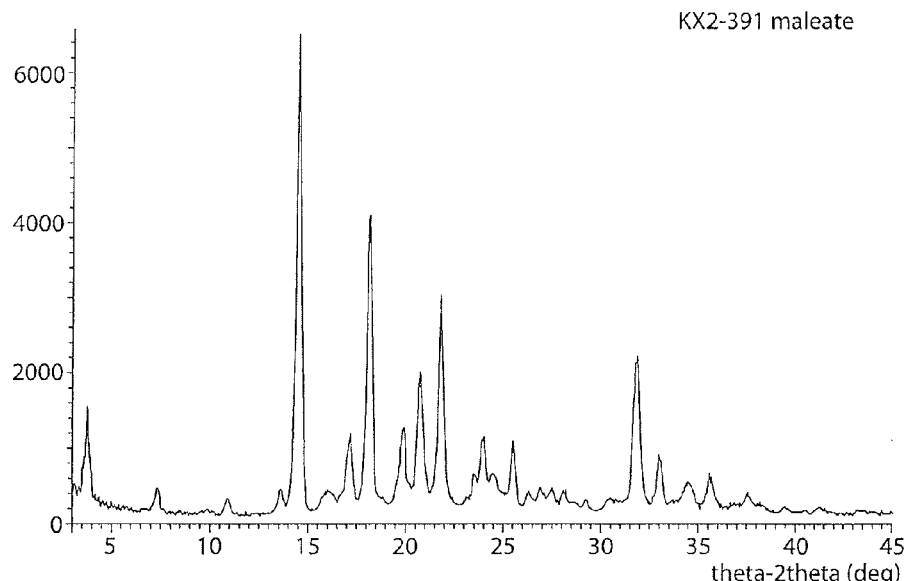
FIG. 23 is a graph indicating the XRPD of KX2-391•maleate.

The maleate salt was generated from 2 equivalents (although 1 equiv was the target ratio) of maleic acid and the XRPD is shown in FIG. 23.

The table below summarizes additional characterization data for the fumaric and maleate KX2-391•MSA salts and compares it to free base, bis-HCl, and MSA salts described above. The results in the table below were obtained using the procedures described above in Examples 5 (XRPD), 6 (DSC), 7 (TGA), and 8 (moisture-sorption).

| Salt | Counterion (Equiv, solvent) | XRPD (form) | TGA % Wt. Loss | Stoichiometry ($^1$H NMR) | Solubility mg/mL (pH) | Moisture Sorption Wt % Water @ 90% RH |
|---|---|---|---|---|---|---|
| Free base | N/A, H$_2$O, DCM | crystalline | NA | consistent | DI H$_2$O: NA<br>pH 2: NA | 3.7 |
| Bis-HCl | 2, EtOH | Semi-crystalline | 9.2 | consistent | DI H$_2$O: >500 (2.1)<br>pH 2: >500 (1.9) | 27.0 |
| MSA | 1, Acetone | Crystalline | 0.0 | 1.07:1 | DI H$_2$O: >500 (4.6)<br>pH 2: >500 (4.3) | 5.7 |
| Fumaric | 1, Acetone | Crystalline Form A | 1.7 | 0.96:1 | DI H$_2$O: 7.6 (4.5*)<br>pH 2: 21.5 (4.5*) | 0.5 |
| Maleate | 1, Acetone | Crystalline Form A | 0.0 | 0.99:1 | DI H$_2$O: 7.3 (4.5*)<br>pH 2: 21.2 (4.5*) | 1.4 |

N/A—sample was not analyzed
pH based on approximate measurement using pH paper instead of meter due to insufficient volume

Example 22

Figure 24:
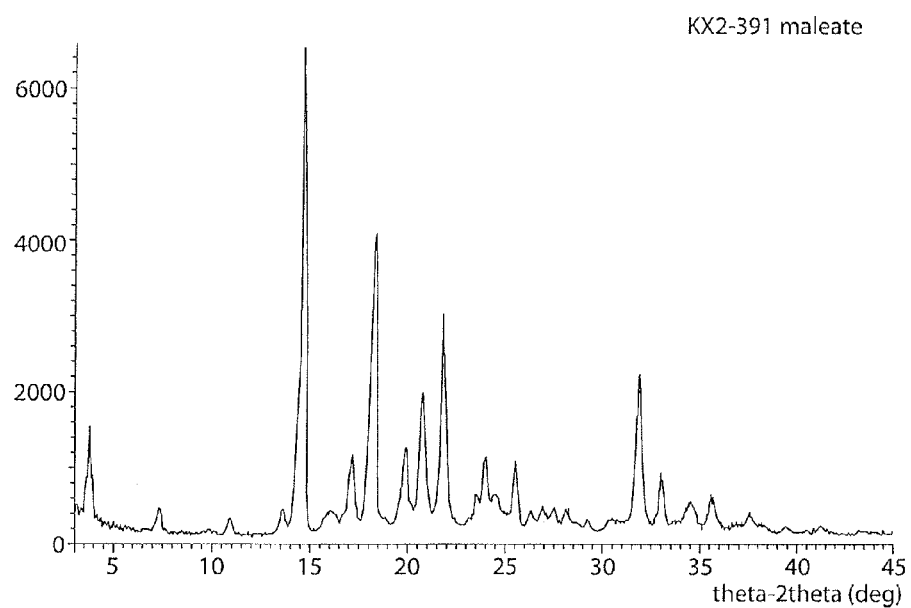
FIG. 24 is a graph indicating the XRPD of KX2-391 bis-maleate.

XRPD Characterization of the KX2-391 Bis-Equivalent Salts: Maleate, Fumarate, and Phosphate Salts Bis-maleate KX2-391 Form A was generated with 2 equivalents of maleic acid in acetone and afforded a semi-crystalline pattern by XRPD as shown in FIG. 24. This pattern was found to be unique compared to the free base indicating successful salt formation. 1H NMR stoichiomety was 1.86:1.

Figure 25:
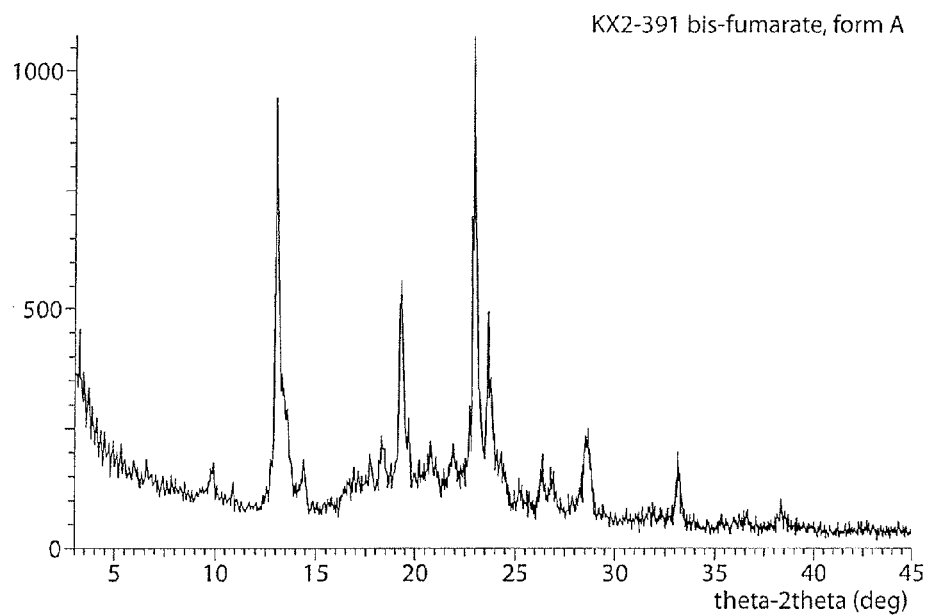
FIG. 25 is a graph indicating the XRPD of KX2-391 bis-fumarate, Form A.
Figure 26:
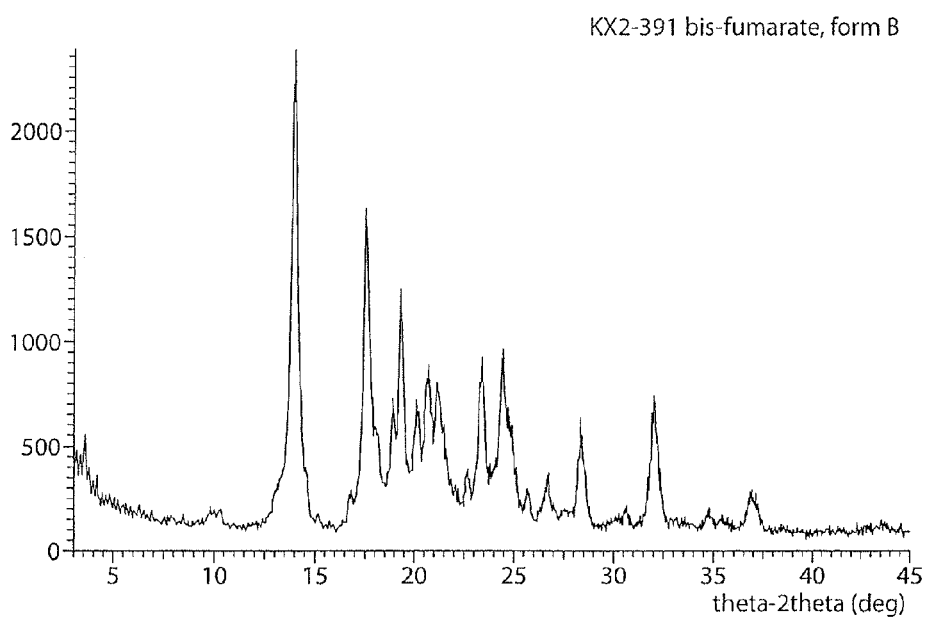
FIG. 26 is a graph indicating the XRPD of KX2-391 bis-fumarate, Form B.

Bis-fumarate KX2-391, Form A was generated with 2 equivalents of fumaric acid in isopropyl alcohol (IPA) and afforded a crystalline pattern by XRPD as shown in FIG. 25. The pattern was observed to be unique when compared to the free base suggesting successful salt formation. $^1$HNMR stoichiometry was 1.93:1. Bis-fumarate KX2-391, Form B is shown in FIG. 26.

Figure 27:
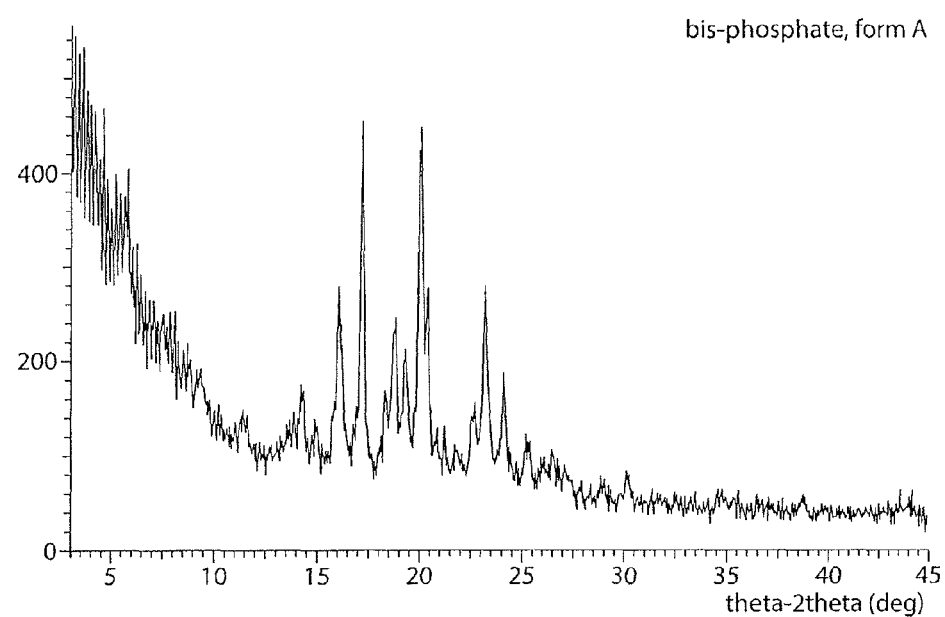
FIG. 27 is a graph indicating the XRPD of KX2-391 bis-phosphate, Form A.
Figure 28:
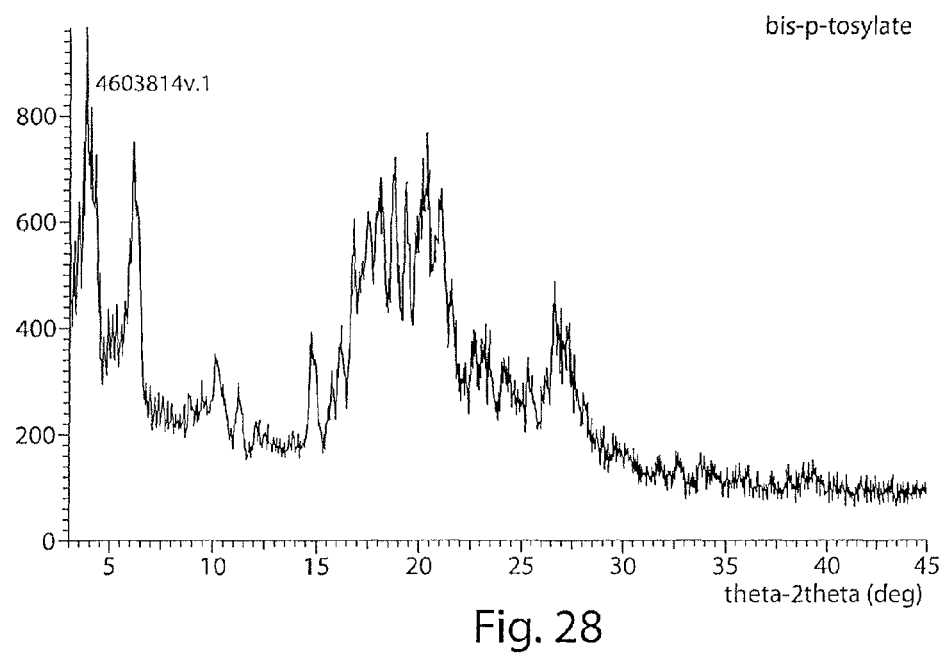
FIG. 28 is a graph indicating the XRPD of KX2-391 bis-p-tosylate.

Bis-phosphate KX2-391 was made with 2 equivalents of phosphoric acid in THF afforded a semi-crystalline pattern by XRPD (Form A) as shown in FIG. 27 and was found to be unique compared to the free base indicating successful salt formation. The percent weight loss was 0.3 and 1.7 as measured by TGA as described in Example 7. $^1$HNMR stoichiometry was 1.95:1.

Bis-p-tosylate KX2-391 was generated with 2 equivalents of p-TSA in dioxane and afforded a semi-crystalline pattern by XRPD as shown in FIG. 27.

Example 23

Solubility Experiments for KX2-391 Salts

Dissolution experiments were performed on KX2-391 salts to provide a better understanding of the salts interaction in water. This was accomplished using a 5 mg/mL DI water dissolution experiment where 5 mg of each salt was weighed into a vial and 1 mL of DI water was added. The solution was monitored visually with magnetic stirring over a 20 minute time period to observe the time of dissolution. The results of 5 mg/mL solubility experiments for the KX2-391 mesylate Form A, fumaric, and maleic salts are shown in the table below. The fumarate and maleate salts were not observed to dissolve solids within 10 minutes and therefore an additional 1 mL of DI water was added.

| | | | Time (s/min) | | | | | | | |
|---|---|---|---|---|---|---|---|---|---|---|
| NB Code | Starting Material (Counterion) | Test Conditions (Utilizing Magnetic Stirring) | 0 s | 30 s | 1 min | 2 min | 5 min | 10 min (1 mLDI water added) | 15 min | 20 min |
| SUC-B-81(1) | GJP-S-10(1) (MSA) | 5.13 mg in 1 mL DI water | P | P | D | | | | | |
| SUC.B.81(2) | GJP-S-10(2) (Fumaric) | 5.31 mg in 1 mL DI water | P | P | P | P | P | P | P | D |
| SUC-B-81(3) | GJP-S-10(3) (Maleic) | 5.10 mg in 1 mL DI water | P | P | P | P | P | P | P | P |

P—Particulates partially dissolved
D—Particulates fully dissolved

Solubility experiments were also performed using pH 2.0 phosphate buffer and DI water pH 6.9 and KX2-391•MSA, Form A. Each vial was filled with approximately 50 mg of KX2-391•MSA, Form A and 100 µL aliquots of the corresponding solvent was added until complete dissolution was observed, followed by stirring at room temperature for one and five days. The solids obtained were isolated by filtration, dried under vacuum at room temperature and analyzed by HPLC. The initial HPLC purity of KX2-391•MSA, Form A was 99.4 (% area). The solubility by HPLC of KX2-391•MSA, Form A in phosphate buffer/RT was >500 mg/mL and HPLC purity was measured to be 99.4. The solubility by HPLC of KX2-391•MSA, Form A in DI H$_2$O/RT was >500 mg/mL and HPLC purity was measured to be 99.4.

Example 24

Birefringence Analysis

Birefringence analysis provides an evaluation of the degrees of crystallinity experienced by the solids generated from the salt screen. By placing the 96 well plate between a cross polarized film, solids of individual wells were analyzed visually for significant birefringence or definitive crystalline particles. Each well containing solids was assigned a numerical rank from 0 to 3 in increasing crystallinity as shown in the table below.

|  |  | 1 Equivalent of Acid |  |  |  |  |  | 2 Equivalents of Acid |  |  |  |  |  |
|---|---|---|---|---|---|---|---|---|---|---|---|---|---|
|  |  | ACN | Acetone | Dioxane | THF | EtOH | IPA | ACN | Acetone | Dioxane | THF | EtOH | IPA |
|  |  | 1 | 2 | 3 | 4 | 5 | 6 | 7 | 8 | 9 | 10 | 11 | 12 |
| Malic | A | 0 | 0 | 1 | 0 | 0 | 0 | 0 | 0 | 0 | 0 | 0 | 0 |
| Fumaric | B | 1 | 2 | 2 | 1 | 0* | 0* | 1 | 1 | 1 | 1 | 0 | 1 |
| Tartaric | C | 0 | 0 | 1 | 0 | 0 | 0 | 0 | 0 | 0 | 0 | 0 | 0 |
| Maleic | D | 1 | 0* | 1 | 1 | 1 | 0* | 0 | 1 | 1 | 1 | 0 | 0 |
| MSA | E | 0 | 1 | 1 | 1 | 0 | 0 | 0 | 0 | 0 | 0 | 0 | 0 |
| p-TSA | F | 0* | 1* | 1* | 1* | 1* | 0* | 0 | 0 | 0 | 0 | 0 | 0 |
| Sulfuric | G | 0 | 0 | 0 | 0 | 0 | 0 | 0 | 0 | 0 | 0 | 0 | 0 |
| Phosphoric | H | 1 | 1 | 1 | 1 | 0 | 1 | 0 | 2 | 1 | 1 | 0 | 1 |

| | |
|---|---|
| 3 | Crystalline |
| 2 | Semi-crystalline |
| 1 | Amorphous |
| 0 | oil/not observed |
| * | Indicates the formation of crystals during threshold solubility |

Example 25

Threshold Solubility

Threshold solubility was evaluated by adding 200 μL aliquots of de-ionized water up to 1 mL to each well of the 96 well plate generated during the salt screen and monitored for complete dissolution. Following each addition, the plate was shaken to encourage mixing for at least 5 minutes prior to evaluation. Upon evaluation a numerical rank (1-5) of increasing solubility was assigned as shown in the table below.

Example 26

Small Scale Synthesis of KX2-391•MSA, Form A from Free Base

The free base (350.1 mg) was weighed into a 100 mL, round-bottom flask and dissolved in acetone (52 mL) with stirring and heating (50° C.) for 5 minutes to ensure dissolution. The methanesulfonic acid (850 μL, 1M solution in acetone) was added in one portion and the solution stayed clear. The reaction was cooled to ambient temperature at a rate of 20° C./hour. Upon reaching ambient temperature material had precipitated out of solution. The reaction was stirred at ambient temperature for 16 hours. This solid was collected by vacuum filtration and dried in vacuo at ambient temperature and 30 in. Hg. This reaction afforded 351.6 mg (72%) of a beige solid.

Example 27

Slurry Study

Slurry experiments were performed using acetone and DI water on KX2-391•MSA, Form A. Each vial was filled with

|  |  | 1 Equivalent of Acid |  |  |  |  |  | 2 Equivalents of Acid |  |  |  |  |  |
|---|---|---|---|---|---|---|---|---|---|---|---|---|---|
|  |  | ACN | Acetone | Dioxane | THF | EtOH | IPA | ACN | Acetone | Dioxane | THF | EtOH | IPA |
|  |  | 1 | 2 | 3 | 4 | 5 | 6 | 7 | 8 | 9 | 10 | 11 | 12 |
| Malic | A |  |  | 1 |  |  |  |  |  |  |  |  |  |
| Fumaric | B | 5 | 5 | 4 | 5 | 2 | 2 | 5 | 5 | 2 | 5 |  | 2 |
| Tartaric | C |  |  | 1 |  |  |  |  |  |  |  |  |  |
| Maleic | D | N | N | N | N | N | N |  | 1 | 1 | 1 |  |  |
| MSA | E |  | 1 | 1 | 1 |  |  |  |  |  |  |  |  |
| p-TSA | F | 5 | 5 | 5 | 5 | 5 | 5 |  |  |  |  |  |  |
| Sulfuric | G |  |  |  |  |  |  |  |  |  |  |  |  |
| Phosphoric | H | 1 | 5 | 1 | 1 |  | 1 |  | 1 | 1 | 1 |  | 1 |

N-Indicates no dissolution observed for 1 ml after 24 h
1-5 Indicates the No. of 200 μL aliquots of DI water added for complete dissolution approximately 30 mg of KX2-391•MSA, Form A and 0.5 and 1 mL of corresponding solvent, followed by stirring at room temperature for one and five days. The obtained solids were isolated by filtration, dried under vacuum at room temperature, and analyzed by HPLC and XRPD. The initial purity of KX2-391•MSA was 99.4%. Acetone slurry/RT test conditions resulted in a solid that produced an XRPD that was consistent with the pattern of the initial KX2-391•MSA, Form A and HPLC purity was measured to be 99.3%.

Example 28

Thermal Stress

Thermal stress experiments were performed on KX2-391•MSA, Form A. Each 1-dram amber vial was filled with approximately 20 mg of KX2-391•MSA, Form A capped and stored in a vacuum over at 60° C. for one week. The resulting solids were analyzed by XRPD and HPLC. Thermal/60° C. test conditions resulted in a solid that produced an XRPD that was consistent with the pattern of the initial KX2-391•MSA, Form A and HPLC purity was measured to be 99.3%. The pattern of the initial KX2-391•MSA, Form A was consistent with the pattern shown in FIG. 7.

Example 29

Effects of Solvent and Cooling Profile on Crystalline Form

The effects of solvent and cooling profile on the crystalline form of KX2-391 mesylate were determined using single and binary solvent crystallizations with both fast and slow cooling. One crystalline form was observed Form A. The crystalline form observed produced an XRPD pattern that was consistent with the pattern shown in FIG. 7.

Example 30

Pressure and Grinding Studies

Pressure and grinding studies were completed to determine the effects of physical stress on the crystalline form of KX2-391 mesylate Form A. No change in crystalline form was observed.

Example 31

Slurry Studies

Slurries of KX2-391 mesylate Form A in five conditions (IPA, 1-butanol, MeCN, THF:water, and dioxane:water) were performed in an attempt to determine if a more stable crystalline form, solvate, or hydrate could be generated. After 2 weeks slurry at ambient conditions, the solids were isolated and analyzed by XRPD and HPLC. No additional forms were observed by XRPD. The results are shown in the table below.

| NB Code | KX2-391-MSA Amt (mg) | Solvent | Solvent Amt (mL) | Initial Form (XRPD) | Form After 2 Weeks (XRPD) | HPLC Purity (AUC) |
|---|---|---|---|---|---|---|
| JSS-T-99(1) | 58.7 | IPA | 1.0 | Form A | Form A | >99% |
| JSS-T-99(2) | 53.7 | 1-butanol | 1.0 | | Form A | >99% |
| JSS-T-99(3) | 57.9 | MeCN | 1.0 | | Form A | >99% |
| JSS-T-99(4) | 51.9* | THF:water (~0.9:0.1) | 1.5 | | Form A | >99% |
| JSS-T-99(5) | 55.6* | Dioxane:water (~0.9:0.1) | 1.5 | | Form A | >99% |

*Additional solid added until residual solids were observed, ~100 mg

Example 32

Aqueous Solubility Study

The solubility of KX2-391 mesylate, Form A was determined in SGF (pH 2), acetate buffer (pH 4.5), and phosphate buffer (pH 7.2). Slurries of KX2-391 mesylate in the buffer solution were allowed to equilibrate overnight at 37° C. The solids were then isolated and the supernatant was diluted and analyzed by HPLC. The response of the supernatant was then compared against a calibration curve to determine the solubility. The results are shown in the table below.

| NB Code | Buffer | pH after slurry | Average Solubility (mg/mL) |
|---|---|---|---|
| JSS-T-100(4) | SGF (pH 2.0) | 4.5 | 700 |
| JSS-T-100(5) | acetate (pH 4.6) | 4.4 | 737 |
| JSS-T-100(6) | phosphate (pH 7.2) | 4.3 | 150 |

The buffers did not maintain pH. Due the high solubility of KX2-391 mesylate, Form A observed, it is unlikely a buffered solution will maintain the pH at desired levels in the pH range studied.

What is claimed is:

1. A polymorph of a salt of 2-(5-(4-(2-morpholinoethoxy)phenyl)pyridin-2-yl)-N-benzylacetamide characterized by an X-ray diffraction pattern substantially similar to that set forth in any one of FIGS. 20-28.

2. The polymorph of claim 1, characterized by an X-ray diffraction pattern substantially similar to that set forth in FIG. 20, and wherein said salt is a p-tosylate.

3. The polymorph of claim 1, characterized by an X-ray diffraction pattern substantially similar to that set forth in FIG. 21, and wherein said salt is a p-tosylate.

4. The polymorph of claim 1, characterized by an X-ray diffraction pattern substantially similar to that set forth in FIG. 22, and wherein said salt is a fumarate.

5. The polymorph of claim 1, characterized by an X-ray diffraction pattern substantially similar to that set forth in FIG. 23, and wherein said salt is a maleate.

6. The polymorph of claim 1, characterized by an X-ray diffraction pattern substantially similar to that set forth in FIG. 24, and wherein said salt is a bis-maleate.

7. The polymorph of claim 1, characterized by an X-ray diffraction pattern substantially similar to that set forth in FIG. 25, and wherein said salt is a bis-fumarate.

8. The polymorph of claim 1, characterized by an X-ray diffraction pattern substantially similar to that set forth in FIG. 26, and wherein said salt is a bis-fumarate.

9. The polymorph of claim 1, characterized by an X-ray diffraction pattern substantially similar to that set forth in FIG. 27, and wherein said salt is a bis-phosphate.

10. The polymorph of claim 1, characterized by an X-ray diffraction pattern substantially similar to that set forth in FIG. 28, and wherein said salt is a bis-p-tosylate.

* * * * *